(12) United States Patent
Uneyama et al.

(10) Patent No.: US 6,995,179 B2
(45) Date of Patent: Feb. 7, 2006

(54) DIHYDROPYRIDINE DERIVATIVE

(75) Inventors: Hisayuki Uneyama, Kanagawa-ken (JP); Seiji Niwa, Kanagawa-ken (JP); Tomoyuki Onishi, Kanagawa-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 191 days.

(21) Appl. No.: 10/013,656

(22) Filed: Dec. 13, 2001

(65) Prior Publication Data

US 2002/0111494 A1 Aug. 15, 2002

Related U.S. Application Data

(63) Continuation of application No. 09/403,592, filed as application No. PCT/JP98/01878 on Apr. 23, 1998, now Pat. No. 6,350,766.

(30) Foreign Application Priority Data

Apr. 25, 1997 (JP) .................................. 9/109283

(51) Int. Cl.
 *A61K 31/4418* (2006.01)
 *A61K 31/443* (2006.01)
 *A61K 31/4436* (2006.01)
 *A61K 31/444* (2006.01)
 *C07D 211/86* (2006.01)

(52) U.S. Cl. ...................... 514/356; 514/332; 514/336; 546/280.4; 546/283.4; 546/318; 546/322

(58) Field of Classification Search ................ 546/321, 546/280.4, 283.4, 318, 322; 514/356, 332, 514/336
 See application file for complete search history.

(56) References Cited

U.S. PATENT DOCUMENTS 6,350,766 B1 * 2/2002 Uneyama et al. ........... 514/356

FOREIGN PATENT DOCUMENTS

| DE | 2 407 115 | 10/1974 |
|---|---|---|
| DE | 26 58 804 | 7/1978 |
| EP | 0 110 073 | 6/1984 |
| EP | 0 173 943 | 3/1986 |
| EP | 0 315 018 | 5/1989 |
| EP | 0 622 368 | 11/1994 |
| EP | 0 657 429 | 6/1995 |
| EP | 0 779 277 | 6/1997 |
| JP | 60-233058 | 11/1985 |
| JP | 61-068488 | * 3/1986 |
| JP | 61-68488 | 4/1986 |
| JP | 63-258874 | 10/1988 |
| JP | 64-75467 | 3/1989 |
| JP | 2-121967 | 5/1990 |
| JP | 3-240773 | 10/1991 |
| WO | WO 93/13128 | 7/1993 |

OTHER PUBLICATIONS

Iqbal, Nadeem, et al. "Synthesis, Rotamer Orientation, and Ca. Channel Modulation Activities of alkyl and 2-phenethyl 1,4-dihydro-2,6-dimethyl-3-nitro-4-(3- or 6-subst.-2-pyridyl)-5-pyridinecarboxylates" J. of Med. Chem. (1998), 41(11), pp. 1827-1837.*
Iqbal et al "Synthesis, Rotamer Orientation, and Ca. Channel Modulation Activities of alkyl and 2-phenylethyl 1,4-dihydro-2,6-dimethyl-3-nitro-4-(3- or 6- subst. 2-pyridyl)-5-pyridinecarboxylates" J. of Med. Chem. (1998), 41(11), pp. 1827-1837.*
Iqbal, Nadeem, et al. "Synthesis, Rotamer Orientation, and Ca. Channel Modulation Activities of alkyl and 2-phenethyl 1,4-dihydro-2,6-dimethyl-3-nitro-4-(3- or 6-subst.-2-pyridyl)-5-pyridinecarboxylates" J. of Med. Chem. (1998), 41(11), pp. 1827-1837.*
Masahiro Hosono et al., *Inhibitory Effect of Cilnidipine on Vasocular Sympathetic Neurotransmission and Subsequent Vasoconstriction in Spontaneously Hypertensive Rats*, Jpn. J. Pharmacol., vol. 69, pp. 127-134, 1995.
Shigeo Fujii et al., *Effect of Cilnidipine, a Novel Dihydropyridine Ca ++ -Channel Antagonist, on N-Type Ca++ Channel in Rat Dorsal Root Ganglion Neurons*, The Journal of Pharmacology and Experimental Therapeutics, vol. 280, N. 4, pp. 1184-1191, 1997.
Natsuki Nakayama et al., *Antihypertensive Activity of OPC-13340, a New Potent and Long-Acting Dihydropyridine Calcium Antagonist, in Rats*, Journal of Cardiovascular Pharmacology, vol. 15, pp. 836-844, 1990.
Virginia D. Monje et al., *A New Conus Peptide Ligand for Ca Channel Subtypes*, Neuropharmacology, vol. 32, No. 11, pp. 1141-1149, 1993.
Hisayuki Uneyama et al., *Blockage of N-Type $Ca^{2+}$ Current by Cilnidipine (FRC-8653) in Acutely Dissociated Rat Sympathetic Neurones*, British Journal of Pharmacology, vol. 122, pp. 37-42, 1997.

* cited by examiner

Primary Examiner—Joseph K. McKane
Assistant Examiner—Janet L. Coppins
(74) Attorney, Agent, or Firm—Oblon, Spivak, McClelland, Maier & Neustadt, P.C.

(57) ABSTRACT

Dihydropyridine derivatives of the following formula, analogs thereof and pharmaceutically acceptable salts thereof have an activity of selectively inhibiting the action of N-type calcium channel. They are used as remedies for various diseases relating to the N-type calcium channel such as encephalopathies caused by the ischemia in the acute phase after the onset of cerebral infarction, cerebral hemorrhage or the like, Alzheimer's disease, etc.

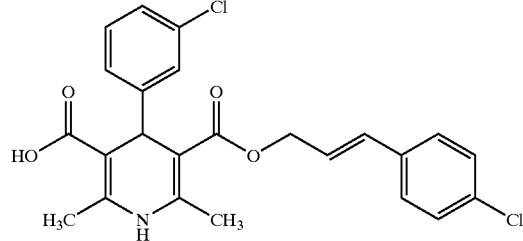

16 Claims, No Drawings

DIHYDROPYRIDINE DERIVATIVE

This application is a Continuation of U.S. application Ser. No. 09/403,592, filed on Oct. 25, 1999, now U.S. Pat. No. 6,350,766 which is a 371 of PCT/JP98/01878, filed Apr. 23, 1998.

BACKGROUND OF THE INVENTION

The present invention relates to new dihydropyridine derivatives, and the use of the dihydropyridine derivatives as medicines. It is said that the activation of N-type calcium channel is concerned with diseases such as encephalopathies caused by the ischemia in the acute phase after the onset of cerebral infarction, cerebral hemorrhage (including subarachnoidal bleeding) or the like; progressive neurodegenerative diseases, e.g. Alzheimer's disease; AIDS related dementia; Parkinson's disease; dementia caused by cerebrovascular disorders and ALS; neuropathy caused by head injury; various pains, e.g. sharp pain caused by spinal injury, diabetes or thromboangitis obliterans; pain after an operation; migraine and visceral pain; various diseases caused by psychogenic stress, e.g. bronchial asthma; unstable angina and hypersensitive colon inflammation; emotional disorder; and drug addiction withdrawal symptoms, e.g. ethanol addiction withdrawal symptoms. The compounds of the present invention are effective in inhibiting the activation of N-type calcium channel and, therefore, they are usable as remedies for the above-described diseases.

The calcium channels are now classified into subtypes L, N, P, Q, R and T. Each of the subtypes is distributed specifically to organs. Particularly, it is known that N-type calcium channel is widely distributed in the central nerves, peripheral nerves and adrenal medulla cells and that this calcium channel is concerned with the death of neurons, control of blood catecholamine dynamics and control of senses such as perceptivity.

It was confirmed that peptides, omega conotoxin GVIA and omega conotoxin MVIIA which selectively inhibit the function of N-type calcium channel inhibit the release of excitatory neurotransmitter from a brain slice sample. It was confirmed by animal experiments that they prevent the advancement of neuron necrosis in a cerebrovascular disorder. It is generally considered that a compound having a clinical effect of inhibiting the function of N-type calcium channel is effective in curing encephalopathies caused by the ischemia in the acute phase after the onset of cerebral infarction, cerebral hemorrhage (including subarachnoidal bleeding) or the like; progressive neurodegenerative diseases, e.g. Alzheimer's disease; AIDS related dementia; Parkinson's disease; dementia caused by cerebrovascular disorders and ALS; neuropathy caused by head injury. In addition, it was also confirmed by animal experiments that omega conotoxin MVIIA gets rid of formalin-caused sharp pain, hot plate pain, sharp pain caused by peripheral neuropathy, etc. Therefore, this medicine is considered to be clinically effective for relieving various pains such as sharp pain caused by spinal injury, diabetes or thromboangitis obliterans; pain after an operation; migraine; and visceral pain. Further, omega conotoxin GVIA inhibits the release of catecholamine from cultured sympathetic ganglion cells, the constriction reaction of an isolated blood vessel by the electric stimulation of governing nerves, and the acceleration of catecholamine secretion from dog adrenal medulla, etc. Therefore, it is considered that compounds having the N-type calcium channel-inhibiting activity are clinically effective in treating various diseases caused by psychogenic stress, e.g. bronchial asthma, unstable angina and hypersensitive colon inflammation [Neuropharmacol., 32, 1141(1993)].

Although several peptide compounds and non-peptide compounds which selectively react on the N-type calcium channel have been disclosed hitherto (for example, WO 9313128), they are not yet used as practical medicines. Some of known compounds which react on the N-type calcium channel also react on other calcium channels than the N-type calcium channel [British Journal of Pharmacology, 122 (1), 37–42, 1997]. For example, compounds which are also antagonistic to L-type calcium channel, which deeply concern with the hypotensive effect, were incompatible with diseases for which N-type antagonists are efficacious (such as cerebral stroke, and pain caused of neuralgia, terminal cancer and spinal injury or the like).

DISCLOSURE OF THE INVENTION

An object of the present invention is to provide new compounds having a selectively antagonistic effect on N-type calcium channel.

Another object of the present invention is to provide antagonists to the N-type calcium channel.

Still another object of the present invention is to provide remedies for encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after operation, migraine, visceral pain, bronchial asthma, unstable angina, hypersensitive colon inflammation and drug addiction withdrawal symptoms.

The above-described objects and other objects of the present invention will be apparent from the following description and Examples.

The inventors synthesized various dihydropyridine derivatives, and made investigations on the effects of these newly synthesized compounds and known dihydropyridine derivatives for inhibiting the electric current of N-type calcium channel. After the investigations, the inventors have found that some specified, new dihydropyridine derivatives have excellent, selective antagonistic effect on the N-type calcium channel. The present invention has been completed on the basis of this finding.

Namely, the present invention provides dihydropyridine derivatives of following general formula (1) or pharmaceutically acceptable salts thereof:

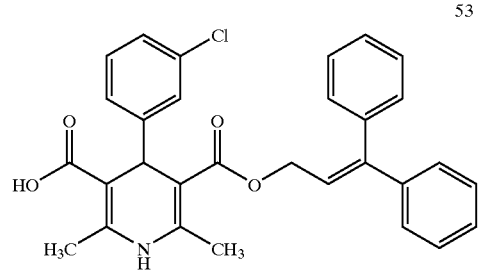

wherein A represents a group of following general formula (2), 1-naphthyl group, 2-naphthyl group, thiophene-2-yl group, furan-3-yl group, furan-2-yl group, pyridine-4-yl group, pyridine-3-yl group or pyridine-2-yl group:

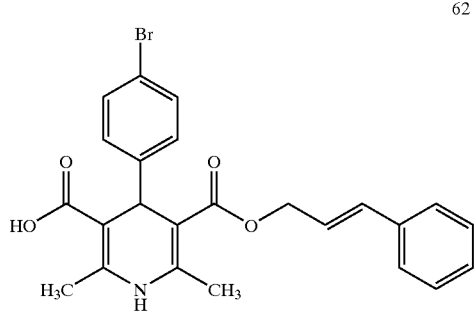

wherein $R^1$, $R^3$ and $R^5$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower alkoxycarbonyl group or an aroyl group, and $R^2$ and $R^4$ may be the same or different from each other, and each represent hydrogen atom, a halogen atom, hydroxyl group, carboxyl group, amino group, cyano group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower alkoxycarbonyl group or an aroyl group, B represents carbamoyl group, cyano group, nitro group, acetyl group or carboxyl group, C represents hydrogen atom, methyl group, ethyl group or dimethoxymethyl group, D represents hydrogen atom, a lower alkyl group, a hydroxy-lower alkyl group or an aryl-lower alkyl group, E represents hydrogen atom, methyl group, ethyl group, dimethoxymethyl group or cyano group, F represents a group of following general formula (3), thiophene-3-yl group, thiophene-2-yl group, furan-3-yl group, furan-2-yl group, pyridine-4-yl group, pyridine-3-yl group or pyridine-2-yl group:

(3)

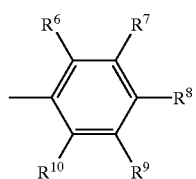

wherein $R^6$, $R^7$, $R^8$, $R^9$ and $R^{10}$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower alkoxycarbonyl group or an aroyl group, X represents an interatomic bond, —$CH_2$—, —$CH_2CH_2$—, —CH=CH— or —C≡C—, and Y represents a group of any of following general formulae (4) to (13):

(4)

(5)

(6)

(7)

(8)

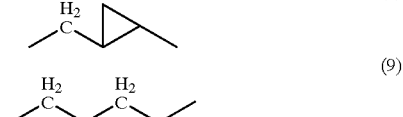

(9)

(10)

(11)

(12)

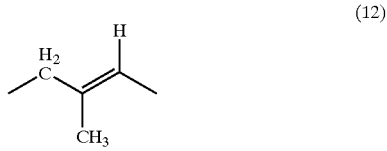

(13)

wherein two of $R^1$ to $R^3$ may be bonded together to form a ring.

The present invention also provides compounds of the above general formula (1) wherein A, C, D, E and X are as defined above, $R^1$, $R^2$, $R^3$, $R^4$ and $R^5$ may be the same or different from each other, and each represent hydrogen atom, a halogen atom, hydroxyl group, carboxyl group, cyano group, nitro group, a lower alkyl group, a lower alkoxyl group, a halogeno-lower alkyl group or a lower alkoxycarbonyl group, with the proviso that either $R^2$ or $R^4$ must be nitro group, B represents carbamoyl group, nitro group or acetyl group, F represents a group of general formula (3), cyclohexyl group, thiophene-3-yl group, thiophene-2-yl group, furan-3-yl group, furan-2-yl group, pyridine-4-yl group, pyridine-3-yl group or pyridine-2-yl group, $R^6$, $R^7$, $R^8$, $R^9$ and $R^{10}$ may be the same or different from each other, and each represent hydrogen atom, a halogen atom, hydroxyl group, carboxyl group, a lower alkyl group, a lower alkoxyl group or a lower alkoxycarbonyl group, and Y represents a group of any of general formulae (4) to (12).

The present invention also provides an antagonist to the N-type calcium channel, which contains a dihydropyridine derivative of following general formula (1) or a pharmaceutically acceptable salt thereof as the active ingredient:

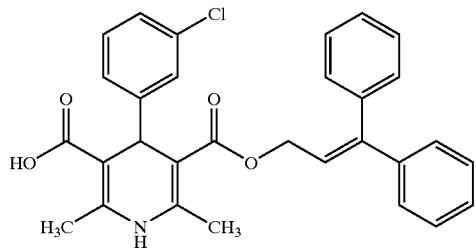

(53)

wherein A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group or pyridine-2-yl group:

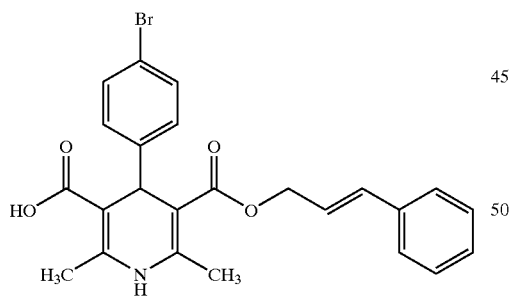

(62)

wherein $R^1$, $R^2$, $R^3$, $R^4$ and $R^5$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower alkoxycarbonyl group or an aroyl group, B represents carbamoyl group, cyano group, nitro group, acetyl group or carboxyl group, C represents hydrogen atom, methyl group, ethyl group or dimethoxymethyl group, D represents hydrogen atom, a lower alkyl group, a hydroxy-lower alkyl group or an aryl-lower alkyl group, E represents hydrogen atom, methyl group, ethyl group, dimethoxymethyl group or cyano group, F represents a group of following general formula (3), cyclohexyl group, thiophene-3-yl group, thiophene-2-yl group, furan-3-yl group, furan-2-yl group, pyridine-4-yl group, pyridine-3-yl group or pyridine-2-yl group:

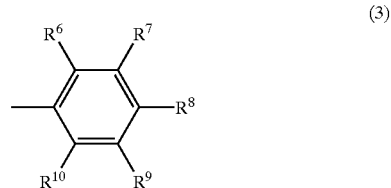

(3)

wherein $R^6$, $R^7$, $R^8$, $R^9$ and $R^{10}$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower alkoxycarbonyl group or an aroyl group, X represents an interatomic bond, —$CH_2$—, —$CH_2CH_2$—, —CH=CH— or —C≡C—, and Y represents a group of any of following general formulae (4) to (16):

(4)

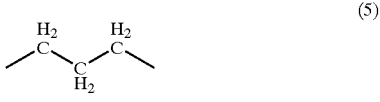

(5)

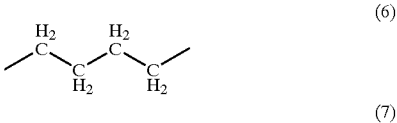

(6)

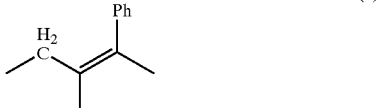

(7)

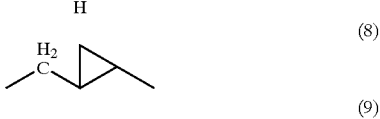

(8)

(9)

-continued

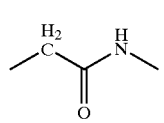
(10)

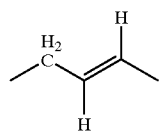
(11)

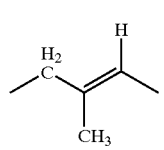
(12)

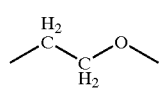
(13)

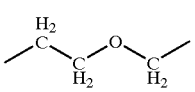
(14)

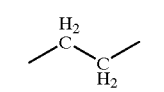
(15)

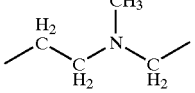
(16)

wherein two of $R^1$ to $R^3$ may be bonded together to form a ring.

The present invention further provides a medicine containing the above-described dihydropyridine derivative or a pharmaceutically acceptable salt thereof as the active ingredient, and usable for any of encephalopathies caused by the ischemia in the acute phase after the onset of cerebral infarction, cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine and visceral pain, bronchial asthma, unstable angina, hypersensitive colon inflammation, and drug addiction withdrawal symptoms.

The present invention also provides a medicinal composition containing the above-described dihydropyridine derivative or a pharmaceutically acceptable salt thereof, a carrier and/or a diluent.

BEST MODE FOR CARRYING OUT THE INVENTION

The term "lower" herein indicates that the group has 1 to 6 carbon atoms. The alkyl groups themselves and the alkyl groups in the alkoxyl, alkenyl, alkylamino, alkylthio and alkanoyl groups may be either linear or branched. The alkyl groups are, for example, methyl group, ethyl group, propyl group, isopropyl group, butyl group and secondary and tertiary butyl groups. Among them, those having 1 to 3 carbon atoms are preferred. The aryl-lower alkoxyl groups include, for example, benzyloxy group. The halogen atoms indicate fluorine, chlorine, bromine and iodine atoms. Examples of the aryl groups include phenyl group and substituted phenyl groups, and the substituents thereof are particularly halogens, alkyl groups and alkoxyl groups. Examples of the aroyl groups include benzoyl group and pyridylcarbonyl group.

In general formula (2) for the medicine containing the above-described dihydropyridine derivative or a pharmaceutically acceptable salt thereof as the active ingredient, and usable for any of N-type calcium channel antagonists, encephalopathies caused by the ischemia in the acute phase after the onset of cerebral infarction, cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine and visceral pain, bronchial asthma, unstable angina and hypersensitive colon inflammation, and drug addiction withdrawal symptoms, $R^1$, $R^2$, $R^3$, $R^4$ and $R^5$ may be the same or different from each other, and each preferably represent hydrogen atom, a halogen atom, hydroxyl group, carboxyl group, cyano group, nitro group, a lower alkyl group, a lower alkoxyl group, a halogeno-lower alkyl group or a lower alkoxycarbonyl group.

Preferably, A in general formula (1) is represented by general formula (2) wherein $R^1$, $R^3$, $R^4$ and $R^5$ each represent hydrogen atom, and $R^2$ represents chlorine atom, bromine atom, iodine atom or cyano group, B represents carboxyl group, C represents methyl group, D represents hydrogen atom, E represents methyl group, F represents phenyl group, X represents an interatomic bond, and Y is represented by general formula (11).

In the present invention, preferred dihydropyridine derivatives are those of general formula (1) or pharmaceutically allowable salts thereof, wherein $R^1$, $R^3$ and $R^5$ in general formula (2) may be the same or different from each other, and they each represent hydrogen atom, a halogen atom, hydroxyl group, carboxyl group, cyano group, nitro group, a lower alkyl group, a lower alkoxyl group, a halogeno-lower alkyl group or a lower alkoxycarbonyl group, and $R^2$ and $R^4$ may be the same or different from each other, and they each represent hydrogen atom, a halogen atom, hydroxyl group, carboxyl group, cyano group, a lower alkyl group, a lower alkoxyl group, a halogenoalkyl group or a lower alkoxycarbonyl group (preferred embodiment I).

Preferably, D is hydrogen atom, X is the interatomic bond and Y is the group of formula (11).

B is preferably carboxyl group.

In preferred embodiment I, A is represented by general formula (2) wherein $R^1$, $R^3$, $R^4$ and $R^5$ each represent hydrogen atom, and $R^2$ represents chlorine atom, bromine atom, iodine atom or cyano group, B represents carboxyl group, C represents methyl group, D represents hydrogen atom, E represents methyl group, F represents phenyl group and X represents the interatomic bond.

Also preferably, A is represented by general formula (2) wherein $R^1$, $R^3$, $R^4$ and $R^5$ each represent hydrogen atom, and $R^2$ represents chlorine atom, bromine atom, iodine atom or cyano group, B represents carboxyl group, C represents methyl group, D represents hydrogen atom, E represents methyl group, F represents phenyl group and Y is represented by formula (11).

Preferably, A is represented by general formula (2) wherein $R^1$, $R^3$, $R^4$ and $R^5$ each represent hydrogen atom, and $R^2$ represents chlorine atom, bromine atom, iodine atom or cyano group, C represents methyl group and E represents methyl group.

Preferably, A is represented by general formula (2) wherein $R^1$, $R^3$, $R^4$ and $R^5$ each represent hydrogen atom, and $R^2$ represents chlorine atom, bromine atom, iodine atom or cyano group, C represents hydrogen atom or methyl group and F represents phenyl group.

In preferred embodiment I, A is represented by general formula (2) wherein $R^1$, $R^3$, $R^4$ and $R^5$ each represent hydrogen atom, and $R^2$ represents chlorine atom, bromine atom, iodine atom or cyano group, B represents carboxyl group, C represents methyl group, E represents methyl group, F represents phenyl group, X represents the interatomic bond and Y is represented by formula (11).

Preferably, A is represented by general formula (2) wherein $R^1$, $R^3$, $R^4$ and $R^5$ each represent hydrogen atom, and $R^2$ represents chlorine atom, bromine atom, iodine atom or cyano group, E represents methyl group and F represents phenyl group.

Preferably, A is represented by general formula (2) wherein $R^1$, $R^3$, $R^4$ and $R^5$ each represent hydrogen atom, and $R^2$ represents chlorine atom, bromine atom, iodine atom or cyano group, C represents methyl group, E represents methyl group and F represents phenyl group.

Preferably, C represents methyl group, E represents methyl group and F represents phenyl group.

Preferably, A is represented by general formula (2) wherein $R^1$, $R^3$, $R^4$ and $R^5$ each represent hydrogen atom, and $R^2$ represents chlorine atom, bromine atom, iodine atom or cyano group.

Preferred dihydropyridine derivatives or pharmaceutically acceptable salts thereof are those of the general formula (1) wherein A represents a group of above general formula (2) wherein $R^1$ and $R^3$ may be the same or different from each other, and each represent hydrogen atom, a halogen atom, hydroxyl group, amino group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group or an aroyl group, $R^2$ represents hydrogen atom, a halogen atom, hydroxyl group, amino group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group or an aroyl group, and $R^4$ and $R^5$ each represent hydrogen atom, with the proviso that two of $R^1$ to $R^3$ may form a ring together, B represents carboxyl group,
C represents methyl group,
D represents hydrogen atom, a lower alkyl group, a hydroxy-lower alkyl group or an aryl-lower alkyl group,
E represents methyl group,
F represents a group of general formula (3) wherein $R^6$, $R^7$, $R^8$, $R^9$ and $R^{10}$ may be the same or different from each other, and each represent hydrogen atom, a halogen atom, hydroxyl group, amino group, nitro group, a lower alkyl group, a lower alkoxyl group, a lower alkenyl group, a lower alkylamino group, a lower alkylthio group, a lower alkanoyl group, a hydroxy-lower alkyl group, a hydroxy- lower alkoxyl group, a hydroxy-lower alkenyl group, a halogeno-lower alkyl group, a halogeno-lower alkoxyl group, an aryl-lower alkoxyl group or an aroyl group, X represents an interatomic bond, and
Y represents a group of formula (5), (11) or (12).

The present invention further provides an N-type calcium channel antagonist, a medicinal composition and a medicine containing the above-described, preferred dihydropyridine derivative or a pharmaceutically acceptable salt thereof as the active ingredient, and usable for any of encephalopathies caused by the ischemia in the acute phase after the onset of cerebral infarction, cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine and visceral pain, bronchial asthma, unstable angina, hypersensitive colon inflammation, and drug addiction withdrawal symptoms.

The dihydropyridine derivatives (1) of the present invention can be produced by processes described below.

For example, dihydropyridine derivatives (1-1) wherein D is hydrogen atom and B is carboxyl group can be produced according to the following flow chart:

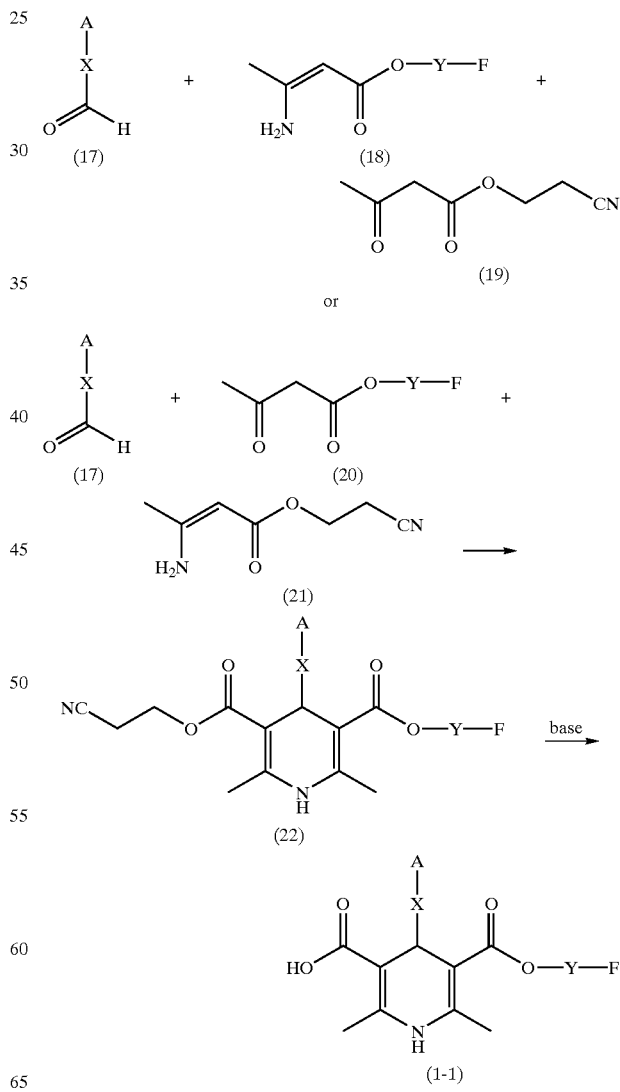

wherein A, F, X and Y are as defined above.

Namely, a dihydropyridinedicarboxylic acid diester (22) can be obtained by reacting an aldehyde (17), a 3-aminocrotonic ester (18) and 2-cyanoethyl acetoacetate (19), or by reacting the aldehyde (17), an acetoacetic ester (20) and 2-cyanoethyl 3-aminocrotonate (21). Then the dihydropyridinedicarboxylic acid diester thus obtained is treated with a base such as sodium hydroxide to obtain a dihydropyridinecarboxylic acid derivative (1-1) of the present invention.

Further, the dihydropyridine derivatives (1-1) can be obtained according to the following flow chart:

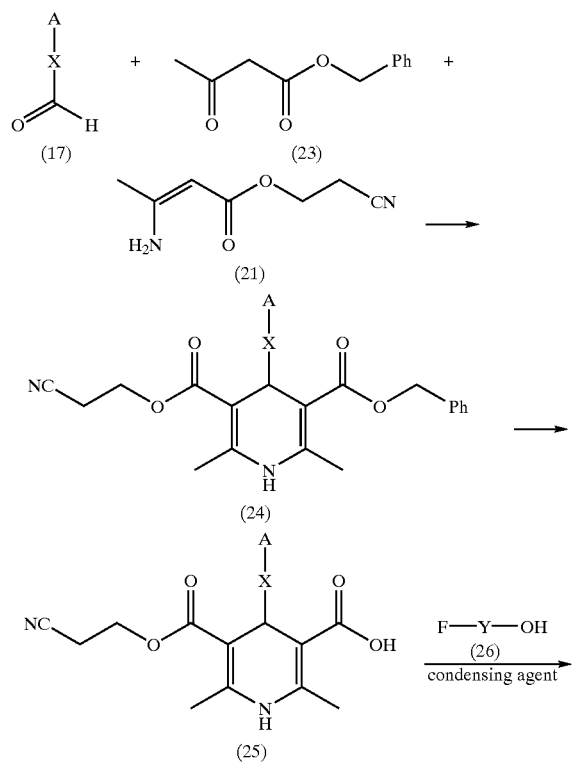

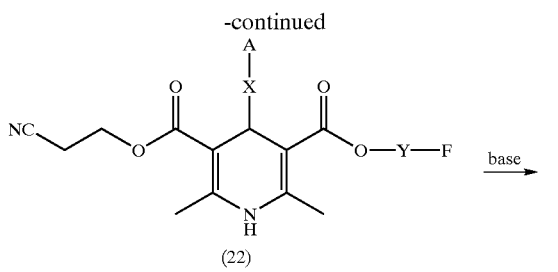

Namely, a cyanoethyl benzyl dihydropyridinedicarboxylate (24) can be obtained by reacting an aldehyde (17), benzyl acetoacetate (23) and 2-cyanoethyl 3-aminocrotonate (21). Then the obtained ester (24) is hydrogenated in ethyl acetate in the presence of a palladium catalyst to obtain monocyanoethyl dihydropyridinedicarboxylate (25). This ester (25) is reacted with an alcohol (26) in the presence of a condensing agent such as WSC to obtain a dihydropyridinedicarboxylic acid diester (22), which is then treated with a base such as sodium hydroxide to obtain a dihydropyridinecarboxylic acid derivative (1-1) of the present invention.

Dihydropyridinecarboxylic acid derivatives (1-2) wherein the substituent of the ester is a carboxyl group-substituted cinnamyl can be obtained by the following process:

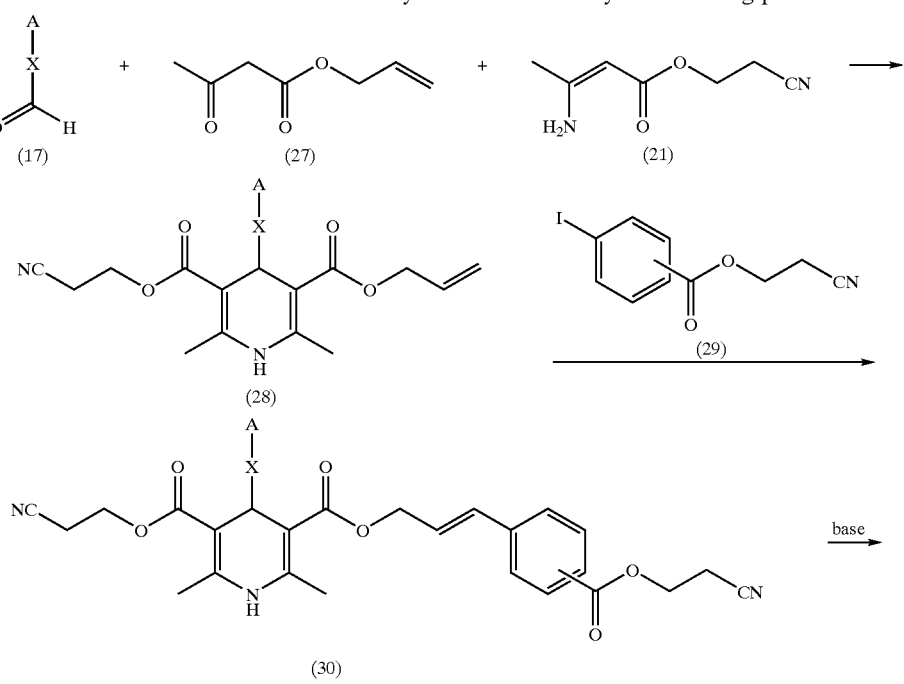

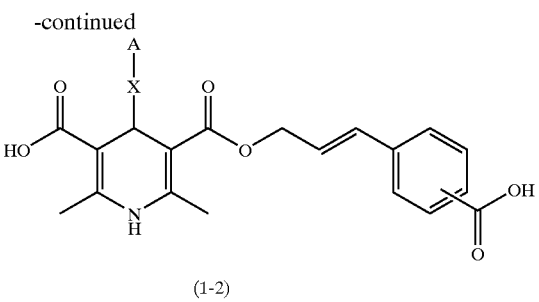

(1-2)

Namely, dihydropyridinecarboxylic acid derivatives (1-2) of the present invention can be produced by subjecting a dihydropyridinedicarboxylic ester (28) to Heck reaction in the presence of a palladium catalyst and then treating the reaction product with a base such as sodium hydroxide.

Dihydropyridine derivatives (1-3) wherein B is carbamoyl group can be produced by reacting an aldehyde (17), a 3-aminocrotonic ester (18) and acetoacetamide (31) according to the following flow chart:

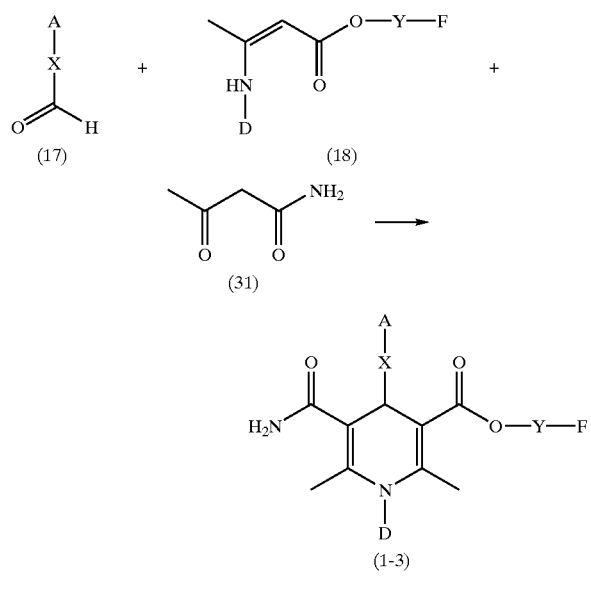

wherein A, D, F, X and Y are as defined above.

Dihydropyridine derivatives (1-4) wherein B is cyano group can be produced by reacting an aldehyde (17), an acetoacetic ester (20) and 3-aminocrotonitrile (32) according to the following flow chart:

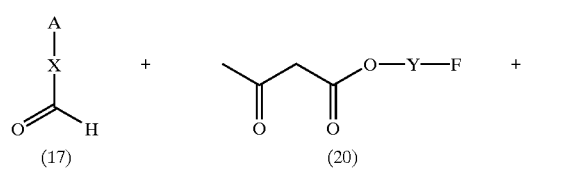

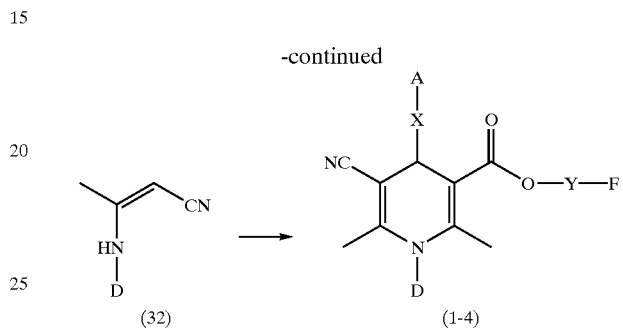

Dihydropyridine derivatives (1-5) wherein B is nitro group can be produced by reacting an aldehyde (17), a 3-aminocrotonic ester (18) and nitroacetone (33) according to the following flow chart:

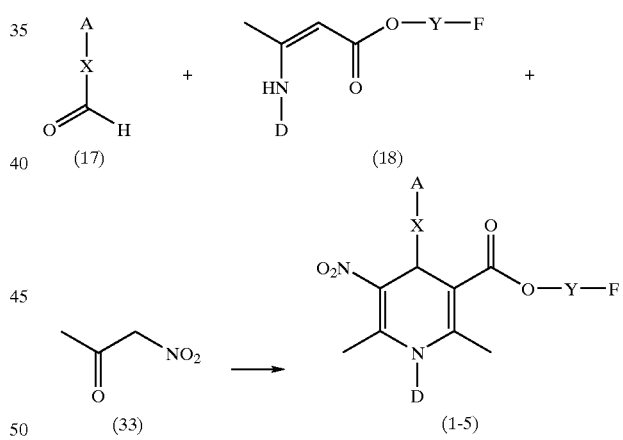

wherein A, D, F, X and Y are as defined above.

Dihydropyridine derivatives (1-6) wherein B is acetyl group can be produced-by reacting an aldehyde (17), a 3-aminocrotonic ester (18) and acetylacetone (34) according to the following flow chart:

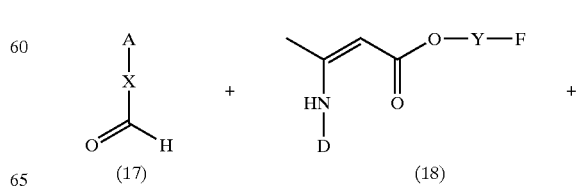

-continued

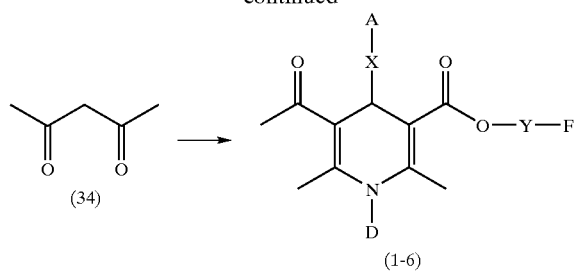

wherein A, D, F, X and Y are as defined above.

Dihydropyridine derivatives (1-7) wherein D is a substituent other than hydrogen atom and B is carboxyl group can be produced by, for example, as follows: An aldehyde (17), a 3-aminocrotonic ester (18) and 2-trimethylsilylethyl acetoacetate (35) are reacted together to obtain a dihydropyridinedicarboxylic diester (36), which is then reacted with an alkyl halide or the like in the presence of a base such as sodium hydride to obtain a product (37), which is treated with, for example, tetrabutylammonium fluoride to obtain a dihydropyridine derivative (1-7) wherein D is substituted.

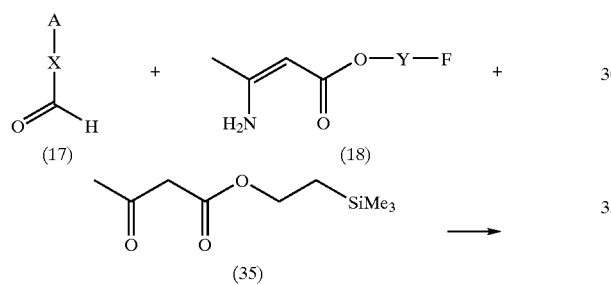

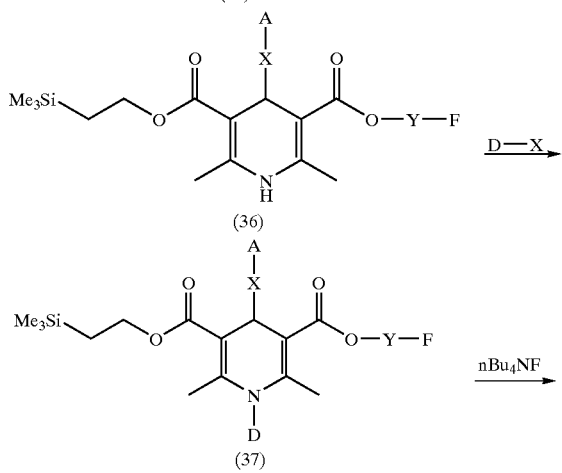

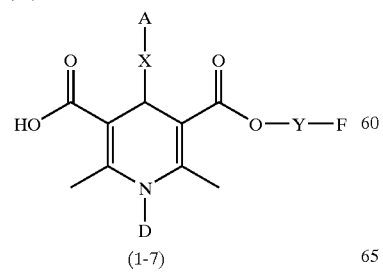

wherein A, D, F, X and Y are as defined above.

Dihdropyridine derivatives (1-8) wherein E is hydrogen atom can be produced from, for example, an acetylenecarboxylic ester (38) according to the following flow chart:

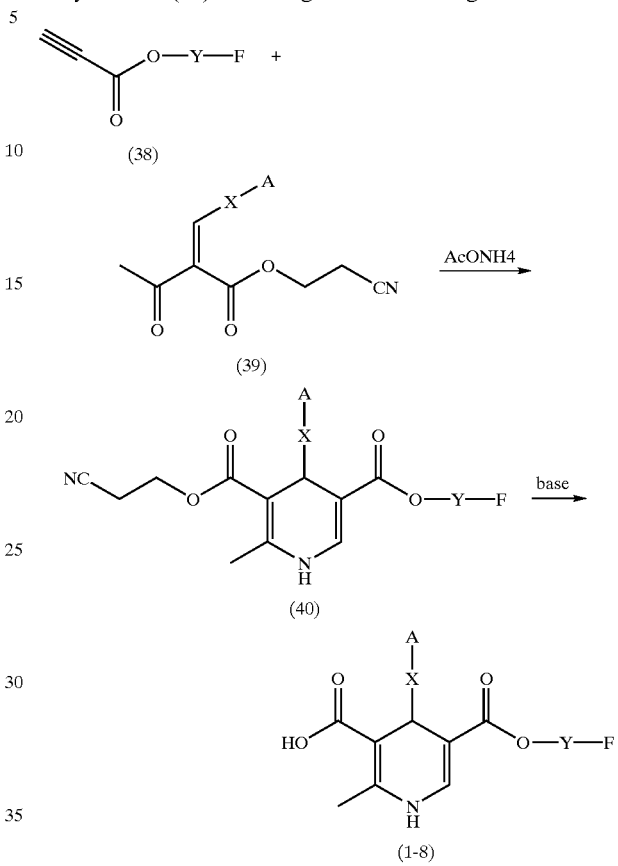

wherein A, F, X and Y are as defined above.

Dihydropyridine derivatives (1-9) wherein C is hydrogen atom can be produced from, for example, an acetylenecarboxylic ester (41) according to the following flow chart:

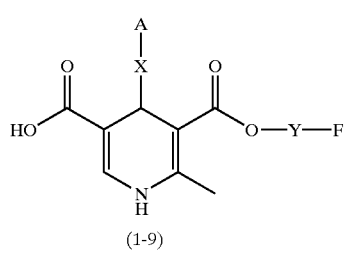

(1-9)

wherein A, F, X and Y are as defined above.

Dihydropyridine derivatives (1-10) wherein both C and E are each hydrogen atom can be produced from, for example, acetylenecarboxylic esters (38) and (41) according to the following flow chart:

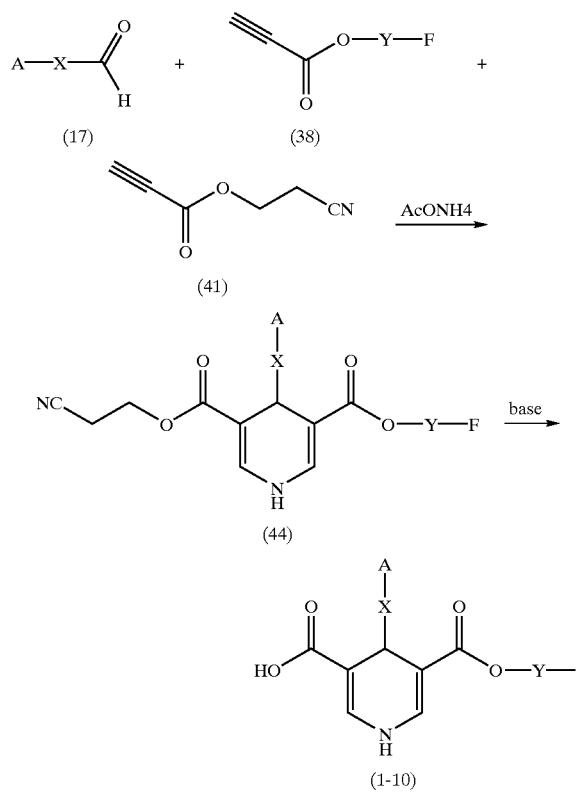

wherein A, F, X and Y are as defined above.

Dihydropyridine derivatives (1-11) wherein E is ethyl group can be produced from, for example, 3-oxovaleric esters (45) according to the following flow chart:

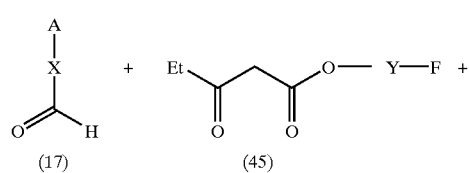

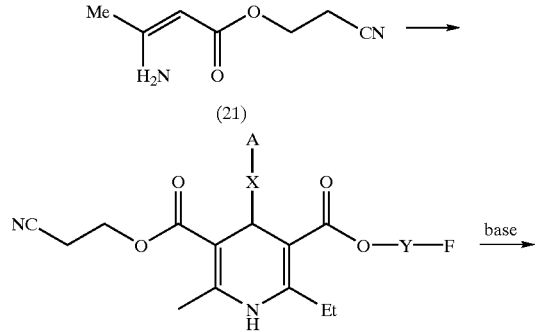

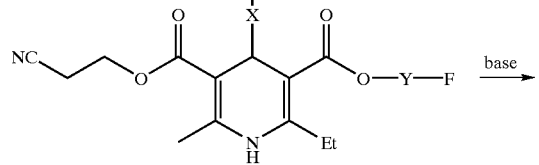

(1-11)

wherein A, F, X and Y are as defined above.

Dihydropyridine derivatives (1-12) wherein C is ethyl group can be produced from, for example, trimethylsilyl 3-oxovaleric ester (47) according to the following flow chart:

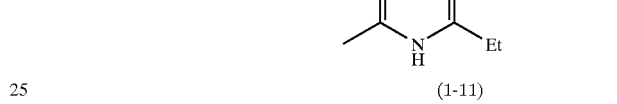

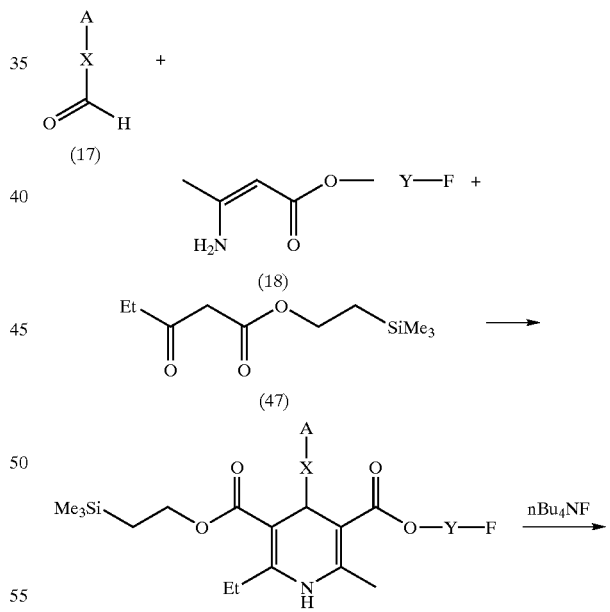

wherein A, F, X and Y are as defined above.

Dihydropyridine derivatives (1-13) wherein E is dimethoxymethyl group can be produced from, for example, ketoesters (49) according to the following flow chart:

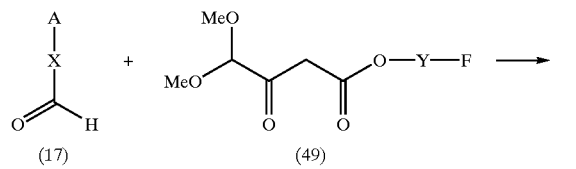

(17)  (49)

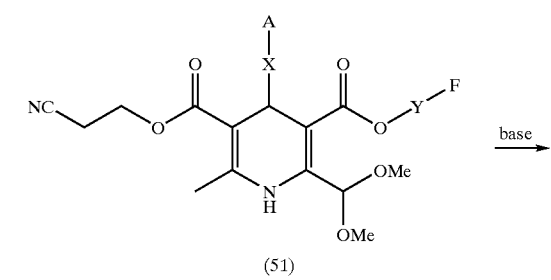

(50)

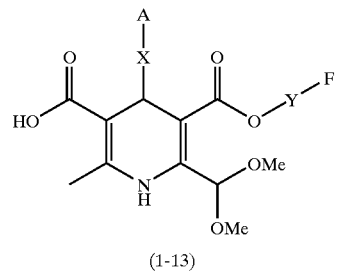

(51)

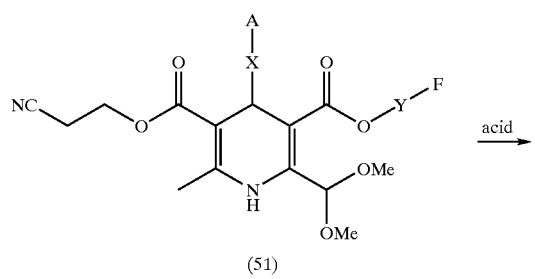

(1-13)

wherein A, F, X and Y are as defined above.

Dihydropyridine derivatives (1-14) wherein E is cyano group can be produced according to the following flow chart. Namely, they can be produced by the acid treatment of dihydropyridine diesters (51) with an acid, followed by the conversion of the product into an oxime, dehydration reaction and hydrolysis.

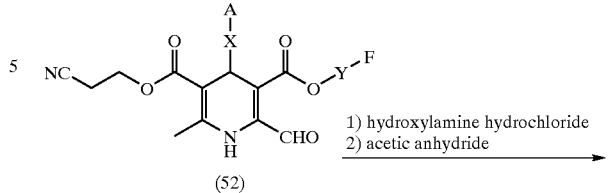

(52)

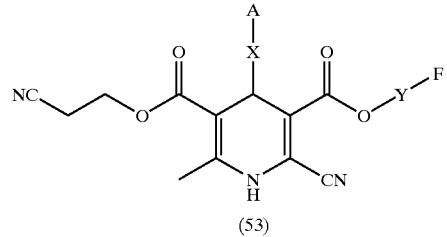

(53)

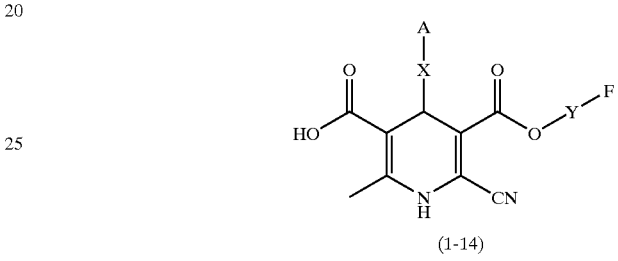

(1-14)

wherein A, F, X and Y are as defined above.

When 3-aminocrotonic esters (18) used as the starting materials are not well-known, they can be produced by, for example, heating an alcohol (26) with a diketene (54) and a suitable base to obtain an acetoacetic ester (20) and then reacting the ester (20) with an amine or ammonium acetate.

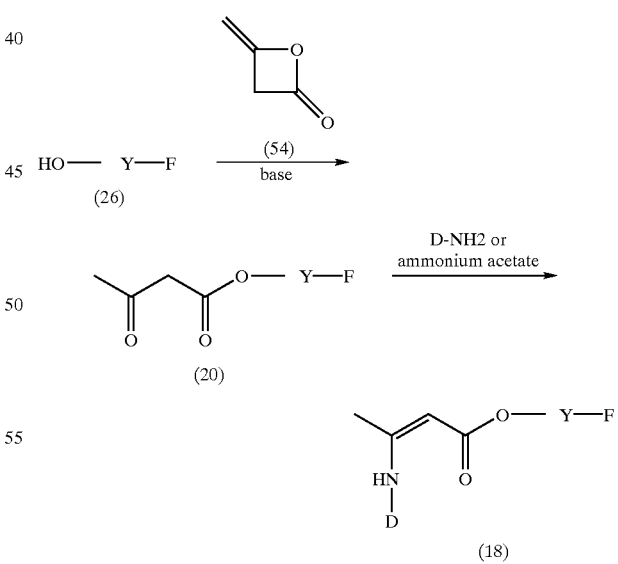

wherein D, F and Y are as defined above.

When the compounds of general formula (1) of the present invention can form salts, the salts must be pharmaceutically acceptable ones. The salts are ammonium salts, salts with alkali metals such as sodium and potassium, salts with alkaline earth metals such as calcium and magnesium, aluminum salts, zinc salts, salts with organic amines such as morpholine and piperidine, and salts with basic amino acids such as arginine and lysine.

The compounds of general formula (1) or salts thereof can be administered as they are or in the form of various medicinal compositions. The forms of the medicinal compositions are, for example, tablets, powders, pills, granules, capsules, suppositories, solutions, sugar-coated tablets and depots. They can be prepared with an ordinary assistants such as carriers and diluents. For example, tablets can be prepared by mixing the dihydropyridine derivative used as the active ingredient of the present invention with a known assistant material such as an inert diluent, e.g. lactose, calcium carbonate or calcium phosphate; a binder, e.g. acacia, corn starch or gelatin; an excipient, e.g. alginic acid, corn starch or pregelatinized starch; a sweetening agent, e.g. sucrose, lactose or saccharin; a flavoring agent, e.g. peppermint, or cherry; and magnesium stearate, talc or carboxymethylcellulose.

The N-type calcium channel antagonists containing one of the compounds of general formula (1) and salts thereof are usable as therapeutic agents for any of encephalopathies caused by the ischemia in the acute phase after the onset of cerebral infarction, cerebral hemorrhage (including subarachnoidal bleeding) or the like; progressive neurodegenerative diseases, e.g. Alzheimer's disease; AIDS related dementia; Parkinson's disease; dementia caused by cerebrovascular disorders and ALS; various pains, e.g. neuropathy caused by head injury; sharp pain caused by spinal injury, diabetes or thromboangitis obliterans; pain after an operation; migraine and visceral various diseases caused by psychogenic stress, e.g. pain; bronchial asthma; unstable angina and hypersensitive colon inflammation; emotional disorder; and drug addiction withdrawal symptoms, e.g. ethanol addiction withdrawal symptoms.

The dosage of the therapeutic agent used for the above-described purpose varies depending on the intended therapeutic effect, method of administration, period of therapy, age, body weight, etc. Usually, it is given to adults in an amount of 1 $\mu$g to 5 g/day in the oral administration, and 0.01 $\mu$g to 1 g/day in the parenteral administration.

The following Examples will further illustrate the preferred embodiments of the present invention, which by no means limit the invention.

EXAMPLE 1

Synthesis of mono(3-phenyl-2-propene-1-yl) 2,6-dimethyl-4-phenyl-1,4-dihydropyridine-3,5-dicarboxylate 1) Synthesis of 5-(3-phenyl-2-propene-1-yl) 3-(2-cyanoethyl) 2,6-dimethyl-1,4-phenyl-1,4-dihydropyridine-3,5-dicarboxylate:

465 mg (3.0 mmol) of 2-cyanoethyl acetoacetate, 654 mg (3.01 mmol) of cinnamyl 3-aminocrotonate and 0.305 ml (3.0 mmol) of benzaldehyde were heated at 70° C. under stirring in 15 ml of 2-propanol overnight. 2-Propanol was evaporated under reduced pressure, and the residue was purified by the silica gel chromatography (hexane/ethyl acetate=2/1) to obtain the title compound.

Yield: 679 mg (1.53 mmol) (51.1%)

MS (ESI, m/z) 443 (M+H)$^+$ $^1$H-NMR (CDCl$_3$): 2.36 (6H, s), 2.59 (2H, t), 4.20–4.32 (2H, m), 4.64–4.80 (2H, m), 5.03 (1H, s), 5.70 (1H, s), 6.23 (1H, dt), 6.50 (1H, d), 7.10–7.37 (10H, m)

2) Synthesis of mono(3-phenyl-2-propene-1-yl) 2,6-dimethyl-4-phenyl-1,4-dihydropyridine-3,5-dicarboxylate:

207 mg (0.47 mmol) of 5-(3-phenyl-2-propene-1-yl) 3-(2-cyanoethyl) 2,6-dimethyl-4-phenyl-1,4-dihydropyridine-3,5-dicarboxylate was dissolved in 4 ml of methanol. 1 ml of 1 N aqueous sodium hydroxide solution was added to the obtained solution, and they were stirred at room temperature for 2 hours. 2 N hydrochloric acid was added to the resultant mixture, and methanol was evaporated under reduced pressure. After the extraction with ethyl acetate, the organic layer was dried over anhydrous sodium sulfate and concentrated under reduced pressure. The residue was washed with hexane/ethyl acetate (1:1) and dried under reduced pressure to obtain the title compound.

Yield: 119 mg (0.31 mmol) (65.3%)

MS (ESI, m/z) 390 (M+H)$^+$ $^1$H-NMR (DMSO-d$_6$): 2.25 (3H, s), 2.29 (3H, s), 4.58–4.76 (2H, m), 4.94 (1H, s), 6.31 (1H, dt), 6.50 (1H, d), 7.06–7.40(10H, m), 8.77 (1H, s), 11.66 (1H, brd)

EXAMPLE 2

Synthesis of mono(3-phenyl-2-propene-1-yl) 2,6-dimethyl-4-(2-nitrophenyl)-1,4-dihydropyridine-3,5-dicarboxylate 1) Synthesis of 5-(3-phenyl-2-propene-1-yl) 3-(2-cyanoethyl) 2,6-dimethyl-4-(2-nitrophenyl)-1,4-dihydropyridine-3,5-dicarboxylate:

The title compound was obtained from 780 mg (5.03 mmol) of 2-cyanoethyl acetoacetate, 1.087 g (5.00 mmol) of cinnamyl 3-aminocrotonate and 755 mg (5.00 mmol) of 2-nitrobenzaldehyde in the same manner as that of Example 1-1).

Yield: 1.41 g (2.89 mmol) (57.7%)

MS (ESI, m/z) 510 (M+Na)$^+$ $^1$H-NMR (CDCl$_3$): 2.35 (3H, s), 2.36 (3H, s), 2.66 (2H, t), 4.09–4.32 (2H, m), 4.59–4.76 (2H, m), 5.71 (1H, s), 5.82 (1H, s), 6.22 (1H, dt), 6.48 (1H, d), 7.20–7.36 (6H, m), 7.43–7.54 (2H, m), 7.70 (1H, d)

2) Synthesis of mono(3-phenyl-2-propene-1-yl) 2,6-dimethyl-4-(2-nitrophenyl)-1,4-dihydropyridine-3,5-dicarboxylate:

894 mg (1.83 mmol) of 5-(3-phenyl-2-propene-1-yl) 3-(2-cyanoethyl) 2,6-dimethyl-4-(2-nitrophenyl)-1,4-dihydropyridine-3,5-dicarboxylate was dissolved in 15 ml of ethanol. 3.5 ml of 1 N aqueous sodium hydroxide solution was added to the resultant solution, and they were stirred at room temperature for 2.5 hours. 2 N hydrochloric acid was added to the resultant mixture. Methanol was evaporated under reduced pressure. After the extraction with ethyl acetate, the organic layer was dried over anhydrous sodium sulfate and concentrated under reduced pressure. The residue was purified by the silica gel chromatography (chloroform/methanol=50/1) to obtain the title compound.

Yield: 459 mg (1.06 mmol) (57.7%)

MS (ESI, m/z) 457 (M+Na)$^+$ $^1$H-NMR (CDCl$_3$): 2.32 (3H, s), 2.35 (3H, s), 4.58–4.74 (2H, m), 5.70 (1H, s), 5.80 (1H, s), 6.18 (1H, dt), 6.43 (1H, d), 7.18–7.32 (6H, m), 7.40–7.53 (2H, m), 7.64 (1H, d)

EXAMPLE 3

Synthesis of mono(3-phenyl-2-propene-1-yl) 4-(3-cyanophenyl)-2,6-dimethyl-1,4-dihydropyridine-3,5-dicarboxylate 1) Synthesis of 5-(3-phenyl-2-propene-1-yl) 3-(2-cyanoethyl) 4-(3-cyanophenyl)-2,6-dimethyl-1,4-dihydropyridine-3,5-dicarboxylate The title compound was obtained from 784 mg (5.05 mmol) of 2-cyanoethyl acetoacetate, 1.083 g (4.98 mmol) of cinnamyl 3-aminocrotonate and 661 mg (5.04 mmol) of 3-cyanobenzaldehyde in the same manner as that of Example 1-1).
Yield: 1.68 g (3.58 mmol) (72.0%)
MS (ESI, m/z) 490 (M+Na)$^+$
$^1$H-NMR (CDCl$_3$): 2.38 (6H, s), 2.62 (2H, t), 4.18–4.31 (2H, m), 4.64–4.79 (2H, m), 5.06 (1H, s), 5.81 (1H, s), 6.22 (1H, dt), 6.54 (1H, d), 7.24–7.38 (6H, m), 7.40–7.45 (1H, m), 7.55–7.62 (2H, m)

2) Synthesis of mono(3-phenyl-2-propene-1-yl) 4-(3-cyanophenyl)-2,6-dimethyl-1,4dihydropyridine-3,5-dicarboxylate:

1.160 g (2.48 mmol) of 5-(3-phenyl-2-propene-1-yl) 3-(2-cyanoethyl) 4-(3-cyanophenyl)-2,6-dimethyl-1,4-dihydropyridine-3,5-dicarboxylate was dissolved in 30 ml of methanol. 5 ml of 1 N aqueous sodium hydroxide solution was added to the resultant solution, and they were stirred at room temperature for 2 hours. 2 N hydrochloric acid was added to the resultant mixture. Methanol was evaporated under reduced pressure. Water was added to the residue, and the solid was taken by the filtration, washed with hexane/ethyl acetate (1:1) and dried under reduced pressure to obtain the title compound.
Yield: 737 mg (1.78 mmol) (71.8%).
MS (ESI, m/z) 413 (M–H)$^-$
$^1$H-NMR (DMSO-d$_6$): 2.27 (3H, s), 2.31 (3H, s), 4.55–4.76 (2H, m), 4.96 (1H, s), 6.31 (1H, dt), 6.50 (1H, d), 7.20–7.62 (9H, m), 8.91 (1H, s), 11.78 (1H, brd)

EXAMPLE 4

Synthesis of mono(3-phenyl-2-propene-1-yl) 4-(3-chlorophenyl)-2,6-dimethyl-1,4-dihydropyridine-3,5-dicarboxylate 1) Synthesis of 5-(3-phenyl-2-propene-1-yl) 3-(2-cyanoethyl) 4-(3-chlorophenyl)-2,6-dimethyl-1,4-dihydropyridine-3,5-dicarboxylate The title compound was obtained from 776 mg (5.0 mmol) of 2-cyanoethyl acetoacetate, 1.086 g (5.0 mmol) of cinnamyl 3-aminocrotonate and 0.566 ml (5.0 mmol) of 3-chlorobenzaldehyde in the same manner as that of Example 1-1).
Yield: 1.514 g (3.18 mmol) (64%)
MS (ESI, m/z) 499 (M+Na)$^+$
$^1$H-NMR (CDCl$_3$): 2.37 (6H, s), 2.61 (2H, t), 4.19–4.33 (2H, m), 4.64–4.80 (2H, m), 5.01 (1H, s), 5.72 (1H, bs), 6.24 (1H, dt), 6.53 (1H, d), 7.11–7.38 (9H, m)

2) Synthesis of mono(3-phenyl-2-propene-1-yl) 4-(3-chlorophenyl)-2,6-dimethyl-1,4-dihydropyridine-3,5-dicarboxylate:

508 mg (1.07 mmol) of 5-(3-phenyl-2-propene-1-yl) 3-(2-cyanoethyl) 4-(3-chlorophenyl)-2,6-dimethyl-1,4-dihydropyridine-3,5-dicarboxylate was dissolved in 10.7 ml of methanol. 2.14 ml of 1 N aqueous sodium hydroxide solution was added to the resultant solution, and they were stirred at room temperature for 13 hours. 2 N hydrochloric acid was added to the resultant mixture. Methanol was evaporated under reduced pressure. After the extraction with ethyl acetate, the organic layer was dried over anhydrous sodium sulfate and then concentrated under reduced pressure. The residue was washed with hexane/ethyl acetate (1:1) and dried under reduced pressure to obtain the title compound.
Yield: 286 mg (0.675 mmol) (63%).
MS (ESI, m/z) 422 (M–H)$^-$
$^1$H-NMR (DMSO-d$_6$): 2.26 (3H, s), 2.30 (3H, s), 4.59–4.77 (2H, m), 4.93 (1H, s), 6.32 (1H, dt), 6.51 (1H, d), 7.10–7.41 (9H, m), 8.85 (1H, s)

EXAMPLE 5

Synthesis of mono(3-phenyl-2-propene-1-yl) 4-(2,3-dichlorophenyl)-2,6-dimethyl-1,4-dihydropyridine-3,5-dicarboxylate 1) Synthesis of 5-(3-phenyl-2-propene-1-yl) 3-(2-cyanoethyl) 4-(2,3-dichlorophenyl)-2,6-dimethyl-1,4-dihydropyridine-3,5-dicarboxylate:

The title compound was obtained from 776 mg (5.0 mmol) of 2-cyanoethyl acetoacetate, 1,086 mg (5.0 mmol) of cinnamyl 3-aminocrotonate and 875 mg (5.0 mmol) of 2,3-dichlorobenzaldehyde in the same manner as that of Example 1-1).
Yield: 1.745 g (3.42 mmol) (68%)
MS (ESI, m/z) 533 (M+Na)$^+$
$^1$H-NMR (CDCl$_3$): 2.33 (6H, s), 2.63 (2H, t), 4.23 (2H, t), 4.62–4.76 (2H, m), 5.48 (1H, s), 5.75 (1H, bs), 6.19 (1H, dt), 6.47 (1H, d), 7.04–7.35 (8H, m)

2) Synthesis of mono(3-phenyl-2-propene-1-yl) 4-(2,3-dichlorophenyl)-2,6-dimethyl-1,4-dihydropyridine-3,5-dicarboxylate:

The title compound was obtained from 556 mg (1.09 mmol) of 5-(3-phenyl-2-propene-1-yl) 3-(2-cyanoethyl) 4-(2,3-dichlorophenyl)-2,6-dimethyl-1,4-dihydropyridine-3,5-dicarboxylate in the same manner as that of Example 4-2).
Yield: 167 mg (0.364 mmol) (33%)
MS (ESI, m/z) 456 (M–H)$^-$
$^1$H-NMR (DMSO-d$_6$): 2.22 (3H, s), 2.25 (3H, s), 4.54–4.70 (2H, m), 5.35 (1H, s), 6.23 (1H, dt), 6.39 (1H, d), 7.20–7.39 (8H, m), 8.82 (1H, s)

EXAMPLE 6

Synthesis of mono(3-phenyl-2-propene-1-yl) 4-(3-trifluoromethylphenyl)-2,6-dimethyl-1,4-dihydropyridine-3,5-dicarboxylate:

1-Synthesis of 5-(3-phenyl-2-propene-1-yl)-3-(2-cyanoethyl) 4 (3-trifluoromethylphenyl)-2,6-dimethyl-1,4-dihydropyridine-3,5—dicarboxylate:

The title compound was obtained from 466 mg (3.0 mmol) of 2-cyanoethyl acetoacetate, 652 mg (3.0 mmol) of cinnamyl 3-aminocrotonate and 522 mg (3.0 mmol) of 3-trifluoromethylbenzaldehyde in the same manner as that of Example 1-1).
Yield: 765 g (1.50 mmol) (50%)
MS (ESI, m/z) 533 (M+Na)$^+$
$^1$H-NMR (CDCl$_3$): 2.38 (6H, s), 2.60 (2H, t), 4.20–4.29 (2H, m), 4.68–4.74 (2H, m), 5.08 (1H, s), 5.75 (1H, bs), 6.22 (1H, dt), 6.53 (1H, d), 7.22–7.54 (9H, m)

2) Synthesis of mono(3-phenyl-2-propene-1-yl) 4-(3-trifluoromethylphenyl)-2,6-dimethyl-1,4-dihydropyridine-3,5-dicarboxylate:

The title compound was obtained from 756 mg (1.48 mmol) of 5-(3-phenyl-2-propene-1-yl) 3-(2-cyanoethyl) 4-(3-trifluoromethylphenyl)-2,6-dimethyl-1,4-dihydropyridine-3,5-dicarboxylate in the same manner as that of Example 4-2).

Yield: 186 mg (0.407 mmol) (27%)
MS (ESI, m/z) 456 (M−H)−
$^1$H-NMR (DMSO-d$_6$): 2.27 (3H, s), 2.31 (3H, s), 4.58–4.74 (2H, m), 5.01 (1H, s), 6.30 (1H, dt), 6.49 (1H, d), 7.25–7.48 (9H, m), 8.90 (1H, s)

EXAMPLE 7

Synthesis of mono(3-phenyl-2-propene-1-yl) 4-(3-fluorophenyl)-2,6-dimethyl-1,4-dihydropyridine-3,5-dicarboxylate 1) Synthesis of 5-(3-phenyl-2-propene-1-yl) 3-(2-cyanoethyl) 4-(3-fluorophenyl)-2,6-dimethyl-1,4-dihydropyridine-3,5-dicarboxylate The title compound was obtained from 578 mg (3.72 mmol) of 2-cyanoethyl acetoacetate, 811 mg (3.73 mmol) of cinnamyl 3-aminocrotonate and 0.39 ml (3.68 mmol) of 3-fluorobenzaldehyde in the same manner as that of Example 1-1).

Yield: 1.162 g (2.52 mmol) (68.6%)
MS (ESI, m/z) 459 (M−H)−
$^1$H-NMR (CDCl$_3$): 2.37 (6H, s), 2.62 (2H, t), 4.20–4.34 (2H, m), 4.65–4.82 (2H, m), 5.04 (1H, s), 5.76 (1H, s), 6.24 (1H, dt, J=16 Hz), 6.53 (1H, d, J=16 Hz), 6.79–6.87 (1H, m), 6.96–7.02 (1H, m), 7.08–7.22 (2H, m), 7.23–7.38 (5H, m)

2) Synthesis of mono(3-phenyl-2-propene-1-yl) 4-(3-fluorophenyl)-2,6-dimethyl-1,4-dihydropyridine-3,5-dicarboxylate:

The title compound was obtained from 1.162 g (2.52 mmol) of 5-(3-phenyl-2-propene-1-yl) 3-(2-cyanoethyl) 4-(3-fluorophenyl)-2,6-dimethyl-1,4-dihydropyridine-3,5-dicarboxylate in the same manner as that of Example 3-2).

Yield: 858 mg (2.11 mmol) (83.6%)
MS (ESI, m/z) 406 (M−H)−
$^1$H-NMR (DMSO-d$_6$): 2.26 (3H, s), 2.30 (3H, s), 4.59–4.78 (2H, m), 4.96 (1H, s), 6.33 (1H, dt, J=16 Hz), 6.51 (1H, d, J=16 Hz), 6.87–7.06 (3H, m), 7.21–7.44 (6H, m), 8.87 (1H, s)

EXAMPLE 8

Synthesis of (3-phenyl-2-propene-1-yl) 5-carbamoyl-4-(3-chlorophenyl)-2,6-dimethyl-1,4-dihydropyridine-3-carboxylate The title compound was obtained by heating 653 mg (3.01 mmol) of cinnamyl 3-aminocrotonate, 315 mg (9.96 mmol) of acetoacetamide and 0.34 ml (3.00 mmol) of 3-chlorobenzaldehyde in 15 ml of 2-propanol at 80° C. under stirring for 2 days. 2-Propanol was evaporated under reduced pressure, and the residue was purified by the silica chromatography (chloroform/methanol=50/1).

Yield: 129 mg (0.31 mmol) (10.2%)
MS(ESI, m/z) 421 (M−H)−
$^1$H-NMR (DMSO-d$_6$): 2.07 (3H, s), 2.28 (3H, s), 4.54–4.74 (2H, m), 4.89 (1H, s) 6.27 (1H, dt, J=16 Hz), 6.46 (1H, d, J=16 Hz), 6.88 (2H, brd), 7.12–7.20 (3H, m), 7.21–7.40 (6H, m), 8.44 (1H, s)

EXAMPLE 9

Synthesis of (3-phenyl-2-propene-1-yl) 4-(3-chlorophenyl)-5-cyano-2,6-dimethyl-1,4-dihydropyridine-3-carboxylate The title compound was obtained by heating 2.198 g (10.1 mmol) of cinnamyl acetoacetate, 818 mg (9.96 mmol) of 3-aminocrotonitrile and 1.15 ml (10.2 mmol) of 3-chlorobenzaldehyde at 80° C. in 40 ml of 2-propanol under stirring for 2 days. 2-Propanol was evaporated under reduced pressure, and the residue was purified by the silica gel chromatography (hexane/ethyl acetate=2/1).

Yield: 2.664 g (6.58 mmol) (66.1%)
MS (ESI, m/z) 403 (M−H)−
$^1$H-NMR (CDCl$_3$): 2.10 (3H, s), 2.39 (3H, s), 4.56–4.74 (3H, m), 5.82 (1H, s), 6.09 (1H, dt, J=16 Hz), 6.44 (1H, d, J=16 Hz), 7.14–7.33 (9H, m)

EXAMPLE 10

Synthesis of mono(3-phenyl-2-propene-1-yl) 4-(3-bromophenyl)-2,6-dimethyl-1,4-dihydropyridine-3,5-dicarboxylate 1) Synthesis of 5-(3-phenyl-2-propene-1-yl) 3-(2-cyanoethyl) 4-(3-bromophenyl)-2,6-dimethyl-1,4-dihydropyridine-3,5-dicarboxylate The title compound was obtained from 466 mg (3.0 mmol) of 2-cyanoethyl acetoacetate, 652 mg (3.0 mmol) of cinnamyl 3-aminocrotonate and 555 mg (3.0 mmol) of 3-bromobenzaldehyde in the same manner as that of Example 1-1)

Yield: 1.08 g (2.07 mmol) (50%)
MS (ESI, m/z) 545 (M+Na)+
$^1$H-NMR (CDCl$_3$): 2.37 (6H, s), 2.61 (2H, t), 4.19–4.33 (2H, m), 4.64–4.80 (2H, m), 5.01 (1H, s), 5.72 (1H, bs), 6.24 (1H, dt), 6.53 (1H, d), 7.07 (1H, t), 7.22–7.42 (8H, m)

2) Synthesis of mono(3-phenyl-2-propene-1-yl) 4-(3-bromophenyl)-2,6-dimethyl-1,4-dihydropyridine-3,5-dicarboxylate:

The title compound was obtained from 1.05 g (2.01 mmol) of 5-(3-phenyl-2-propene-1-yl) 3-(2-cyanoethyl) 4-(3-bromophenyl)-2,6-dimethyl-1,4-dihydropyridine-3,5-dicarboxylate in the same manner as that of Example 4-2).

Yield: 755 mg (1.61 mmol) (80%)
MS (ESI, m/z) 466 (M−H)−
$^1$H-NMR (DMSO-d$_6$): 2.26 (3H, s), 2.30 (3H, s), 4.58–4.77 (2H, m), 4.93 (1H, s), 6.32 (1H, dt), 6.51 (1H, d), 7.16–7.41 (9H, m), 8.83 (1H, bs)

EXAMPLE 11

Synthesis of mono(3-phenyl-2-propene-1-yl) 4-(3-iodophenyl)-2,6-dimethyl-1,4-dihydropyridine-3,5-dicarboxylate 1) Synthesis of 5-(3-phenyl-2-propene-1-yl) 3-(2-cyanoethyl) 4-(3-iodophenyl)-2,6-dimethyl-1,4-dihydropyridine-3,5-dicarboxylate:

The title compound was obtained from 466 mg (3.0 mmol) of 2-cyanoethyl acetoacetate, 652 mg (3.0 mmol) of cinnamyl 3-aminocrotonate and 696 mg (3.0 mmol) of 3-iodobenzaldehyde in the same manner as that of Example 1-1).

Yield: 1.14 g (2.01 mmol) (67%)

$^1$H-NMR (CDCl$_3$): 2.37 (6H, s), 2.61 (2H, t), 4.19–4.33 (2H, m), 4.64–4.80 (2H, m), 4.98 (1H, s), 5.72 (1H, bs), 6.24 (1H, dt), 6.53 (1H, d), 6.94 (1H, t), 7.24–7.62 (8H, m)

2) Synthesis of mono(3-phenyl-2-propene-1-yl) 4-(3-iodophenyl)-2,6-dimethyl-1,4-dihydropyridine-3,5-dicarboxylate:

The title compound was obtained from 1.14 g (2.01 mmol) of 5-(3-phenyl-2-propene-1-yl) 3-(2-cyanoethyl) 4-(3-iodophenyl)-2,6-dimethyl-1,4-dihydropyridine-3,5-dicarboxylate in the same manner as that of Example 4-2).

Yield: 903 mg (1.75 mmol) (87%)

MS (ESI, m/z) 514 (M–H)$^-$ $^1$H-NMR (DMSO-d$_6$): 2.25 (3H, s), 2.29 (3H, s), 4.58–4.76 (2H, m), 4.88 (1H, s), 6.32 (1H, dt), 6.51 (1H, d), 7.03 (1H, t), 7.16–7.54 (8H, m), 8.84 (1H, bs)

EXAMPLE 12

Synthesis of mono(3-phenyl-2-propyne-1-yl) 4-(3-chlorophenyl)-2,6-dimethyl-1,4-dihydropyridine-3,5-dicarboxylate 1) Synthesis of 5-(3-phenyl-2-propyne-1-yl) 3-(2-cyanoethyl) 4-(3-chlorophenyl)-2,6-dimethyl-1,4-dihydropyridine-3,5-dicarboxylate:

The title compound was obtained from 309 mg (2.0 mmol) of 2-cyanoethyl 3-aminocrotonate, 433 mg (2.0 mmol) of 3-phenyl-2-propyne-1-yl acetoacetate and 0.227 ml (2.0 mmol) of 3-chlorobenzaldehyde in the same manner as that of Example 1-1).

Yield: 641 mg (1.35 mmol) (68%)

MS (ESI, m/z) 497 (M+Na)$^+$ $^1$H-NMR (CDCl$_3$): 2.38 (6H, s), 2.61 (2H, t), 4.19–4.34 (2H, m), 4.86 (1H, d), 4.92 (1H, d), 5.02 (1H, s), 5.74 (1H, bs), 7.10–7.46 (9H, m)

2) Synthesis of mono(3-phenyl-2-propyne-1-yl) 4-(3-chlorophenyl)-2,6-dimethyl-1,4-dihydropyridine-3,5-dicarboxylate:

The title compound was obtained from 641 mg (1.35 mmol) of 5-(3-phenyl-2-propyne-1-yl) 3-(2-cyanoethyl) 4-(3-chlorophenyl)-2,6-dimethyl-1,4-dihydropyridine-3,5-dicarboxylate in the same manner as that of Example 4-2).

Yield: 277 mg (0.657 mmol) (49%)

MS (ESI, m/z) 420 (M–H)$^-$ $^1$H-NMR (DMSO-d$_6$): 2.27 (3H, s), 2.29 (3H, s), 4.89 (1H, s), 4.92 (2H, s), 7.12–7.23 (4H, m), 7.38–7.43 (5H, m), 8.85 (1H, bs)

EXAMPLE 13

Synthesis of mono(3-(4-chlorophenyl)-2-propene-1-yl) 4-(3-chlorophenyl)-2,6-dimethyl-1,4-dihydropyridine-3,5-dicarboxylate 1) Synthesis of 5-(3-(4-chlorophenyl)-2-propene-1-yl) 3-(2-cyanoethyl) 4-(3-chlorophenyl)-2,6-dimethyl-1,4-dihydropyridine-3,5-dicarboxylate:

The title compound was obtained from 309 mg (2.0 mmol) of 2-cyanoethyl 3-aminocrotonate, 505 mg (2.0 mmol) of 3-(4-chlorophenyl)-2-propene-1-yl acetoacetate and 0.227 ml (2.0 mmol) of 3-chlorobenzaldehyde in the same manner as that of Example 1-1).

Yield: 681 mg (1.33 mmol) (67%)

MS (ESI, m/z) 533 (M+Na)$^+$ $^1$H-NMR-(CDCl$_3$): 2.35(6H, s), 2.60 (2H, t), 4.20–4.27 (2H, m), 4.59–4.79 (2H, m), 4.99 (1H, s), 5.71 (1H, bs), 6.18 (1H, dt), 6.42 (1H, d), 7.08–7.26 (8H, m)

2) Synthesis of mono(3-(4-chlorophenyl)-2-propene-1-yl) 4-(3-chlorophenyl)-2,6-dimethyl-1,4-dihydropyridine-3,5-dicarboxylate:

The title compound was obtained from 681 mg (1.33 mmol) of 5-(3-(4-chlorophenyl)-2-propene-1-yl) 3-(2-cyanoethyl) 4-(3-chlorophenyl)-2,6-dimethyl-1,4-dihydropyridine-3,5-dicarboxylate in the same manner as that of Example 4-2).

Yield: 331 mg (0.721 mmol) (54%)

MS (ESI, m/z) 456 (M–H)$^-$ $^1$H-NMR (DMSO-d$_6$): 2.25 (3H, s), 2.30 (3H, s), 4.58–4.77 (2H, m), 4.93 (1H, s), 6.35 (1H, dt), 6.48 (1H, d), 7.11–7.44 (8H, m), 8.84 (1H, bs)

EXAMPLE 14

Synthesis of mono(phenylcarbamoylmethyl) 4-(3-chlorophenyl)-2,6-dimethyl-1,4-dihydropyridine-3,5-dicarboxylate 1) Synthesis of phenylcarbamoylmethyl acetoacetate:

4.36 g (28.8 mmol)) of 2-hydroxy-N-phenylacetamide, 0.8 ml (5.74 mmol) of triethylamine and 6.5 ml (84.3 mmol) of diketene were heated at 70° C. under stirring in 50 ml of toluene for 7.5 hours. After the addition of a saturated aqueous sodium hydrogencarbonate solution at room temperature followed by the extraction with ethyl acetate, the organic layer was dried over anhydrous sodium sulfate and then concentrated under reduced pressure to obtain the title compound.

Yield: 6.27 g (26.7 mmol) (92.5%)

MS (ESI, m/z) 234 (M–H)$^-$ $^1$H-NMR (CDCl$_3$): 2.38 (3H, s), 3.73 (2H, s), 4.83 (2H, s), 7.13 (1H, t), 7.35 (2H, t), 7.79 (2H, d), 9.14 (1H, brd)

2) Synthesis of 5-(phenylcarbamoylmethyl) 3-(2-cyanoethyl) 4-(3-chlorophenyl)-2,6-dimethyl-1,4-dihydropyridine-3,5-dicarboxylate:

The title compound was obtained from 487 mg (3.16 mmol) of 2-cyanoethyl 3-aminocrotonate, 745 mg (3.17 mmol) of phenylcarbamoylmethyl acetoacetate and 0.36 ml (3.18 mmol) of 3-chlorobenzaldehyde in the same manner as that of Example 1-1).

Yield: 1.023 g (2.07 mmol) (65.5%)

MS (ESI, m/z) 492 (M–H)$^-$ $^1$H-NMR (CDCl$_3$): 2.36 (3H, s), 2.46 (3H, s), 2.68 (2H, t), 4.24–4.39 (2H, m), 4.48 (1H, d), 4.92 (1H, d), 5.08 (1H, s), 6.01 (1H, s), 7.08–7.23 (5H, m), 7.26–7.33 (4H, m)

3) Synthesis of mono(phenylcarbamoylmethyl) 4-(3-chlorophenyl)-2,6-dimethyl-1,4-dihydropyridine-3,5-dicarboxylate:

The title compound was obtained from 752 mg (1.52 mmol) of 5-phenylcarbamoylmethyl 3-(2-cyanoethyl) 4-(3-chlorophenyl)-2,6-dimethyl-1,4-dihydropyridine-3,5-dicarboxylate in the same manner as that of Example 3-2).

Yield: 305 mg (0.69 mmol) (45.5%)

MS (ESI, m/z) 439 (M–H)$^-$ $^1$H-NMR (DMSO-d$_6$): 2.29 (3H, s), 2.30 (3H, s), 4.63 (2H, d), 4.96 (1H, s), 7.02–7.34 (7H, m), 7.55 (2H, d), 8.93 (1H, s), 10.04 (1H, s)

EXAMPLE 15

Synthesis of mono(3-(4-methoxyphenyl)-2-propene-1-yl) 4-(3-chlorophenyl)-2,6-dimethyl-1,4-dihydropyridine-3,5-dicarboxylate 1) Synthesis of 5-(3-(4-methoxyphenyl)-2-propene-1-yl) 3-(2-cyanoethyl) 4-(3-chlorophenyl)-2,6-dimethyl-1,4-dihydropyridine-3,5-dicarboxylate:

The title compound was obtained from 510 mg (3.29 mmol) of 2-cyanoethyl 3-aminocrotonate, 809 mg (3.26 mmol) of 3-(4-methoxyphenyl)-2-propene-1-yl acetoacetate and 0.37 ml (3.27 mmol) of 3-chlorobenzaldehyde in the same manner as that of Example 1-1).

Yield: 511 mg (1.01 mmol) (30.9%)
MS (ESI, m/z) 505 (M–H)$^-$
$^1$H-NMR (CDCl$_3$): 2.36 (3H, s), 2.37 (3H, s), 2.61 (2H, t), 3.81 (3H, s), 4.19–4.33 (2H, m), 4.62–4.78 (2H, m), 5.00 (1H, s), 5.73 (1H, s), 6.11 (1H, dt, J=16 Hz), 6.49 (1H, d, J=16 Hz), 6.85 (2H, d), 7.09–7.23 (4H, m), 7.30 (2H, d)

2) Synthesis of mono(3-(4-methoxyphenyl)-2-propene-1-yl) 4-(3-chlorophenyl)-2,6-dimethyl-1,4-dihydropyridine-3,5-dicarboxylate:

The title compound was obtained from 447 mg (0.88 mmol) of 5-(3-(4-methoxyphenyl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 270 mg (0.59 mmol) (67.6%)
MS (ESI, m/z) 452 (M–H)$^-$
$^1$H-NMR (DMSO-d$_6$): 2.26 (3H, s), 2.29 (3H, s), 3.75 (3H, s), 4.54–4.73 (2H, m), 4.91 (1H, s), 6.16 (1H, dt, J=16 Hz), 6.47 (1H, d, J=16 Hz), 6.89 (2H, d), 7.09–7.27 (4H, m), 7.33 (2H, d), 8.85 (1H, s)

EXAMPLE 16

Synthesis of mono(2-methyl-3-phenyl-2-propene-1-yl) 4-(3-chlorophenyl)-2,6-dimethyl-1,4-dihydropyridine-3,5-dicarboxylate 1) Synthesis of 5-(2-methyl-3-phenyl-2-propene-1-yl) 3-(2-cyanoethyl) 4-(3-chlorophenyl)-2,6-dimethyl-1,4-dihydropyridine-3,5-dicarboxylate:

The title compound was obtained from 600 mg (3.89 mmol) of 2-cyanoethyl 3-aminocrotonate, 900 mg (3.87 mmol) of 2-methyl-3-phenyl-2-propene-1-yl acetoacetate and 0.44 ml (3.88 mmol) of 3-chlorobenzaldehyde in the same manner as that of Example 1-1).

Yield: 1.195 mg (2.43 mmol) (62.8%)
MS (ESI, m/z) 489 (M–H)$^-$
$^1$H-NMR (CDCl$_3$): 1.81 (3H, s), 2.37 (3H, s), 2.39 (3H, s), 2.62 (2H, t), 4.22–4.32 (2H, m), 4.62 (2H, qua), 5.02 (1H, s), 5.73 (1H, s), 6.41 (1H, s), 7.11–7.37 (9H, m)

2) Synthesis of mono(2-methyl-3-phenyl-2-propene-1-yl) 4-(3-chlorophenyl)-2,6-dimethyl-1,4-dihydropyridine-3,5-dicarboxylate:

The title compound was obtained from 801 mg (1.63 mmol) of 5-(2-methyl-3-phenyl-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 515 mg (1.18 mmol) (72.1%)
MS (ESI, m/z) 436 (M–H)$^-$
$^1$H-NMR (DMSO-d$_6$): 1.73 (3H, s), 2.25 (3H, s), 2.33 (3H, s), 4.47–4.68 (2H, m), 4.94 (1H, s), 6.38 (1H, s), 7.12–7.31 (7H, m), 7.35 (2H, t), 8.89 (1H, s)

EXAMPLE 17

Synthesis of mono(3-(3,4-dichlorophenyl)-2-propene-1-yl) 4-(3-chlorophenyl)-2,6-dimethyl-1,4-dihydropyridine-3,5-dicarboxylate 1) Synthesis of 5-(3-(3,4-dichlorophenyl)-2-propene-1-yl) 3-(2-cyanoethyl) 4-(3-chlorophenyl)-2,6-dimethyl-1,4-dihydropyridine-3,5-dicarboxylate:

The title compound was obtained from 309 mg (2.0 mmol) of 2-cyanoethyl 3-aminocrotonate, 575 mg (2.0 mmol) of 3-(3,4-dichlorophenyl)-2-propene-1-yl acetoacetate and 0.227 ml (2.0 mmol) of 3-chlorobenzaldehyde in the same manner as that of Example 1-1).

Yield: 503 mg (0.922 mmol) (46%)
MS (ESI, m/z) 543 (M–H)$^-$
$^1$H-NMR (CDCl$^3$): 2.37 (6H, s), 2.63 (2H, t), 4.23–4.30 (2H, m), 4.61–4.81 (2H, m), 5.01 (1H, s), 5.78 (1H, bs), 6.20 (1H, dt), 6.34 (1H, d), 7.10–7.23 (5H, m), 7.35–7.40 (2H, m)

2) Synthesis of mono(3-(3,4-dichlorophenyl)-2-propene-1-yl) 4-(3-chlorophenyl)-2,6-dimethyl-1,4-dihydropyridine-3,5-dicarboxylate:

The title compound was obtained from 503 mg (0.601 mmol) of 5-(3-(3,4-dichlorophenyl)-2-propene-1-yl) 3-(2-cyanoethyl) 4-(3-chlorophenyl)-2,6-dimethyl-1,4-dihydropyridine-3,5-dicarboxylate in the same manner as that of Example 4-2).

Yield: 296 mg (0.601 mmol) (65%)
MS(ESI, m/z) 490 (M–H)$^-$
$^1$H-NMR (DMSO-d$_6$): 2.25 (3H, s), 2.30 (3H, s), 4.58–4.77 (2H, m), 4.93 (1H, s), 6.37–6.51 (2H, m), 7.11–7.41 (5H, m), 7.56–7.64 (2H, m), 8.85 (1H, bs)

EXAMPLE 18

Synthesis of mono(3-(4-methylphenyl)-2-propene-1-yl) 4-(3-chlorophenyl)-2,6-dimethyl-1,4-dihydropyridine-3,5-dicarboxylate 1) Synthesis of 5-(3-(4-methylphenyl)-2-propene-1-yl) 3-(2-cyanoethyl) 4-(3-chlorophenyl)-2,6-dimethyl-1,4-dihydropyridine-3,5-dicarboxylate:

The title compound was obtained from 309 mg (2.0 mmol) of 2-cyanoethyl 3-aminocrotonate, 465 mg (2.0 mmol) of 3-(4-methylphenyl)-2-propene-1-yl acetoacetate and 0.227 ml (2.0 mmol) of 3-chlorobenzaldehyde in the same manner as that of Example 1-1).

Yield: 603 mg (1.23 mmol) (62%)
MS (ESI, m/z) 489 (M–H)$^-$
$^1$H-NMR (CDCl$_3$): 2.04 (3H, s), 2.34 (3H, s), 2.39 (3H, s), 2.61 (2H, t), 4.21–4.33 (2H, m), 4.63–4.78 (2H, m), 5.00 (1H, s), 5.74 (1H, s), 6.19 (1H, dt), 6.51 (1H, d), 7.10–7.28 (8H, m)

2) Synthesis of mono(3-(4-methylphenyl)-2-propene-1-yl) 4-(3-chlorophenyl)-2,6-dimethyl-1,4-dihydropyridine-3,5-dicarboxylate:

The title compound was obtained from 603 mg (1.23 mmol) of 5-(3-(4-methylphenyl)-2-propene-1-yl) 3-(2-cyanoethyl) 4-(3-chlorophenyl)-2,6-dimethyl-1,4-dihydropyridine-3,5-dicarboxylate in the same manner as that of Example 4-2).

Yield: 33 mg (0.076 mmol) (6%)
MS (ESI, m/z) 436 (M–H)$^-$
$^1$H-NMR (DMSO-d$_6$): 2.25 (3H, s), 2.28 (3H, s), 2.29 (3H, s), 4.57–4.74 (2H, m), 4.93 (1H, s), 6.24 (1H, dt), 6.47 (1H, d), 7.10–7.30 (8H, m), 8.81 (1H, bs)

EXAMPLE 19

Synthesis of mono(3-phenyl-2-propene-1-yl) 4-(3-chlorophenyl)-1,2,6-trimethyl-1,4-dihydropyridine-3,5-dicarboxylate 1) Synthesis of 3-(2-trimethylsilylethyl) 4-(3-chlorophenyl)-2,6-dimethyl-1,4-dihydropyridine-3,5-dicarboxylate:

The title compound was obtained from 1.04 g (5.13 mmol) of 2-trimethylsilylethyl acetoacetate, 1.11 g (5.11 mmol) of cinnamyl 3-aminocrotonate and 0.58 ml (5.12 mmol) of 3-chlorobenzaldehyde in the same manner as that of Example 1-1).

Yield: 995 mg (1.90 mmol) (37.2%)

MS (ESI, m/z) 522 (M–H)⁻

$^1$H-NMR (CDCl$_3$): 0.01 (9H, s), 0.92–1.02 (2H, m), 2.35 (3H, s), 2.37 (3H, s), 4.08–4.18 (2H, m), 4.63–4.82 (2H, m), 5.04 (1H, s), 5.60 (1H, s), 6.23 (1H, dt, J=16 Hz), 6.53 (1H, d, J=16 Hz), 7.08–7.43 (9H, m)

2) Synthesis of 5-(3-phenyl-2-propene-1-yl) 3-(2-trimethylsilylethyl) 4-(3-chlorophenyl)-1,2,6-trimethyl-1,4-dihydropyridine-3,5-dicarboxylate:

277 mg (0.53 mmol) of 5-(3-phenyl-2-propene-1-yl) 3-(2-trimethylsilylethyl) 4-(3-chlorophenyl)-2,6-dimethyl-1,4-dihydropyridine-3,5-dicarboxylate was dissolved in N,N-dimethylformamide. 40 mg (1.0 mmol) of sodium hydride (60%, oily) was added to the obtained solution. Then 0.05 ml (0.8 mmol) of methyl iodide was added to the resultant mixture, and they were stirred at room temperature for 2 hours. N,N-dimethylformamide was evaporated under reduced pressure. Water was added to the residue. After the extraction with ethyl acetate, the organic layer was dried over anhydrous sodium sulfate and then concentrated under reduced pressure. The residue was purified by the silica gel chromatography (hexane/ethyl acetate=3/1) to obtain the title compound.

Yield: 166 mg (0.31 mmol) (58.2%)

MS (ESI, m/z) 538 (M+H)⁺

$^1$H-NMR (CDCl$_3$): 0.01 (9H, s), 0.97–1.04 (2H, m), 2.48 (3H, s), 2.51 (3H, s), 3.19 (3H, s), 4.14–4.26 (2H, m), 4.71–4.88 (2H, m), 5.21 (1H, s), 6.28 (1H, dt, J=16 Hz), 6.58 (1H, d, J=16 Hz), 7.04–7.18 (4H, m), 7.22–7.39 (5H, m)

3) Synthesis of mono(3-phenyl-2-propene-1-yl) 4-(3-chlorophenyl)-1,2,6-trimethyl-1,4-dihydropyridine-3,5-dicarboxylate:

160 mg (0.30 mmol) of 5-(3-phenyl-2-propene-1-yl) 4-(3-chlorophenyl)-1,2,6-trimethyl-1,4-dihydropyridine-3,5-dicarboxylate was dissolved in 1.5 ml of tetrahydrofuran. 1.5 ml of tetrabutylammonium fluoride (1 N solution in tetrahydrofuran) was added to the resultant solution, and they were stirred at room temperature for 1.5 hours. Ethyl acetate was added to the reaction mixture. The obtained mixture was washed with 1 N hydrochloric acid and a saturated aqueous sodium chloride solution. The organic layer was dried over anhydrous sodium sulfate and then concentrated under reduced pressure. The residue was purified by the silica gel chromatography (hexane/ethyl acetate=2/1) to obtain the title compound.

Yield: 50 mg (0.11 mmol) (38.3%)

MS (ESI, m/z) 436 (M–H)⁻$^P$ $^1$H-NMR (CDCl$_3$): 2.51 (6H, s), 3.19 (3H, s), 4.70–4.88 (2H, m), 5.23 (1H, s), 6.28 (1H, dt, J=16 Hz), 6.58 (1H, d, J=16 Hz), 7.06–7.17 (4H, m), 7.19–7.39 (5H, m)

EXAMPLE 20

Synthesis of mono(3-phenyl-2-propene-1-yl) 4-(3-methoxyphenyl)-2,6-dimethyl-1,4-dihydropyridine-3,5-dicarboxylate 1) Synthesis of 5-(3-phenyl-2-propene-1-yl) 3-(2-cyanoethyl) 4-(3-methoxyphenyl)-2,6-dimethyl-1,4-dihydropyridine-3,5-dicarboxylate:

The title compound was obtained from 466 mg (3.01 mmol) of 2-cyanoethyl acetoacetate, 660 mg (3.04 mmol) of cinnamyl-3-aminocrotonate and 0.365 ml (3.0 mmol) of 3-methoxybenzaldehyde in the same manner as that of Example 1-1).

Yield: 627 mg (1.33 mmol) (44.2%)

MS (ESI, m/z) 471 (M–H)⁻

$^1$H-NMR (CDCl$_3$): 2.35 (3H, s), 2.36 (3H, s), 2.61 (2H, t), 3.71 (3H, s), 4.23–4.30 (2H, m), 4.64–4.83 (2H, m), 5.02 (1H, s), 5.70 (1H, s), 6.25 (1H, dt, J=16 Hz), 6.52 (1H, d, J=16 Hz), 6.69 (1H, dd), 6.85–6.93 (2H, m), 7.14 (1H, t), 7.24–7.38 (5H, m)

2) Synthesis of mono(3-phenyl-2-propene-1-yl) 4-(3-methoxyphenyl)-2,6-dimethyl-1,4-dihydropyridine-3,5-dicarboxylate:

The title compound was obtained from 460 mg (0.97 mmol) of 5-(3-phenyl-2-propene-1-yl) 3-(2-cyanoethyl) 4-(3-methoxyphenyl)-2,6-dimethyl-1,4-dihydropyridine-3,5-dicarboxylate in the same manner as that of Example 3-2).

Yield: 230 mg (0.55 mmol) (56.5%)

MS (ESI, m/z) 418 (M–H)⁻

$^1$H-NMR (DMSO-d$_6$): 2.25 (3H, s), 2.29 (3H, s), 4.58–4.78 (2H, m), 4.93 (1H, s), 6.32 (1H, dt, J=16 Hz), 6.50 (1H, d, J=16 Hz), 6.67–6.80 (3H, m), 7.12 (1H, t), 7.23–7.42 (5H, m), 8.78 (1H, s)

EXAMPLE 21

Synthesis of mono(3-phenyl-2-propene-1-yl) 4-(3,4-dichlorophenyl)-2,6-dimethyl-1,4-dihydropyridine-3,5-dicarboxylate 1) Synthesis of 5-(3-phenyl-2-propene-1-yl) 3-(2-cyanoethyl) 4-(3,4-dichlorophenyl)-2,6-dimethyl-1,4-dihydropyridine-3,5-dicarboxylate:

The title compound was obtained from 465 mg (3.0 mmol) of 2-cyanoethyl acetoacetate, 654 mg (3.01 mmol) of cinnamyl-3-aminocrotonate and 535 mg (3.06 mmol) of 3,4-dichlorobenzaldehyde in the same manner as that of Example 1-1).

Yield: 926 mg (1.81 mmol) (60.4%)

MS (ESI, m/z) 509 (M–H)⁻

$^1$H-NMR (CDCl$_3$): 2.37 (6H, s), 2.63 (2H, t), 4.26 (2H, dt), 4.64–4.82 (2H, m), 4.99 (1H, s), 5.74 (1H, s), 6.23 (1H, dt, J=16 Hz), 6.53 (1H, d, J=16 Hz), 7.17 (1H, dd), 7.25–7.38 (7H, m)

2) Synthesis of mono(3-phenyl-2-propene-1-yl) 4-(3,4-dichlorophenyl)-2,6-dimethyl-1,4-dihydropyridine-3,5-dicarboxylate:

The title compound was obtained from 720 mg (1.41 mmol) of 5-(3-phenyl-2-propene-1-yl) 3-(2-cyanoethyl) 4-(3,4-dichlorophenyl)-2,6-dimethyl-1,4-dihydropyridine-3,5-dicarboxylate in the same manner as that of Example 3-2).

Yield: 476 mg (1.04 mmol) (73.7%)

MS (ESI, m/z) 456 (M–H)⁻

$^1$H-NMR (DMSO-d$_6$): 2.26 (3H, s), 2.30 (3H, s), 4.58–4.78 (2H, m), 4.92 (1H, s), 6.31 (1H, dt, J=16 Hz), 6.46 (1H, d, J=16 Hz), 7.16 (1H, dd), 7.22–7.40 (6H, m), 7.48 (1H, d), 8.90 (1H, s)

EXAMPLE 22

Synthesis of mono(3-phenyl-2-propene-1-yl) 2,6-dimethyl-4-(3-methylphenyl)-1,4-dihydropyridine-3,5-dicarboxylate 1) Synthesis of 5-(3-phenyl-2-propene-1-yl) 3-(2-cyanoethyl) 2,6-dimethyl-4-(3-methylphenyl)-1,4-dihydropyridine-3,5-dicarboxylate:

The title compound was obtained from 467 mg (3.01 mmol) of 2-cyanoethyl acetoacetate, 650 mg (2.99 mmol) of cinnamyl-3-aminocrotonate and 0.36 ml (3.05 mmol) of 3-methoxybenzaldehyde in the same manner as that of Example 1-1).
Yield: 579 mg (1.27 mmol) (42.4%)
MS (ESI, m/z) 455 (M−H)⁻
$^1$H-NMR (CDCl$_3$): 2.25 (3H, s), 2.36 (6H, s), 2.60 (2H, t), 4.21–4.33 (2H, m), 4.64–4.82 (2H, m), 4.99 (1H, s), 5.70 (1H, s), 6.24 (1H, dt, J=16 Hz), 6.51 (1H, d, J=16 Hz), 6.93–6.97 (1H, m), 7.08–7.12 (2H, m), 7.22–7.36 (6H, m)

2) Synthesis of mono(3-phenyl-2-propene-1-yl) 2,6-dimethyl-4-(3-methylphenyl)-1,4-dihydropyridine-3,5-dicarboxylate:

The title compound was obtained from 519 mg (1.14 mmol) of 5-(3-phenyl-2-propene-1-yl) 3-(2-cyanoethyl) 2,6-dimethyl-4-(3-methylphenyl)-1,4-dihydropyridine-3,5-dicarboxylate in the same manner as that of Example 3-2).
Yield: 310 mg (0.77 mmol) (67.6%)
MS (ESI, m/z) 402 (M−H)⁻
$^1$H-NMR (DMSO-d$_6$): 2.17 (3H, s), 2.25 (3H, s), 2.28 (3H, s), 4.57–4.77 (2H, m), 4.91 (1H, s), 6.32 (1H, dt, J=16 Hz), 6.51 (1H, d, J=16 Hz), 6.88–7.00 (3H, m), 7.08 (1H, t), 7.22–7.40 (5H, m), 8.74 (1H, s)

EXAMPLE 23

Synthesis of mono(3-(3,4-dimethoxyphenyl)-2-propene-1-yl) 4-(3-chlorophenyl)-2,6-dimethyl-1,4-dihydropyridine-3,5-dicarboxylate 1) Synthesis of 5-(3-(3,4-dimethoxyphenyl)-2-propene-1-yl) 3-(2-cyanoethyl) 4-(3-chlorophenyl)-2,6-dimethyl-1,4-dihydropyridine-3,5-dicarboxylate:

The title compound was obtained from 321 mg (2.08 mmol) of 2-cyanoethyl 3-aminocrotonate, 573 mg (2.06 mmol) of 3-(3,4-dimethoxyphenyl)-2-propene-1-yl acetoacetate and 0.23 ml (2.03 mmol) of 3-chlorobenzaldehyde in the same manner as that of Example 1-1).
Yield: 591 mg (1.10 mmol) (54.2%)
MS (ESI, m/z) 535 (M−H)⁻
$^1$H-NMR (CDCl$_3$): 2.37 (3H, s), 2.38 (3H, s), 2.58–2.68 (2H, m), 3.89 (3H, s), 3.91 (3H, s), 4.22–4.29 (2H, m), 4.63–4.81 (2H, m), 5.01 (1H, s), 5.72 (1H, s), 6.12 (1H, dt, J=16 Hz), 6.48 (1H, d, J=16 Hz), 6.77–6.94 (3H, m), 7.07–7.27 (4H, m)

2) Synthesis of mono(3-(3,4-dimethoxyphenyl)-2-propene-1-yl) 4-(3-chlorophenyl)-2,6-dimethyl-1,4-dihydropyridine-3,5-dicarboxylate:

The title compound was obtained from 478 mg (0.89 mmol) of 5-(3-(3,4-dimethoxyphenyl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).
Yield: 245 mg (0.51 mmol) (56.9%)
MS (ESI, m/z) 482 (M−H)⁻
$^1$H-NMR (DMSO-d$_6$): 2.26 (3H, s), 2.30 (3H, s), 3.75 (3H, s), 3.78 (3H, s), 4.55–4.75 (2H, m), 4.93 (1H, s), 6.20 (1H, dt, J=16 Hz), 6.45 (1H, d, J=16 Hz), 6.89–7.28 (7H, m), 8.85 (1H, s)

EXAMPLE 24

Synthesis of mono(3-phenyl-2-propene-1-yl) 4-(3,5-dichlorophenyl)-2,6-dimethyl-1,4-dihydropyridine-3,5-dicarboxylate 1) Synthesis of 5-(3-phenyl-2-propene-1-yl) 3-(2-cyanoethyl) 4-(3,5-dichlorophenyl)-2,6-dimethyl-1,4-dihydropyridine-3,5-dicarboxylate:

The title compound was obtained from 463 mg (2.98 mmol) of 2-cyanoethyl acetoacetate, 653 mg (3.01 mmol) of cinnamyl 3-aminocrotonate and 535 mg (3.06 mmol) of 3,5-dichlorobenzaldehyde in the same manner as that of Example 1-1).
Yield: 921 mg (1.80 mmol) (60.4%)
MS (ESI, m/z) 509 (M−H)⁻
$^1$H H-NMR (CDCl$_3$): 2.37 (3H, s), 2.38 (3H, s), 2.63 (2H, t), 4.20–4.32 (2H, m), 4.64–4.82 (2H, m), 4.99 (1H, s), 5.80 (1H, s), 6.25 (1H, dt, J=16 Hz), 6.57 (1H, d, J=16 Hz), 7.13 (1H, t), 7.17 (2H, d), 7.22–7.41 (5H, m)

2) Synthesis of mono(3-phenyl-2-propene-1-yl) 4-(3,5-dichlorophenyl)-2,6-dimethyl-1,4-dihydropyridine-3,5-dicarboxylate:

The title compound was obtained from 720 mg (1.41 mmol) of 5-(3-phenyl-2-propene-1-yl) 3-(2-cyanoethyl) 4-(3,5-dichlorophenyl)-2,6-dimethyl-1,4-dihydropyridine-3,5-dicarboxylate in the same manner as that of Example 3-2).
Yield: 510 mg (1.11 mmol) (73.9%)
MS (ESI, m/z) 456 (M−H)⁻
$^1$H-NMR (DMSO-d$_6$): 2.27 (3H, s), 2.31 (3H, s), 4.59–4.79 (2H, m), 4.93 (1H, s), 6.32 (1H, dt, J=16 Hz), 6.53 (1H, d, J=16 Hz), 7.11 (2H, d), 7.22–7.43 (6H, m), 8.94 (1H, s)

EXAMPLE 25

Synthesis of mono(3-(2-methoxyphenyl)-2-propene-1-yl) 4-(3-chlorophenyl)-2,6-dimethyl-1,4-dihydropyridine-3,5-dicarboxylate 1) Synthesis of 5-(3-(2-methoxyphenyl)-2-propene-1-yl) 3-(2-cyanoethyl) 4-(3-chlorophenyl)-2,6-dimethyl-1,4-dihydropyridine-3,5-dicarboxylate:

The title compound was obtained from 316 mg (2.05 mmol) of 2-cyanoethyl 3-aminocrotonate, 501 mg (2.02 mmol) of 3-(2-methoxyphenyl)-2-propene-1-yl acetoacetate and 0.225 ml (1.99 mmol) of 3-chlorobenzaldehyde in the same manner as that of Example 1-1).
Yield: 329 mg (0.65 mmol) (32.6%)
MS (ESI, m/z) 505 (M−H)⁻
$^1$H-NMR (CDCl$_3$): 2.36 (3H, s), 2.37 (3H, s), 2.61 (2H, t), 3.85 (3H, s), 4.20–4.33 (2H, m), 4.71–4.76 (2H, m), 5.01 (1H, s), 5.68 (1H, s), 6.26 (1H, dt, J=16 Hz), 6.85–6.98 (2H, m), 7.09–7.28 (6H, m), 7.42 (1H, dd)

2) Synthesis of mono(3-(2-methoxyphenyl)-2-propene-1-yl) 4-(3-chlorophenyl)-2,6-dimethyl-1,4-dihydropyridine-3,5-dicarboxylate:

The title compound was obtained from 295 mg (0.58 mmol) of 5-(3-(2-methoxyphenyl)-2-propene-1-yl) 3-(2- cyanoethyl) 4-(3-chlorophenyl)-2,6-dimethyl-1,4-dihydropyridine-3,5-dicarboxylate in the same manner as that of Example 3-2).

Yield: 202 mg (0.45 mmol) (76.5%)

MS (ESI, m/z) 452 (M−H)$^−$ $^1$H-NMR (DMSO-d$_6$): 2.26 (3H, s), 2.30 (3H, s), 3.81 (3H, s), 4.64–4.70 (2H, m), 4.93 (1H, s), 6.29 (1H, dt, J=16 Hz), 6.86 (1H, d, J=16 Hz), 6.88–7.03 (2H, m), 7.11–7.19 (3H, m), 7.20–7.29 (2H, m), 7.43 (1H, dd), 8.85 (1H, s)

EXAMPLE 26

Synthesis of mono(3-(3-methoxyphenyl)-2-propene-1-yl) 4-(3-chlorophenyl)-2,6-dimethyl-1,4-dihydropyridine-3,5-dicarboxylate Synthesis of 5-(3-(3-methoxyphenyl)-2-propene-1-yl) 3-(2-cyanoethyl) 4-(3-chlorophenyl)-2,6-dimethyl-1,4-dihydropyridine-3,5-dicarboxylate:

The title compound was obtained from 389 mg (2.52 mmol) of 2-cyanoethyl 3-aminocrotonate, 624 mg (2.51 mmol) of 3-(3-methoxyphenyl)-2-propene-1-yl acetoacetate and 0.29 ml (2.56 mmol) of 3-chlorobenzaldehyde in the same manner as that of Example 1-1).

Yield: 604 mg (0.65 mmol) (47.4%)

MS (ESI, m/z) 505 (M−H)$^−$ $^1$H-NMR (CDCl$_3$): 2.37 (6H, s), 2.62 (2H, t), 3.82 (3H, s), 4.18-4.32 (2H, m), 4.64–4.82 (2H, m), 5.01 (1H, s), 5.76 (1H, s), 6.23 (1H, dt, J=16 Hz), 6.50 (2H, m), 6.78–6.97 (3H, m), 7.08–7.27 (5H, m)

2) Synthesis of mono(3-(3-methoxyphenyl)-2-propene-1-yl) 4-(3-chlorophenyl)-2,6-dimethyl-1,4-dihydropyridine-3,5-dicarboxylate:

The title compound was obtained from 521 mg (1.03 mmol) of 5-(3-(3-methoxyphenyl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 364 mg (0.80 mmol) (78.0%)

MS (ESI, m/z) 452 (M−H)$^−$ $^1$H-NMR (DMSO-d$_6$): 2.26 (3H, s), 2.30 (3H, s), 3.76 (3H, s), 4.58–4.77 (2H, m), 4.93 (1H, s), 6.33 (1H, dt, J=16 Hz), 6.47 (1H, d, J=16 Hz), 6.81–6.86 (1H, m), 6.93–6.98 (2H, m), 7.11– 7.29 (5H, m), 8.87 (1H, s)

EXAMPLE 27

Synthesis of mono(3-(pyridine-4-yl)-2-propene-1-yl) 4-(3-chlorophenyl)-2,6-dimethyl-1,4-dihydropyridine-3,5-dicarboxylate 1) Synthesis of 3-(pyridine-4-yl)-2-propene-1-yl acetoacetate:

495 mg (3.66 mmol)f 3-(pyridine-4-yl)-2-propene-1-ol, 0.61 ml (4.38 mmol) of triethylamine and 0.35 ml (4.54 mmol) of diketene were heated to 70° C. under stirring in 20 ml of toluene for 2 hours. A saturated aqueous sodium hydrogencarbonate solution was added to the reaction mixture at room temperature. After the extraction with ethyl acetate, the organic layer was dried over anhydrous sodium sulfate and then concentrated under reduced pressure to obtain the title compound.

Yield: 808 mg (3.68 mmol) (100%)

MS (ESI, m/z) 220 (M+H)$^+$ $^1$H-NMR (CDCl$_3$): 2.30 (3H, s), 3.53 (2H, s), 4.84 (2H, dd), 6.48 (1H, dt, J=16 Hz), 6.63 (1H, d, J=16 Hz), 7.25 (2H, dd), 8.57(2H, dd)

2) Synthesis of 5-(3-(pyridine-4-yl)-2-propene-1-yl) 3-(2-cyanoethyl) 4-(3-chlorophenyl)-2,6-dimethyl-1,4-dihydropyridine-3,5-dicarboxylate:

The title compound was obtained from 408 mg (2.65 mmol) of 2-cyanoethyl 3-aminocrotonate, 571 mg (2.61 mmol) of 3-(pyridine-4-yl)-2-propene-1-yl acetoacetate and 0.30 ml (2.65 mmol) of 3-chlorobenzaldehyde in the same manner as that of Example 1-1).

Yield: 372 mg (0.78 mmol) (29.3%)

MS (ESI, m/z) 476 (M−H)$^−$ $^1$H-NMR (CDCl$_3$): 2.37 (3H, s), 2.39 (3H, s), 2.63 (2H, dt), 4.24–4.32 (2H, m), 4.64–4.88 (2H, m), 5.03 (1H, s), 5.85 (1H, s), 6.32–6.50 (2H, m) 7.11–7.25 (6H, m), 8.52–8.58 (2H, m)

3) Synthesis of mono(3-(pyridine-4-yl)-2-propene-1-yl) 4-(3-chlorophenyl)-2,6-dimethyl-1,4-dihydropyridine-3,5-dicarboxylate:

The title compound was obtained from 362 mg (0.76 mmol) of 5-(3-(pyridine-4-yl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 238 mg (0.56 mmol) (74%)

MS (ESI, m/z) 423 (M−H)$^−$ $^1$H-NMR (DMSO-d$_6$): 2.26 (3H, s), 2.31 (3H, s), 4.62–4.83 (2H, m), 4.94 (1H, s), 6.39 (1H, d, J=16 Hz), 6.64 (1H, dt, J=16 Hz), 7.10–7.38 (6H, m), 8.51 (2H, dd), 8.90 (1H, s)

EXAMPLE 28

Synthesis of mono(3-(thiophene-2-yl)-2-propene-1-yl) 4-(3-chlorophenyl)-2,6-dimethyl-1,4-dihydropyridine-3,5-dicarboxylate 1) Synthesis of 3-(thiophene-2-yl)-2-propene-1-yl acetoacetate:

1.50 g (10.7 mmol) of 3-(thiophene-2-yl)-2-propene-1-ol, 0.5 ml (3.59 mmol) of triethylamine and 1.0 ml (13.0 mmol) of diketene were heated to 70° C. under stirring in 30 ml of toluene for 1.5 hours. A saturated aqueous sodium hydrogencarbonate solution was added to the reaction mixture at room temperature. After the extraction with ethyl acetate, the organic layer was dried over anhydrous sodium sulfate and then concentrated under reduced pressure to obtain the title compound.

Yield: 2.40 g (10.7 mmol) (100%)

MS (ESI, m/z) 225 (M+H)$^+$ $^1$H-NMR (CDCl$_3$): 2.28 (3H, s), 3.49 (2H, s), 4.76 (2H, dd), 6.10 (1H, dt, J=16 Hz), 6.80 (1H, d, J=16 Hz), 6.95–7.03 (2H, m), 7.20 (1H, d)

2) Synthesis of 5-(3-(thiophene-2-yl)-2-propene-1-yl) 3-(2-cyanoethyl) 4-(3-chlorophenyl)-2,6-dimethyl-1,4-dihydropyridine-3,5-dicarboxylate:

The title compound was obtained from 389 mg (2.52 mmol) of 2-cyanoethyl 3-aminocrotonate, 570 mg (2.54 mmol) of 3-(thiophene-2-yl)-2-propene-1-yl acetoacetate and 0.285 ml (2.52 mmol) of 3-chlorobenzaldehyde in the same manner as that of Example 1-1).

Yield: 424 mg (0.88 mmol) (34.8%)

MS (ESI, m/z) 481 (M−H)$^−$ $^1$H-NMR (CDCl$_3$): 2.36 (6H, s), 2.62 (2H, dt), 4.19–4.33 (2H, m), 4.58–4.77 (2H, m), 5.00 (1H, s), 5.77 (1H, s), 6.06 (1H, dt, J=16 Hz), 6.62 (1H, d, J=16 Hz), 6.94–6.98 (2H, m), 7.10–7.26 (5H, m)

3) Synthesis of mono(3-(thiophene-2-yl)-2-propene-1-yl) 4-(3-chlorophenyl)-2,6-dimethyl-1,4-dihydropyridine-3,5-dicarboxylate:

The title compound was obtained from 365 mg (0.76 mmol) of 5-(3-(thiophene-2-yl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 210 mg (0.49 mmol) (64.7%)
MS (ESI, m/z) 428 (M−H)⁻
¹H-NMR (DMSO-d₆): 2.26 (3H, s), 2.29 (3H, s), 4.53–4.76 (2H, m), 4.91 (1H, s), 6.04 (1H, dt, J=16 Hz), 6.65 (1H, d, J=16 Hz), 6.97–7.06 (2H, m), 7.12–7.29 (4H, m), 7.43 (1H, dd), 8.87 (1H, s)

EXAMPLE 29

Synthesis of mono(3-phenyl-2-propene-1-yl) (−)-4-(3-chlorophenyl)-2,6-dimethyl-1,4-dihydropyridine-3,5-dicarboxylate Optically active (3-phenyl-2-propene-1-yl) 3-(cyanoethyl) 4-(3-chlorophenyl)-2,6-dimethyl-1,4-dihydropyridine-3,5-dicarboxylate was obtained by using t-butyl ester of L-valine according to a well-known technique [Japanese Patent Unexamined Published Application (hereinafter referred to as "J. P. KOKAI") No. Sho 63-208573].

The title compound was obtained from 317 mg (0.66 mmol) of this compound in the same manner as that of Example 3-2).

Yield: 161 mg (0.38 mmol) (57.3%)
Optical yield: 96% e. e.
[α]D-33.9 (c1.02, MeOH)
¹H-NMR (DMSO-d₆): 2.26 (3H, s), 2.30 (3H, s), 4.56–4.77 (2H, m), 4.93 (1H, s), 6.32 (1H, dt), 6.51 (1H, d), 7.10–7.42 (9H, m), 8.86 (1H, s)

EXAMPLE 30

Synthesis of mono(3-(pyridine-2-yl)-2-propene-1-yl) 4-(3-chlorophenyl)-2,6-dimethyl-1,4-dihydropyridine-3,5-dicarboxylate 1) Synthesis of 5-(3-(pyridine-2-yl)-2-propene-1-yl) 3-(2-cyanoethyl) 4-(3-chlorophenyl)-2,6-dimethyl-1,4-dihydropyridine-3,5-dicarboxylate:

The title compound was obtained from 467 mg (3.03 mmol) of 2-cyanoethyl 3-aminocrotonate, 658 mg (3.00 mmol) of (3-(pyridine-2-yl)-2-propenyl) acetoacetate and 0.34 ml (3.00 mmol) of 3-chlorobenzaldehyde in the same manner as that of Example 1-1).

Yield: 520 mg (1.09 mmol) (36.3%)
MS (ESI, m/z) 476 (M−H)⁻
¹H-NMR (CDCl₃): 2.37 (3H, s), 2.38 (3H, s), 2.64 (2H, dt), 4.20–4.34 (2H, m), 4.66–4.82 (2H, m), 5.03 (1H, s), 5.80 (1H, brd), 6.56 (1H, d), 6.75 (1H, dt), 7.08–7.28 (6H, m), 7.63 (1H, dd), 8.55 (1H, d)

2) Synthesis of mono(3-(pyridine-2-yl)-2-propene-1-yl) 4-(3-chlorophenyl)-2,6-dimethyl-1,4-dihydropyridine-3,5-dicarboxylate:

The title compound was obtained from 422 mg (0.88 mmol) of 5-(3-(pyridine-2-yl)-2-propene-1-yl 3-(2-cyanoethyl) 4-(3-chlorophenyl)-2,6-dimethyl-1,4-dihydropyridine-3,5-dicarboxylate in the same manner as that of Example 3-2).

Yield: 298 mg (0.70 mmol) (79.3%)
MS (ESI, m/z) 423 (M−H)⁻
¹H-NMR (DMSO-d₆): 2.27 (3H, s), 2.31 (3H, s), 4.66–4.83 (2H, m), 4.94 (1H, s), 6.54 (1H, d), 6.77 (1H, dt), 7.11–7.29 (5H, m), 7.34 (1H, d), 7.75 (1H, t), 8.52 (1H, d), 8.89 (1H, s)

EXAMPLE 31

Synthesis of mono(3-(phenyl-2-propene-1-yl) 4-(4-cyanophenyl)-2,6-dimethyl-1,4-dihydropyridine-3,5-dicarboxylate 1) Synthesis of 5-(3-phenyl-2-propene-1-yl 3-(2-cyanoethyl) 4-(4-cyanophenyl)-2,6-dimethyl-1,4-dihydropyridine-3,5-dicarboxylate:

The title compound was obtained from 466 mg (3.0 mmol) of 2-cyanoethyl acetoacetate, 652 mg (3.0 mmol) of cinnamyl 3-aminocrotonate and 394 mg (3.0 mmol) of 4-cyanobenzaldehyde in the same manner as that of Example 1-1).

Yield: 781 mg (1.67 mmol) (56%)
MS (ESI, m/z) 466 (M−H)⁻
¹H-NMR (CDCl₃): 2.37 (6H, s), 2.62 (2H, t), 4.22–4.28 (2H, m), 4.63–4.79 (2H, m), 5.08 (1H, s), 5.95 (1H, bs), 6.19 (1H, dt), 6.51 (1H, d), 7.22–7.35 (5H, m), 7.40–7.45 (2H, m), 7.47–7.52 (2H, m)

2) Synthesis of mono(3-phenyl-2-propene-1-yl) 4-(4-cyanophenyl)-2,6-dimethyl-1,4-dihydropyridine-3,5-dicarboxylate:

781 mg (1.67 mmol) of 5-(3-phenyl-2-propene-1-yl 3-(2-cyanoethyl) 4-(4-cyanophenyl)-2,6-dimethyl-1,4-dihydropyridine-3,5-dicarboxylate was dissolved in 33.4 ml of methanol. 3.34 ml of 1 N aqueous sodium hydroxide solution was added to the resultant solution, and they were stirred at room temperature for 2 hours. 2 N hydrochloric acid was added to the reaction mixture. Methanol was evaporated under reduced pressure. After the extraction with ethyl acetate, the organic layer was dried over anhydrous sodium sulfate, and then concentrated under reduced pressure. The residue was washed with hexane/ethyl acetate (1:1) and dried under reduced pressure to obtain the title compound.

Yield: 334 mg (0.804 mmol) (48%)
MS (ESI, m/z) 413 (M−H)⁻
¹H-NMR (DMSO-d₆): 2.25 (3H, s), 2.30 (3H, s), 4.58–4.74 (2H, m), 5.00 (1H, s), 6.29 (1H, dt), 6.45 (1H, d), 7.22–7.39 (7H, m), 7.65–7.70 (2H, m), 8.90 (1H, bs)

EXAMPLE 32

Synthesis of mono(3-phenyl-2-propene-1-yl) 4-(4-chlorophenyl)-2,6-dimethyl-1,4-dihydropyridine-3,5-dicarboxylate 1) Synthesis of 5-(3-phenyl-2-propene-1-yl) 3-(2-cyanoethyl) 4-(4-chlorophenyl)-2,6-dimethyl-1,4-dihydropyridine-3,5-dicarboxylate:

The title compound was obtained from 466 mg (3.0 mmol) of 2-cyanoethyl acetoacetate, 652 mg (3.0 mol) of cinnamyl 3-aminocrotonate and 422 mg (3.0 mmol) of 4-chlorobenzaldehyde in the same manner as that of Example 1-1).

Yield: 830 mg (1.74 mmol) (58%)
MS (ESI, m/z) 475 (M−H)⁻
¹H-NMR (CDCl₃): 2.35 (3H, s), 2.36 (3H, s), 2.61 (2H, t), 4.21–4.29 (2H, m), 4.63–4.81 (2H, m), 5.00 (1H, s), 5.74 (1H, bs), 6.20 (1H, dt), 6.49 (1H, d), 7.16–7.34 (9H, m)

2) Synthesis of mono(3-phenyl-2-propene-1-yl) 4-(4-chlorophenyl)-2,6-dimethyl-1,4-dihydropyridine-3,5-dicarboxylate:

830 mg (1.75 mmol) of 5-(3-phenyl-2-propene-1-yl 3-(2-cyanoethyl) 4-(4-chlorophenyl)-2,6-dimethyl-1,4-dihydropyridine-3,5-dicarboxylate was dissolved in 35 ml of methanol. 3.5 ml of 1 N aqueous sodium hydroxide solution was added to the resultant solution, and they were stirred at room temperature for 2 hours. 2 N hydrochloric acid was added to the reaction mixture. Methanol was evaporated under reduced pressure. After the extraction with ethyl acetate, the organic layer was dried over anhydrous sodium sulfate, and then concentrated under reduced pressure. The residue was washed with hexane/ethyl acetate (1:1) and dried under reduced pressure to obtain the title compound.

Yield: 509 mg (1.20 mmol) (69%)
MS (ESI, m/z) 422 (M–H)⁻
$^1$H-NMR (DMSO-$d_6$): 2.24 (3H, s), 2.29 (3H, s), 4.57–4.76 (2H, m), 4.93 (1H, s), 6.30 (1H, dt), 6.43 (1H, d), 7.16–7.38 (9H, m), 8.79 (1H, bs)

EXAMPLE 33

Synthesis of mono(3-phenyl-2-propene-1-yl) 2,6-dimethyl-4-(4-nitrophenyl)-1,4-dihydropyridine-3,5-dicarboxylate 1) Synthesis of 5-(3-phenyl-2-propene-1-yl 3-(2-cyanoethyl) 2,6-dimethyl-4-(4-nitrophenyl)-1,4-dihydropyridine-3,5-dicarboxylate:

The title compound was obtained from 337 mg (2.17 mmol) of 2-cyanoethyl acetoacetate, 472 mg (2.17 mmol) of cinnamyl 3-aminocrotonate and 328 mg (2.17 mmol) of 4-nitrobenzaldehyde in the same manner as that of Example 1-1).

Yield: 734 mg (1.50 mmol) (69%)
MS (ESI, m/z) 486 (M–H)⁻
$^1$H-NMR (CDCl$_3$): 2.38 (6H, s), 2.63 (2H, t), 4.25 (2H, t), 4.64–4.79 (2H, m), 5.14 (1H, s), 5.83 (1H, bs), 6.20 (1H, dt), 6.52 (1H, d), 7.23–7.35 (5H, m), 7.45–7.51 (2H, m), 8.04–8.10 (2H, m)

2) Synthesis of mono(3-phenyl-2-propene-1-yl) 2,6-dimethyl-4-(4-nitrophenyl)-1,4-dihydropyridine-3,5-dicarboxylate:

733 mg (1.50 mmol) of 5-(3-phenyl-2-propene-1-yl) 3-(2-cyanoethyl) 2,6-dimethyl-4-(4-nitrophenyl)-1,4-dihydropyridine-3,5-dicarboxylate was dissolved in 30 ml of methanol. 3 ml of 1 N aqueous sodium hydroxide solution was added to the resultant solution, and they were stirred at room temperature for 2 hours. 2 N hydrochloric acid was added to the reaction mixture. Methanol was evaporated under reduced pressure. After the extraction with ethyl acetate, the organic layer was dried over anhydrous sodium sulfate, and then concentrated under reduced pressure. The residue was washed with hexane/ethyl acetate (1:1) and dried under reduced pressure to obtain the title compound.

Yield: 538 mg (1.24 mmol) (83%)
MS (ESI, m/z) 433 (M–H)⁻
$^1$H-NMR (DMSO-$d_6$): 2.27 (3H, s), 2.31 (3H, s), 4.58–4.75 (2H, m), 5.05 (1H, s), 6.30 (1H, dt), 6.45 (1H, d), 7.22–7.38 (5H, m), 7.41–7.46 (2H, m), 8.06–8.12 (2H, m), 8.94 (1H, bs)

EXAMPLE 34

Synthesis of mono(3-phenyl-2-propene-1-yl) (+)-4-(3-chlorophenyl)-2,6-dimethyl-1,4-dihydropyridine-3,5-dicarboxylate Optically active (3-phenyl-2-propene-1-yl) 3-(cyanoethyl) 4-(3-chlorophenyl)-2,6-dimethyl-1,4-dihydropyridine-3,5-dicarboxylate was obtained by using t-butyl ester of D-valine according to a well-known technique [J. P. KOKAI No. Sho 63-208573].

The title compound was obtained from 436 mg (0.97 mmol) of this compound in the same manner as that of Example 3-2).

Yield: 250 mg (0.59 mmol) (60.8%)
Optical yield: 94% e. e.
[α]D+30.4 (c1.01, MeOH)
$^1$H-NMR (DMSO-$d_6$): 2.26 (3H, s), 2.30 (3H, s), 4.58–4.78 (2H, m), 4.94 (1H, s), 6.32 (1H, dt), 6.51 (1H, d), 7.12–7.43 (9H, m), 8.86 (1H, s)

EXAMPLE 35

Synthesis of mono(3-phenyl-2-propene-1-yl) 2,6-dimethyl-4-(2-phenylethynyl)-1,4-dihydropyridine-3,5-dicarboxylate 1) Synthesis of (3-phenyl-2-propene-1-yl) 3-(2-cyanoethyl) 2,6-dimethyl-4-(2-phenylethynyl)-1,4-dihydropyridine-3,5-dicarboxylate:

The title compound was obtained from 414 mg (2.67 mmol) of 2-cyanoethyl acetoacetate, 574 mg (2.64 mmol) of cinnamyl 3-aminocrotonate and 0.325 ml (2.66 mmol) of phenylpropargylaldehyde in the same manner as that of Example 1-1).

Yield: 793 mg (1.70 mmol) (64.4%)
MS (ESI, m/z) 465 (M–H)⁻
$^1$H-NMR (CDCl$_3$): 2.36 (3H, s), 2.36 (3H, s), 2.76 (2H, t), 4.32–4.51 (2H, m), 4.75–5.02 (2H, m), 5.02 (1H, s), 5.82 (1H, s), 6.36 (1H, dt), 6.72 (1H, d), 7.14–7.36 (10H, m)

2) Synthesis of mono(3-phenyl-2-propene-1-yl) 2,6-dimethyl-4-(2-phenylethynyl)-1,4-dihydropyridine-3,5-dicarboxylate:

The title compound was obtained from 532 mg (1.14 mmol) of (3-phenyl-2-propene-1-yl) 3-(2-cyanoethyl) 2,6-dimethyl-4-(2-phenylethynyl)-1,4-dihydropyridine-3,5-dicarboxylate in the same manner as that of Example 3-2).

Yield: 387 mg (0.93 mmol) (82.0%)
MS (ESI, m/z) 412 (M–H)⁻
$^1$H-NMR (DMSO-$d_6$): 2.25 (3H, s), 2.29 (3H, s), 4.67–4.95 (2H, m), 4.89 (1H, s), 6.42 (1H, dt), 6.71 (1H, d), 7.21–7.33 (8H, m), 7.34–7.40 (2H, m), 8.98 (1, s)

EXAMPLE 36

Synthesis of mono(3-phenyl-2-propene-1-yl) 2,6-dimethyl-4-(2-methylphenyl)-1,4-dihydropyridine-3,5-dicarboxylate 1) Synthesis of (3-phenyl-2-propene-1-yl) 3-(2-cyanoethyl) 2,6-dimethyl-4-(2-methylphenyl)-1,4-dihydropyridine-3,5-dicarboxylate:

The title compound was obtained from 306 mg (1.97 mmol) of 2-cyanoethyl acetoacetate, 434 mg (2.00 mmol) of cinnamyl 3-aminocrotonate and 0.23 ml (1.99 mmol) of 2-methylphenylaldehyde in the same manner as that of Example 1-1).

Yield: 383 mg (0.84 mmol) (42.6%)
MS (ESI, m/z) 455 (M–H)⁻
$^1$H-NMR (CDCl$_3$): 2.34 (3H, s), 2.34 (3H, s), 2.54 (3H, s), 2.59 (2H, t), 4.24 (2H, t), 4.67–4.74 (2H, m), 5.18 (1H, s), 5.63 (1H, s), 6.18 (1H, dt), 6.44 (1H, d), 7.00–7.12 (2H, m), 7.23–7.33 (7H, m)

2) Synthesis of mono(3-phenyl-2-propene-1-yl) 2,6-dimethyl-4-(2-methylphenyl)-1,4-dihydropyridine-3,5-dicarboxylate:

The title compound was obtained from 378 mg (0.83 mmol) of (3-phenyl-2-propene-1-yl) 3-(2-cyanoethyl) 2,6-dimethyl-4-(2-methylphenyl)-1,4-dihydropyridine-3,5-dicarboxylate in the same manner as that of Example 3-2).

Yield: 225 mg (0.56 mmol) (67.4%)

MS (ESI, m/z) 402 (M–H)−

$^1$H-NMR (DMSO-d$_6$): 2.22 (3H, s), 2.27 (3H, s), 2.47 (3H, s), 4.63 (2H, m), 5.03 (1H, s), 6.26 (1H, dt), 6.42 (1H, d), 6.91–7.00 (2H, m), 7.02–7.09 (1H, m), 7.20–7.38 (6H, m), 8.68 (1H, s)

EXAMPLE 37

Synthesis of mono(3-phenyl-2-propene-1-yl) 2,6-dimethyl-4-(pyridine-3-yl)-1,4-dihydropyridine-3,5-dicarboxylate 1) Synthesis of (3-phenyl-2-propene-1-yl) 3-(2-cyanoethyl) 2,6-dimethyl-4-(pyridine-3-yl)-1,4-dihydropyridine-3,5-dicarboxylate:

384 mg (2.48 mmol) of 2-cyanoethyl acetoacetate, 542 mg (2.49 mmol) of cinnamyl 3-aminocrotonate and 0.235 ml (2.49 mmol) of 3-pyridylaldehyde were heated at 80° C. under stirring in 20 ml of 2-propanol overnight. 2-Propanol was evaporated under reduced pressure, and the residue was purified by the silica gel chromatography (chloroform/methanol=50:1) to obtain the title compound.

Yield: 758 mg (1.71 mmol) (68.9%)

MS (ESI, m/z) 442 (M–H)−

$^1$H-NMR (CDCl$_3$): 2.37 (6H, s), 2.62 (2H, t), 4.25 (2H, dt), 4.72 (2H, dt), 5.02 (1H, s), 6.15 (1H, brd), 6.23 (1H, dt), 6.53 (1H, d), 7.12–7.18 (1H, m), 7.22–7.38 (5H, m), 7.64 (1H, dt), 8.38 (1H, dd), 8.55 (1H, d)

2) Synthesis of mono(3-phenyl-2-propene-1-yl) 2,6-dimethyl-4-(pyridine-3-yl)-1,4-dihydropyridine-3,5-dicarboxylate:

The title compound was obtained from 655 mg (1.48 mmol) of (3-phenyl-2-propene-1-yl) 3-(2-cyanoethyl) 2,6-dimethyl-4-(pyridine-3-yl)-1,4-dihydropyridine-3,5-dicarboxylate in the same manner as that of Example 3-2).

Yield: 494 mg (1.27 mmol) (85.6%)

MS (ESI, m/z) 389 (M–H)−

$^1$H-NMR (DMSO-d$_6$): 2.27 (3H, s), 2.31 (3H, s), 4.60–4.76 (2H, m), 4.92 (1H, s), 6.31 (1H, dt), 6.49 (1H, d), 7.21–7.42 (6H, m), 7.49–7.55 (1H, m), 8.29–8.34 (1H, m), 8.40 (1H, d), 8.90 (1H, s)

EXAMPLE 38

Synthesis of mono(3-phenyl-2-propene-1-yl) 2,6-dimethyl-4-(furan-3-yl)-1,4-dihydropyridine-3,5-dicarboxylate 1) Synthesis of (3-phenyl-2-propene-1-yl) 3-(2-cyanoethyl) 2,6-dimethyl-4-(furan-3-yl)-1,4-dihydropyridine-3,5-dicarboxylate:

The title compound was obtained from 401 mg (2.58 mmol) of 2-cyanoethyl acetoacetate, 560 mg (2.58 mmol) of cinnamyl 3-aminocrotonate and 0.22 ml (2.54 mmol) of 3-furylaldehyde in the same manner as that of Example 1-1).

Yield: 745 mg (1.72 mmol) (66.8%)

MS (ESI, m/z) 431 (M–H)−

$^1$H-NMR (CDCl$_3$): 2.33 (6H, s), 2.68 (2H, t), 4.24–4.40 (2H, m), 4.72–4.87 (2H, m), 5.01 (1H, s), 6.29 (1H, m), 6.30 (1H, dt), 6.59 (1H, d), 7.18–7.40 (7H, m)

2) Synthesis of mono(3-phenyl-2-propene-1-yl) 2,6-dimethyl-4-(furan-3-yl)-1,4-dihydropyridine-3,5-dicarboxylate:

The title compound was obtained from 602 mg (1.39 mmol) of (3-phenyl-2-propene-1-yl) 3-(2-cyanoethyl) 2,6-dimethyl-4-(furan-3-yl)-1,4-dihydropyridine-3,5-dicarboxylate in the same manner as that of Example 3-2).

Yield: 373 mg (0.98 mmol) (70.7%)

MS (ESI, m/z) 378 (M–H)−

$^1$H-NMR (DMSO-d$_6$): 2.23 (3H, s), 2.27 (3H, s), 4.65–4.82 (2H, m), 4.84 (1H, s), 6.22 (1H, m), 6.39 (1H, dt), 6.58 (1H, d), 7.16 (1H, m), 7.22–7.38 (3H, m), 7.39–7.46 (3H, m), 8.82 (1H, s)

EXAMPLE 39

Synthesis of mono(3-(pyridine-3-yl)-2-propene-1-yl) 4-(3-chlorophenyl)-2,6-dimethyl-1,4-dihydropyridine-3,5-dicarboxylate 1) Synthesis of 5-(3-(pyridine-3-yl)-2-propene-1-yl) 3-(2-cyanoethyl) 4-(3-chlorophenyl)-2,6-dimethyl-1,4-dihydropyridine-3,5-dicarboxylate:

387 mg (2.51 mmol) of 2-cyanoethyl 3-aminocrotonate, 547 mg (2.49 mmol) of (3-(pyridine-3-yl)-2-propene-1-yl) acetoacetate, and 0.285 ml (2.51 mmol) of 3-chlorobenzaldehyde were heated at 80° C. under stirring in 20 ml of 2-propanol overnight. 2-Propanol was evaporated under reduced pressure, and the residue was purified by the silica gel chromatography (chloroform/methanol=100:1) to obtain the title compound.

Yield: 492 mg (1.03 mmol) (41.4%)

MS (ESI, m/z) 476 (M–H)−

$^1$H-NMR (CDCl$_3$): 2.37 (3H, s), 2.38 (3H, s), 2.63 (2H, t), 4.22–4.31 (2H, m), 4.64–4.86 (2H, m), 5.02 (1H, s), 5.85 (1H, s), 6.29 (1H, dt), 6.45 (1H, d), 7.09–7.28 (5H, m), 7.67 (1H, dd), 8.44–8.56 (2H, m)

2) Synthesis of mono(3-(pyridine-3-yl)-2-propene-1-yl) 4-(3-chlorophenyl)-2,6-dimethyl-1,4-dihydropyridine-3,5-dicarboxylate:

The title compound was obtained from 482 mg (1.01 mmol) of 5-(3-(pyridine-3-yl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 236 mg (0.56 mmol) (55.0%)

MS (ESI, m/z) 423 (M–H)−

$^1$H-NMR (DMSO-d$_6$): 2.26 (3H, s), 2.31 (3H, s), 4.61–4.81 (2H, m), 4.94 (1H, s), 6.49 (2H, m), 7.12–7.20 (3H, m), 7.22–7.29 (1H, m), 7.34–7.40 (1H, m), 7.85 (1H, m), 8.45 (1H, dd), 8.54 (1H, d), 8.89 (1H, s)

EXAMPLE 40

Synthesis of mono(3-(furan-2-yl)-2-propene-1-yl) 4-(3-chlorophenyl)-2,6-dimethyl-1,4-dihydropyridine-3,5-dicarboxylate 1) Synthesis of 5-(3-(furan-2-yl)-2-propene-1-yl) 3-(2-cyanoethyl) 4-(3-chlorophenyl)-2,6-dimethyl-1,4-dihydropyridine-3,5-dicarboxylate:

The title compound was obtained from 465 mg (3.02 mmol) of 2-cyanoethyl 3-aminocrotonate, 653 mg (3.13 mmol) of (3-(furan-2-yl)-2-propene-1-yl) acetoacetate and 0.34 ml (3.0 mmol) of 3-chlorobenzaldehyde in the same manner as that of Example 1-1).

Yield: 638 mg (1.37 mmol) (45.5%)
MS (ESI, m/z) 465 (M−H)−
$^1$H-NMR (CDCl$_3$): 2.36 (6H, s), 2.63 (2H, t), 4.19–4.38 (2H, m), 4.61–4.80 (2H, m), 5.00 (1H, s), 5.76 (1H, s), 6.16 (1H, dt), 6.22–6.38 (2H, m), 7.09–7.25 (4H, m), 7.34 (1H, s)

2) Synthesis of mono(3-(furan-2-yl)-2-propene-1-yl) 4-(3-chlorophenyl)-2,6-dimethyl-1,4-dihydropyridine-3,5-dicarboxylate:

The title compound was obtained from 561 mg (1.20 mmol) of 5-(3-(furan-2-yl)-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 221 mg (0.53 mmol) (44.6%)
MS (ESI, m/z) 412 (M−H)−
$^1$H-NMR (DMSO-d$_6$): 2.26 (3H, s), 2.30 (3H, s), 4.55–4.75 (2H, m), 4.91 (1H, s), 6.10 (1H, dt), 6.32 (1H, d), 6.36–6.50 (2H, m), 7.09–7.29 (4H, m), 7.61 (1H, s), 8.88 (1H, s)

EXAMPLE 41

Synthesis of mono(3-phenyl-2-propene-1-yl) 4-(3-carboxyphenyl)-2,6-dimethyl-1,4-dihydropyridine-3,5-dicarboxylate 1) Synthesis of 5-(3-phenyl-2-propene-1-yl) 3-(2-cyanoethyl) 4-(3-carboxyphenyl)-2,6-dimethyl-1,4-dihydropyridine-3,5-dicarboxylate:

466 mg (3.0 mmol) of 2-cyanoethyl 3-aminoacetate, 652 mg (3.0 mmol) of cinnamyl 3-aminocrotonate and 451 mg (3.0 mmol) of 3-carboxybenzaldehyde were heated at 70° C. under stirring in 15 ml of 2-propanol overnight. 2-Propanol was evaporated under reduced pressure, and the residue was purified by the silica gel chromatography (chloroform/methanol=9:1) to obtain the title compound.

Yield: 833 mg (1.71 mmol) (57%)
MS (ESI, m/z) 485 (M−H)−
$^1$H-NMR (CDCl$_3$): 2.30 (6H, s), 2.57 (2H, t), 4.12–4.28 (2H, m), 4.61–4.77 (2H, m), 5.07 (1H, s), 6.20 (1H, dt), 6.50 (1H, d), 7.17–7.37 (7H, m), 7.49–7.57 (1H, m), 7.78–7.86 (1H, m), 7.99 (1H, bs)

2) Synthesis of mono(3-phenyl-2-propene-1-yl) 4-(3-carboxyphenyl)-2,6-dimethyl-1,4-dihydropyridine-3,5-dicarboxylate:

The title compound was obtained from 277 mg (0.569 mmol) of 5-(3-phenyl-2-propene-1-yl) 3-(2-cyanoethyl) 4-(3-carboxyphenyl)-2,6-dimethyl-1,4-dihydropyridine-3,5-dicarboxylate in the same manner as that of Example 3-2).

Yield: 101 mg (0.232 mmol) (41%)
MS (ESI, m/z) 432 (M−H)−
$^1$H-NMR (DMSO-d$_6$): 2.26 (3H, s), 2.30 (3H, s), 4.57–4.74 (2H, m), 4.98 (1H, s), 6.31 (1H, dt), 6.48 (1H, d), 7.20–7.43 (7H, m), 7.67–7.72 (1H, m), 7.81–7.84 (1H, m), 8.86 (1H, bs)

EXAMPLE 42

Synthesis of 3-phenyl-2-propene-1-yl 4-(3-chlorophenyl)-2,6-dimethyl-5-nitro-1,4-dihydropyridine-3-carboxylate The title compound was obtained from 312 mg (3.03 mmol) of nitroacetone, 658 mg (3.03 mmol) of 2-cyanoethyl 3-aminocrotonate and 0.34 ml (3.0 mmol) of 3-chlorobenzaldehyde in the same manner as that of Example 1-1)

Yield: 259 mg (0.61 mmol) (20.3%)
MS (ESI, m/z) 423 (M−H)−
$^1$H-NMR (CDCl$_3$): 2.41 (3H, s), 2.55 (3H, s), 2.55 (3H, s), 4.64–4.80 (2H, m), 5.43 (1H, s), 5.88 ($_1$H, s), 6.19 (1H, dt), 6.53 (1H, d), 7.13–7.16 (2H, m), 7.21–7.38 (7H, m)

EXAMPLE 43

Synthesis of mono(3-phenyl-2-propene-1-yl) 2,6-dimethyl-4-(2-naphthyl)-1,4-dihydropyridine-3,5-dicarboxylate 1) Synthesis of 5-(3-phenyl-2-propene-1-yl) 3-(2-cyanoethyl) 2,6-dimethyl-4-(2-naphthyl)-1,4-dihydropyridine-3,5-dicarboxylate:

The title compound was obtained from 310 mg (2.0 mmol) of 2-cyanoethyl acetoacetate, 435 mg (2.0 mmol) of cinnamyl 3-aminocrotonate and 313 mg (2.0 mmol) of 2-naphthoaldehyde in the same manner as that of Example 1-1)

Yield: 429 mg (0.873 mmol) (44%)
MS (ESI, m/z) 491 (M−H)−
$^1$H-NMR (CDCl$_3$): 2.40 (6H, s), 2.57 (2H, t), 4.20–4.27 (2H, m), 4.60–4.80 (2H, m), 5.20 (1H, s), 5.73 (1H, bs), 6.17 (1H, dt), 6.43 (1H, d), 7.16–7.77 (12H, m)

2) Synthesis of mono(3-phenyl-2-propene-1-yl) 2,6-dimethyl-4-(2-naphthyl)-1,4-dihydropyridine-3,5-dicarboxylate:

The title compound was obtained from 429 mg (0.873 mmol) of 5-(3-phenyl-2-propene-1-yl) 3-(2-cyanoethyl) 2,6-dimethyl-4-(2-naphthyl)-1,4-dihydropyridine-3,5-dicarboxylate in the same manner as that of Example 3-2).

Yield: 234 mg (0.533 mmol) (61%)
MS (ESI, m/z) 438 (M−H)−
$^1$H-NMR (DMSO-d$_6$): 2.28 (3H, s), 2.32 (3H, s), 4.56–4.77 (2H, m), 5.12 (1H, s), 6.27 (1H, dt), 6.39 (1H, d), 7.16–7.30 (5H, m), 7.38–7.46 (3H, m), 7.58–7.60 (1H, m), 7.73–7.82 (3H, m), 8.84(1H, bs)

EXAMPLE 44

Synthesis of mono(3-phenyl-2-propene-1-yl) 2,6-dimethyl-4-(3-phenyl-2-propene-1-yl)-1,4-dihydropyridine-3,5-dicarboxylate 1) Synthesis of 5-(3-phenyl-2-propene-1-yl) 3-(2-cyanoethyl) 2,6-dimethyl-4-(3-phenyl-2-propene-1-yl)-1,4-dihydropyridine-3,5-dicarboxylate:

The title compound was obtained from 310 mg (2.0 mmol) of 2-cyanoethyl 3-acetoacetate, 435 mg (2.0 mmol) of cinnamyl 3-aminocrotonate and 0.253 ml (2.0 mmol) of cinnamaldehyde in the same manner as that of Example 1-1).

Yield: 520 mg (1.11 mmol) (56%)
MS (ESI, m/z) 467 (M−H)−
$^1$H-NMR (CDCl$_3$): 2.34 (6H, s), 2.70 (2H, t), 4.30–4.42 (2H, m), 4.66 (1H, d), 4.70–4.92 (2H, m), 5.69 (1H, bs), 6.12–6.35 (3H, m), 6.65 (1H, d), 7.13–7.33 (10H, m)

2) Synthesis of mono(3-phenyl-2-propene-1-yl) 2,6-dimethyl-4-(3-phenyl-2-propene-1-yl)-1,4-dihydropyridine-3,5-dicarboxylate:

The title compound was obtained from 520mg (1.11 mmol) of 5-(3-phenyl-2-propene-1-yl) 3-(2-cyanoethyl) 2,6- dimethyl-4-(3-phenyl-2-propene-1-yl)-1,4-dihydropyridine-3,5-dicarboxylate in the same manner as that of Example 3-2).

Yield: 146 mg (0.351 mmol) (32%)

MS (ESI, m/z) 414 (M–H)⁻ ¹H-NMR (DMSO-d₆): 2.25 (3H, s), 2.29 (3H, s), 4.51 (1H, t), 4.63–4.87 (2H, m), 6.12 (1H, d), 6.39 (1H, dt), 6.63 (1H, d), 7.13–7.37 (10H, m), 8.79 (1H, m)

EXAMPLE 45

Synthesis of 3-(3-phenyl-2-propene-1-yl) 4-(3-chlorophenyl)-2-dimethoxymethyl-6-methyl-1,4-dihydropyridine-3,5-dicarboxylate 1) Synthesis of (3-phenyl-2-propene-1-yl) 4,4-dimethoxy-3-oxobutyrate:

2.68 g (14.1 mmol) of ethyl 4,4-dimethoxy-3-oxobutyrate, 5.14 ml (40.0 mmol) of cinnamyl alcohol and 244 mg (2.0 mmol) of 4-dimethylaminopyridine were heated under reflux in 40 ml of toluene for two nights. A phosphate buffer solution was added to the reaction liquid. After the extraction with ethyl acetate, the organic layer was washed with a saturated aqueous salt solution and then dried over anhydrous sodium sulfate. The solvent was distilled under reduced pressure, and the residue was purified by the silica gel chromatography (hexane/ethyl acetate=9/1) to obtain the title compound.

Yield: 2.83 g (10.2 mmol) (72%).

MS (ESI, m/z) 277 (M–H)⁻

¹H-NMR (CDCl₃): 3.42 (6H, s), 3.63 (2H, s), 4.59 (1H, s), 4.78–4.83 (2H, m), 6.28 (1H, dt), 6.67 (1H, d), 7.23–7.42 (5H, m)

2) Synthesis of 3-(3-phenyl-2-propene-1-yl) 5-(2-cyanoethyl) 4-(3-chlorophenyl)-2-dimethoxylmethyl-6-methyl-1,4-dihydropyridine-3,5-dicarboxylate:

2.09 g (7.5 mmol) of (3-phenyl-2-propene-1-yl) 4,4-dimethoxy-3-oxobutyrate, 0.85 ml (7.5 mmol) of 3-chlorobenzaldehyde and 0.1 ml of piperidine were heated under reflux in 7.5 ml of benzene overnight while water was removed. The reaction liquid was washed was water and dried over anhydrous sodium sulfate. The solvent was distilled under reduced pressure, and the residue was heated together with 1.16 g (7.5 mmol) of 2-cyanoethyl 3-aminocrotonate at 70° C. in 37.5 ml of 2-propanol under stirring for four nights. The heating and stirring were continued at 120° C. overnight while 2-propanol was evaporated under atmospheric pressure. The residue was purified by the silica gel chromatography (hexane/ethyl acetate=2/1) to obtain the title compound.

Yield: 2.02 g (3.76 mmol) (76%).

MS (ESI, m/z) 535 (M–H)⁻

¹H-NMR (CDCl₃): 2.39 (3H, s), 2.61 (2H, t), 3.44 (3H, s), 3.47 (3H, s), 4.19–4.32 (2H, m), 4.66–4.83 (2H, m), 5.05 (1H, s), 6.04 (1H, s), 6.24 (1H, dt), 6.56 (1H, d), 6.83 (1H, bs), 7.10–7.39 (9H, m)

3) Synthesis of 3-(3-phenyl-2-propene-1-yl) 4-(3-chlorophenyl)-2dimethoxylmethyl-6-methyl-1,4-dihydropyridine-3,5-dicarboxylate:

50.5 mg (0.094 mmol) of 3-(3-phenyl-2-propene-1-yl) 5-(2-cyanoethyl) 4-(3-chlorophenyl)-2-dimethoxylmethyl-6-methyl-1,4-dihydropyridine-3,5-dicarboxylate was dissolved in 1.88 ml of methanol. 0.188 ml of 1 N aqueous sodium hydroxide solution was added to the obtained solution, and they were stirred at room temperature for 2 hours. An aqueous potassium hydrogensulfate solution was added to the reaction mixture, and then methanol was evaporated under reduced pressure. The residue was washed with water and hexane/ethyl acetate (3:1) and then dried under reduced pressure to obtain the title compound.

Yield: 11.0 mg (0.023 mmol) (24%).

MS (ESI, m/z) 482 (M–H)⁻

¹H-NMR (CDCl₃): 2.38 (3H, s), 3.43 (3H, s), 3.47 (3H, s), 4.65–4.83 (2H, m), 5.06 (1H, s), 6.04 (1H, s), 6.23 (1H, dt), 6.54 (1H, d), 6.86 (1H, bs), 7.07–7.38 (9H, m)

EXAMPLE 46

Synthesis of 3-(3-phenyl-2-propene-1-yl) 4-(3-chlorophenyl)-2-cyano-6-methyl-1,4-dihydropyridine-3,5-dicarboxylate 1) Synthesis of 3-(3-phenyl-2-propene-1-yl) 5-(2-cyanoethyl) 4-(3-chlorophenyl)-2-formyl-6-methyl-1,4-dihydropyridine 3,5-dicarboxylate:

1.82 g (3.38 mmol) of 3-(3-phenyl-2-propene-1-yl) 5-(2-cyanoethyl) 4-(3-chlorophenyl)-2-dimethoxylmethyl-6-methyl-1,4-dihydropyridine-3,5-dicarboxylate was dissolved in 12.7 ml of acetone. 1.27 ml of 6 N hydrochloric acid was added to the obtained solution, and they were stirred at 0° C. for 6 hours. Acetone was evaporated under reduced pressure, and then water was added to the residue. After the extraction with chloroform, the organic layer was successively washed with a saturated aqueous sodium hydrogencarbonate solution and saturated aqueous salt solution, and then dried over anhydrous sodium sulfate. The solvent was evaporated under reduced pressure and the residue was purified by the silica gel chromatography (hexane/ethyl acetate=3/1) to obtain the title compound.

Yield: 290 g (0.590 mmol) (17%).

MS (ESI, m/z) 489 (M–H)⁻

¹H-NMR (CDCl₃): 2.44 (3H, s), 2.62 (2H, t), 4.22–4.30 (2H, m), 4.76–4.91 (2H, m), 5.14 (1H, s), 6.25 (1H, dt), 6.62 (1H, d), 7.03 (1H, bs), 7.14–7.40 (9H, m), 10.51 (1H, s)

2) Synthesis of 3-(3-phenyl-2-propene-1-yl) 5-(2-cyanoethyl) 4-(3-chlorophenyl)-2-cyano-6-methyl-1,4-dihydropyridine-3,5-dicarboxylate:

290 mg (0.590 mmol) of 3-(3-phenyl-2-propene-1-yl) 5-(2-cyanoethyl) 4-(3-chlorophenyl)-2-formyl-6-methyl-1,4-dihydropyridinne-3,5-dicarboxylate, 49.6 mg (0.711 mmol) of hydroxylamine hydrochloride and 72.6 mg (0.886 mmol) of sodium acetate were heated at 45° C. under stirring for 5 hours. 0.195 ml (2.06 mmol) of acetic anhydride was added to the reaction liquid and they were stirred at 45° C. for 1.5 hours and then at 100° C. under stirring overnight. The solvent was evaporated under reduced pressure, and saturated aqueous sodium hydrogencarbonate solution was added to the residue. After the extraction with ethyl acetate, the organic layer was washed with water and then dried over anhydrous magnesium sulfate. The solvent was evaporated under reduced pressure, and the residue was purified by the silica gel chromatography (hexane/ethyl acetate=1/1) to obtain the title compound.

Yield: 155 mg (0.318 mmol) (54%).

MS (ESI, m/z) 486 (M–H)⁻

¹H-NMR (CDCl₃): 2.39 (3H, s), 2.62 (2H, t), 4.18–4.33 (2H, m), 4.75–4.93 (2H, m), 5.08 (1H, s), 6.25 (1H, dt), 6.63 (1H, d), 7.16–7.39 (9H, m)

3) Synthesis of 3-(3-phenyl-2-propene-1-yl) 4-(3-chlorophenyl)-2-cyano-6-methyl-1,4-dihydropyridine-3,5-dicarboxylate:

82.3 mg (1.69 mmol) of 3-(3-phenyl-2-propene-1-yl) 5-(2-cyanoethyl) 4-(3-chlorophenyl)-2-cyano-6-methyl-1,4-dihydropyridine-3,5-dicarboxylate was dissolved in 1.69 ml of tetrahydrofuran. 0.338 ml of 1 N aqueous sodium hydroxide solution was added to the obtained solution, and they were stirred at room temperature for 7 hours. An aqueous potassium hydrogensulfate solution was added to the reaction mixture, and then tetrahydrofuran was evaporated under reduced pressure. The residue was washed with water and hexane/ethyl acetate (1:2) and then dried under reduced pressure to obtain the title compound.

Yield: 33.2 mg (0.076 mmol) (45%).
MS (ESI, m/z) 433 (M–H)$^-$
$^1$H-NMR (d6-DMSO): 2.29 (3H, s), 4.70–4.90 (2H, m), 5.02 (1H, s), 6.31 (1H, dt), 6.60 (1H, d), 7.10–7.42 (9H, m)

EXAMPLE 47

Synthesis of mono(2-phenyloxyethyl) 4-(3-chlorophenyl)-2,6-dimethyl-1,4-dihydropyridine-3,5-dicarboxylate 1) Synthesis of mono(2-cyanoethyl) 4-(3-chlorophenyl)-2,6-dimethyl-1,4-dihydropyridine 3,5-dicarboxylate:

3.53 g (22.9 mmol) of 2-cyanoethyl 3-aminocrotonate, 4.40 g (22.9 mmol) of benzyl acetoacetate and 2.60 ml (23.0 mmol) of 3-chlorobenzaldehyde were heated at 80° C. under stirring in 100 ml of 2-propanol for 3 days. 2-Propanol was evaporated under reduced pressure to obtain 5-benzyl 3-(cyanoethyl) 4-(3-chlorophenyl)-2,6-dimethyl-1,4-dihydropyridine-3,5-dicarboxylate. 100 ml of ethyl acetate and 10% palladium/carbon were added to the reaction mixture, and they were stirred at room temperature in hydrogen atmosphere under atmospheric pressure for 7 days. The reaction liquid was filtered. The filtrate was evaporated under reduced pressure. The residue was washed with chloroform to obtain the title compound.

Yield: 4.82 g (13.4 mmol) (58.4%).
MS (ESI, m/z) 359 (M–H)$^-$
$^1$H-NMR (DMSO-d$_6$): 2.27 (3H, s), 2.29 (3H, s), 2.79–2.86 (2H, m), 4.15 (2H, t), 4.87 (1H, s), 7.10–7.28 (5H, m), 8.90 (1H, s)

2) Synthesis of 5-(2-phenyloxyethyl) 3-(2-cyanoethyl) 4-(3-chlorophenyl)-2,6-dimethyl-1,4-dihydropyridine-3,5-dicarboxylate:

250 mg (0.69 mmol) of mono(2-cyanoethyl) 4-(3-chlorophenyl-2,6-dimethyl-1,4-dihydropyridine-3,5-dicarboxylate, 0.1 ml (0.8 mmol) of 2-phenyloxyethanol, 187 mg (0.98 mmol) of 1-(3-dimethylaminopropyl)-3-ethylcarbodiimide hydrochloride and 18 mg (0.15 mmol) of 4-dimethylaminopyridine were stirred at room temperature for 2 days. Water was added to the obtained mixture. After the extraction with chloroform, the organic layer was dried over anhydrous magnesium sulfate. The solvent was evaporated under reduced pressure, and the residue was purified by the silica gel chromatography (hexane/ethyl acetate=2/1) to obtain the title compound.

Yield: 168 mg (0.35 mmol) (50.3%).
MS (ESI, m/z) 479 (M–H)$^-$
$^1$H-NMR (CDCl$_3$): 2.34 (3H, s), 2.37 (3H, s), 2.56 (2H, t), 4.08–4.28 (4H, m), 4.33–4.48 (2H, m), 4.99 (1H, s), 5.73 (1H, s), 6.88–7.11 (4H, m), 7.17–7.23 (2H, m), 7.26–7.33 (3H, m)

3) Synthesis of mono(2-phenyloxyethyl) 4-(3-chlorophenyl)-2,6-dimethyl-1,4-dihydropyridine-3,5-dicarboxylate:

The title compound was obtained from 161 mg (0.33 mmol) of 5-(2-phenyloxyethyl) 3-(2-cyanoethyl) 4-(3-chlorophenyl)-2,6-dimethyl-1,4-dihydropyridine-3,5-dicarboxylate in the same manner as that of Example 3-2).

Yield: 109 mg (0.25 mmol) (77.2%)
MS (ESI, m/z) 426 (M–H)$^-$
$^1$H-NMR (DMSO-d$_6$): 2.25 (3H, s), 2.27 (3H, s), 4.02–4.38 (4H, m), 4.88 (1H, s), 6.91–6.99 (3H, m), 7.10–7.18 (4H, m), 7.29 (2H, t), 8.84 (1H, s)

EXAMPLE 48

Synthesis of mono(4-phenylbutyl) 4-(3-chlorophenyl)-2,6-dimethyl-1,4-dihydropyridine-3,5-dicarboxylate 1) Synthesis of 5-(4-phenylbutyl) 3-(2-cyanoethyl) 4-(3-chlorophenyl)-2,6-dimethyl-1,4-dihydropyridine 3,5-dicarboxylate:

259 mg (0.718 mmol) of mono(2-cyanoethyl) 4-(3-chlorophenyl)-2,6-dimethyl-1,4-dihydropyridine-3,5-dicarboxylate, 0.122 ml (0.79 mmol) of 4-phenylbutyl alcohol, 193 mg (1.01 mmol) of 1-(3-dimethylaminopropyl)-3-ethylcarbodiimide hydrochloride and 17.5 mg (0.144 mmol) of 4-dimethylaminopyridine were stirred together in 7.2 ml of dichloromethane at room temperature overnight. Water was added to the reaction liquid. After the extraction with chloroform, the organic layer was dried over anhydrous sodium sulfate. The solvent was evaporated under reduced pressure, and the residue was purified by the silica gel chromatography (hexane/ethyl acetate=1/1) to obtain the title compound.

Yield: 135.5 mg (0.275 mmol) (38%).
MS (ESI, m/z) 491 (M–H)$^-$
$^1$H-NMR (CDCl$_3$): 1.54–1.76 (4H, m), 2.33 (6H, s), 2.54–2.70 (2H, m), 3.97–4.14 (2H, m), 4.14–4.30 (2H, m), 4.95 (1H, s), 5.86 (1H, bs), 7.10–7.30 (9H, m)

2) Synthesis of mono(4-phenylbutyl) 4-(3-chlorophenyl)-2,6-dimethyl-1,4-dihydropyridine-3,5-dicarboxylate:

135.5 mg (0.275 mmol) of 5-(4-phenylbutyl) 3-(2-cyanoethyl) 4-(3-chlorophenyl)-2,6-dimethyl-1,4-dihydropyridine-3,5-dicarboxylate was dissolved in 2.75 ml of tetrahydrofuran. 0.55 ml of 1 N aqueous sodium hydroxide solution was added to the obtained solution, and they were stirred at room temperature for 16 hours. 2 N Hydrochloric acid was added to the reaction mixture, and then tetrahydrofuran was evaporated under reduced pressure. After the extraction with ethyl acetate, the organic layer was dried over anhydrous sodium sulfate and then concentrated under reduced pressure. The residue was washed with hexane/ethyl acetate (5:1) and then dried under reduced pressure to obtain the title compound.

Yield: 42.3 mg (0.0961 mmol) (35%).
MS (ESI, m/z) 438 (M–H)$^-$
$^1$H-NMR (DMSO-d$_6$): 1.45–1.55 (4H, m), 2.24 (3H, s), 2.26 (3H, s), 2.45–2.55 (2H, m), 3.92–4.08 (2H, m), 4.86 (1H, s), 7.07–7.30 (9H, m), 8.77 (1H, bs)

EXAMPLE 49

Synthesis of mono(3-phenyl-2-propene-1-yl) 4-(3-hydroxyphenyl)-2,6-dimethyl-1,4-dihydropyridine-3,5-dicarboxylate 1) Synthesis of 5-(3-phenyl-2-propene-1-yl) 3-(2-cyanoethyl) 4-(3-hydroxyphenyl)-2,6-dimethyl-1,4-dihydropyridine-3,5-dicarboxylate:

The title compound was obtained from 454 mg (2.92 mmol) of 2-cyanoethyl acetoacetate, 641 mg (2.95 mmol) of cinnamyl 3-aminocrotonate and 358 mg (2.93 mmol) of 3-hydroxybenzaldehyde in the same manner as that of Example 1-1).

Yield: 651 mg (1.42 mmol) (48.7%)

MS (ESI, m/z) 457 (M–H)⁻

$^1$H-NMR (CDCl$_3$): 2.32 (3H, s), 2.37 (3H, s), 2.67 (2H, t) 4.16–4.42 (2H, m), 4.62–4.82 (2H, m), 4.99 (1H, s), 5.78 (1H, s), 6.23 (1H, dt), 6.51 (1H, d), 6.66 (1H, dd), 6.82 (1H, d), 6.94 (1H, m), 7.09 (1H, t), 7.20–7.38 (5H, m)

2) Synthesis of mono(3-phenyl-2-propene-1-yl) 4-(3-hydroxyphenyl)-2,6-dimethyl-1,4-dihydropyridine-3,5-dicarboxylate:

The title compound was obtained from 541 mg (1.18 mmol) of 5-(3-(phenyl-2-propene-1-yl) 3-(2-cyanoethyl) 4-(3-hydroxyphenyl)-2,6-dimethyl-1,4-dihydropyridine-3,5-dicarboxylate in the same manner as that of Example 3–2).

Yield: 358 mg (0.88 mmol) (74.6%)

MS (ESI, m/z) 404 (M–H)⁻

$^1$H-NMR (DMSO-d$_6$): 2.24 (3H, s), 2.29 (3H, s), 4.60–4.77 (2H, s), 4.89 (1H, s), 6.33 (1H, dt), 6.46–6.55 (2H, m), 6.60–6.66 (2H, m), 6.97 (1H, t), 7.22–7.42 (5H, m), 8.75 (1H, s), 9.12 (1H, s)

EXAMPLE 50

Synthesis of mono(3-phenyloxypropyl) 4-(3-chlorophenyl)-2,6-dimethyl-1,4-dihydropyridine-3,5-dicarboxylate 1) Synthesis of 5-(3-phenyloxypropyl) 3-(2-cyanoethyl) 4-(3-chlorophenyl)-2,6-dimethyl-1,4-dihydropyridine-3,5-dicarboxylate:

250 mg (0.69 mmol) of mono(2-cyanoethyl) 4-(3-chlorophenyl)-2,6-dimethyl-1,4-dihydropyridine-3,5-dicarboxylate, 130 mg (0.85 mmol) of 3-phenyloxypropanol, 162 mg (0.84 mmol) of 1-(3-dimethylaminopropyl)-3-ethylcarbodiimide hydrochloride and 21 mg (0.17 mmol) of 4-dimethylaminopyridine were stirred together in 10 ml of dichloromethane at room temperature overnight. Water was added to the reaction liquid. After the extraction with dichloromethane, the organic layer was dried over anhydrous sodium sulfate. The solvent was evaporated under reduced pressure, and the residue was purified by the silica gel chromatography (hexane/ethyl acetate=2/1) to obtain the title compound.

Yield: 195 mg (0.39 mmol) (57.0%).

MS (ESI, m/z) 493 (M–H)⁻

$^1$H-NMR (CDCl$_3$): 2.04–2.13 (2H, m), 2.35 (3H, s), 2.36 (3H, s), 2.57–2.63 (2H, m), 3.88–3.96 (2H, m), 4.18–4.35 (4H, m), 4.94 (1H, s), 6.68 (1H, s), 6.82–6.98 (3H, m), 7.08–7.38 (6H, m)

2) Synthesis of mono(3-phenyloxypropyl) 4-(3-chlorophenyl)-2,6-dimethyl-1,4-dihydropyridine-3,5-dicarboxylate:

The title compound was obtained from 195 mg (0.39 mmol) of 5-(3-phenyloxypropyl) 3-(2-cyanoethyl) 4-(3-chlorophenyl)-2,6-dimethyl-1,4-dihydropyridine-3,5-dicarboxylate in the same manner as that of Example 3-2).

Yield: 104 mg (0.23 mmol) (59.5%).

MS (ESI, m/z) 440 (M–H)⁻

$^1$H-NMR (DMSO-d$_6$): 1.95–2.02 (2H, m), 2.24 (3H, s), 2.27 (3H, s), 3.82–3.94 (2H, m), 4.02–4.20 (2H, m), 4.87 (1H, s), 6.81–6.96 (3H, m), 7.08–7.36 (6H, m), 8.83 (1H, s)

EXAMPLE 51

Synthesis of mono(2-phenylcyclopropylmethyl) 4-(3-chlorophenyl)-2,6-dimethyl-1,4-dihydropyridine-3,5-dicarboxylate 1) Synthesis of 5-(2-phenylcyclopropylmethyl) 3-(2-cyanoethyl) 4-(3-chlorophenyl)-2,6-dimethyl-1,4-dihydropyridine 3,5-dicarboxylate:

306 mg (0.85 mmol) of mono(2-cyanoethyl) 4-(3-chlorophenyl)-2,6-dimethyl-1,4-dihydropyridine-3,5-dicarboxylate, 188 mg (1.27 mmol) of 2-phenylcyclopropylmethanol, 243 mg (1.27 mmol) of 1-(3-dimethylaminopropyl)-3-ethylcarbodiimide hydrochloride and 23 mg (0.18 mmol) of 4-dimethylaminopyridine were stirred together in 10 ml of dichloromethane at room temperature for one hour. Water was added to the reaction liquid. After the extraction with dichloromethane, the organic layer was dried over anhydrous sodium sulfate. The solvent was evaporated under reduced pressure, and the residue was purified by the silica gel chromatography (hexane/ethyl acetate=2/1) to obtain the title compound.

Yield: 187 mg (0.38 mmol) (44.7%).

MS (ESI, m/z) 489 (M–H)⁻

$^1$H-NMR (CDCl$_3$) 0.84–1.02 (2H, m), 1.42–1.52 (1H, m), 1.79–1.88 (1H, m), 2.35 (3H, s), 2.37 (3H, s), 2.56 (2H, t), 3.96–4.12 (2H, m), 4.18–4.30 (2H, m), 4.99 (1H, s), 5.70 (1H, s), 7.00–7.33 (9H, m)

2) Synthesis of mono(3-phenylcyclopropylmethyl) 4-(3-chlorophenyl)-2,6-dimethyl-1,4-dihydropyridine-3,5-dicarboxylate:

The title compound was obtained from 181 mg (0.37 mmol) of 5-(2-phenylcyclopropylmethyl) 3-(2-cyanoethyl) 4-(3-chlorophenyl)-2,6-dimethyl-1,4-dihydropyridine-3,5-dicarboxylate in the same manner as that of Example 3-2).

Yield: 41 mg (0.09 mmol) (25.3%).

MS (ESI, m/z) 436 (M–H)⁻

$^1$H-NMR (DMSO-d$_6$): 0.78–1.00 (2H, m), 1.31–1.43 (1H, m), 1.82–1.92 (1H, m), 2.26 (6H, s), 3.88–4.08 (2H, m), 4.90 (1H, s), 7.01–7.32 (9H, m), 8.81 (1H, s)

EXAMPLE 52

Synthesis of 3-(3-phenyl-2-propene-1-yl) 4-(3-chlorophenyl)-2-ethyl-6-methyl-1,4-dihydropyridine-3,5-dicarboxylate 1) Synthesis of (3-phenyl-2-propene-1-yl) 3-oxovalerate:

1.26 ml (10.0 mmol) of methyl 3-oxovalerate, 2.57 ml (20.0 mmol) of cinnamyl alcohol and 122 mg (1.0 mmol) of 4-dimethylaminopyridine were heated under reflux in 20 ml of toluene overnight. A phosphate buffer solution was added to the reaction liquid. After the extraction with ethyl acetate, the organic layer was washed with saturated aqueous salt solution and then dried over anhydrous sodium sulfate. The solvent was evaporated under reduced pressure, and the residue was purified by the silica gel chromatography (hexane/ethyl acetate=9/1) to obtain the title compound.

Yield: 1.94 g (8.36 mmol) (84%).

MS (ESI, m/z) 231 (M–H)⁻

$^1$H-NMR (CDCl$_3$): 1.09 (3H, t), 2.57 (2H, d), 3.49 (2H, s), 4.80 (2H, d), 6.28 (1H, dt), 6.67 (1H, d), 7.23–7.42 (5H, m)

2) Synthesis of 3-(3-phenyl-2-propene-1-yl) 5-(2-cyanoethyl) 4-(3-chlorophenyl)-2-ethyl-6-methyl-1,4-dihydropyridine-3,5-dicarboxylate:

465 mg (2.0 mmol) of (3-phenyl-2-propene-1-yl) 3-oxovalerate, 309 mg (2.0 mmol) of (2-cyanoethyl) 3-aminocrotonate and 0.227 ml (2.0 mmol) of 3-chlorobenzaldehyde were heated at 70° C. under stirring in 10 ml of 2-propanol overnight. The reaction mixture was further heated at 120° C. under stirring under atmospheric pressure for 3 hours to evaporate 2-propanol. The residue was purified by the silica gel chromatography (hexane/ethyl acetate=2/1) to obtain the title compound.

Yield: 494 g (1.01 mmol) (50%).

MS (ESI, m/z) 489 (M–H)⁻

$^1$H-NMR (CDCl$_3$): 1.19–1.29 (3H, m), 2.37 (3H, s), 2.62 (2H, t), 2.65–2.87 (2H, m), 4.19–4.33 (2H, m), 4.64–4.80 (2H, m), 5.01 (1H, s), 5.82 (1H, bs), 6.23 (1H, dt), 6.53 (1H, d), 7.08–7.38 (9H, m)

3) Synthesis of 3-(3-phenyl-2-propene-1-yl) 4-(3-chlorophenyl)-2-ethyl-6-methyl-1,4-dihydropyridine-3,5-dicarboxylate:

494 mg (1.01 mmol) of 3-(3-phenyl-2-propene-1-yl) 5-(2-cyanoethyl) 4-(3-chlorophenyl)-2-ethyl-6-methyl-1,4-dihydropyridine-3,5-dicarboxylate was dissolved in 10.1 ml of methanol. 1.01 ml of 1 N aqueous sodium hydroxide solution was added to the obtained solution, and they were stirred at room temperature for 4 hours. 2 N Hydrochloric acid was added to the reaction mixture. Methanol was evaporated under reduced pressure. After the extraction with ethyl acetate, the organic layer was dried over anhydrous sodium sulfate and then concentrated under reduced pressure. The residue was washed with hexane/ethyl acetate (5:1) and dried under reduced pressure to obtain the title compound.

Yield: 329 mg (1.61 mmol) (74%).

MS (ESI, m/z) 436 (M–H)⁻

$^1$H-NMR (DMSO-d$_6$): 1.10–1.20 (3H, m), 2.26 (3H, s), 2.63–2.80 (2H, m), 4.58–4.77 (2H, m), 4.93 (1H, s), 6.34 (1H, dt), 6.50 (1H, d), 7.10–7.41 (9H, m), 8.85 (1H, bs)

EXAMPLE 53

Synthesis of mono(3,3-diphenyl-2-propene-1-yl) 4-(3-chlorophenyl)-2,6-dimethyl-1,4-dihydropyridine-3,5-dicarboxylate 1) Synthesis of 5-(3,3-diphenyl-2-propene-1-yl) 3-(2-cyanoethyl) 4-(3-chlorophenyl)-2,6-dimethyl-1,4-dihydropyridine-3,5-dicarboxylate:

308 mg (0.85 mmol) of mono(2-cyanoethyl) 4-(3-chlorophenyl)-2,6-dimethyl-1,4-dihydropyridine-3,5-dicarboxylate, 348 mg (1.65 mmol) of 3,3-diphenyl-2-propene-1-ol, 260 mg (1.36 mmol) of 1-(3-dimethylaminopropyl)-3-ethylcarbodiimide hydrochloride and 26 mg (0.21 mmol) of 4-dimethylaminopyridine were stirred together in 10 ml of dichloromethane at room temperature for one hour. Water was added to the reaction liquid. After the extraction with dichloromethane, the organic layer was dried over anhydrous sodium sulfate. The solvent was evaporated under reduced pressure, and the residue was purified by the silica gel chromatography (hexane/ethyl acetate=2/1) to obtain the title compound.

Yield: 116 mg (0.21 mmol) (24.6%).

MS (ESI, m/z) 551 (M–H)⁻ $^1$H-NMR (CDCl$_3$): 2.36 (3H, s), 2.37 (3H, s), 2.63 (2H, t), 4.20–4.34 (2H, m), 4.54–4.68 (2H, m), 4.99 (1H, s), 5.69 (1H, s), 6.13 (1H, t), 7.09–7.36 (14H, m)

2) Synthesis of mono(3,3-diphenyl-2-propene-1-yl) 4-(3-chlorophenyl)-2,6-dimethyl-1,4-dihydropyridine-3,5-dicarboxylate:

The title compound was obtained from 112 mg (0.21 mmol) of 5-(3,3-diphenyl-2-propene-1-yl) 3-(2-cyanoethyl) 4-(3-chlorophenyl)-2,6-dimethyl-1,4-dihydropyridine-3,5-dicarboxylate in the same manner as that of Example 3-2).

Yield: 27 mg (0.05 mmol) (25.6%).

MS (ESI, m/z) 498 (M–H)⁻

$^1$H-NMR (DMSO-d$_6$): 2.25 (3H, s), 2.27 (3H, s), 4.47 (2H, m), 4.89 (1H, s), 6.13 (1H, t), 7.05–7.42 (14H, m), 8.84 (1H, s)

EXAMPLE 54

Synthesis of 5-(3-phenyl-2-propene-1-yl) 4-(3-chlorophenyl)-2-methyl-1,4-dihydropyridine-3,5-dicarboxylate 1) Synthesis of (3-phenyl-2-propene-1-yl) propiolate:

2.71 mg (44 mmol) of propiolic acid and 5.14 ml (40 mmol) of cinnamyl alcohol were dissolved in 20 ml of dry ether. The obtained solution was cooled to –20° C. 100 ml of a solution of 9.27 g (45 mmol) of dicyclohexylcarbodiimide and 0.36 g (30 mmol) of 4-dimethylaminopyridine in dry ether was dropped into the solution. The temperature of the obtained mixture was elevated to room temperature. After stirring overnight, the insoluble matter was filtered out. The filtrate was washed with 2 N hydrochloric acid and saturated aqueous salt solution, and then dried over anhydrous sodium sulfate. The solvent was evaporated under reduced pressure, and the residue was purified by the silica gel chromatography (hexane/ethyl acetate=10/1) to obtain the title compound.

Yield: 4.78 g (25.7 mmol) (64%).

$^1$H-NMR (CDCl$_3$): 2.89 (1H, s), 4.84 (2H, d), 6.28 (1H, dt), 6.70 (1H, d), 7.23–7.42 (5H, m)

2) Synthesis of 5-(3-phenyl-propene-1-yl) 3-(2-cyanoethyl) 4-(3-chlorophenyl)-2-methyl-1,4-dihydropyridine-3,5-dicarboxylate:

466 mg (3.0 mmol) of (2-cyanoethyl) acetoacetate, 0.34 ml (3.0 mmol) of 3-chlorobenzaldehyde and 0.0297 ml of piperidine were heated under reflux in 3.0 ml of benzene for 7 hours while water was removed. The reaction liquid was washed with water and then dried over anhydrous magnesium sulfate. The solvent was evaporated under reduced pressure. The obtained residue was heated to 70° C together with 559 mg (3.0 mmol) of (3-phenyl-2-propene-1-yl) propiolate and 232 mg (3.0 mmol) of ammonium acetate under stirring in 3 ml of acetic acid for 13 hours, then at 120° C. under stirring for 4 hours. Acetic acid was evaporated under reduced pressure, and the residue was purified by the silica gel chromatography (hexane/ethyl acetate=1/1) to obtain the title compound.

Yield: 257 mg (0.556 mmol) (19%).

MS (ESI, m/z) 461 (M–H)⁻

$^1$H-NMR (CDCl$_3$): 2.34 (3H, s), 2.58 (2H, t), 4.18–4.31 (2H, m), 4.61–4.81 (2H, m), 4.94 (1H, s), 6.21 (1H, dt), 6.48 (1H, bs), 6.53 (1H, d), 7.10–7.41 (10H, m)

3) Synthesis of 5-(3-phenyl-2-propene-1-yl) 4-(3-chlorophenyl)-2-methyl-1,4-dihydropyridine-3,5-dicarboxylate:

257 mg (0.556 mmol) of 5-(3-phenyl-2-propene-1-yl) 3-(2-cyanoethyl) 4-(3-chlorophenyl)-2-methyl-1,4-dihydropyridine-3,5-dicarboxylate was dissolved in 5.56 ml of methanol. 0.556 ml of 1 N aqueous sodium hydroxide solution was added to the obtained solution, and they were stirred at room temperature for 7 hours. 2 N hydrochloric acid was added to the reaction mixture, and methanol was evaporated under reduced pressure. After the extraction with ethyl acetate, the organic layer was dried over anhydrous sodium sulfate and then concentrated under reduced pressure. The residue was washed with hexane/ethyl acetate (5:1) to obtain the title compound.

Yield: 68 mg (0.166 mmol) (30%).
MS (ESI, m/z) 408 (M−H)−
$^1$H-NMR (DMSO-$d_6$): 2.26 (3H, s), 4.60–4.78 (2H, m), 4.83 (1H, s), 6.33 (1H, dt), 6.54 (1H, d), 7.13–7.43 (10H, m), 9.19 (1H, bd)

EXAMPLE 55

Synthesis of mono(3-phenyl-2-propene-1-yl) 4-(3-chlorophenyl)-1,4-dihydropyridine-3,5-dicarboxylate 1) Synthesis of (2-cyanoethyl) propiolate:

2.71 mg (44 mmol) of propiolic acid and 2.73 ml (40 mmol) of 2-cyanoethanol were dissolved in 20 ml of dry ether. The obtained solution was cooled to −20° C. 100 ml of a solution of 9.27 g (45 mmol) of dicyclohexylcarbodiimide and 0.36 g (30 mmol) of 4-dimethylaminopyridine in dry ether was dropped into the solution. The temperature of the obtained mixture was elevated to room temperature. After stirring overnight, the insoluble matter was filtered out. The filtrate was washed with 2 N hydrochloric acid and saturated aqueous salt solution, and then dried over anhydrous sodium sulfate. The solvent was evaporated under reduced pressure, and the residue was purified by the silica gel chromatography (ethyl acetate) to obtain the title compound.

Yield: 1.80 g (14.6 mmol) (37%).
$^1$H-NMR (CDCl$_3$): 2.75 (2H, t), 3.02 (1H, s), 4.36 (2H, t)

2) Synthesis of 5-(3-phenyl-2-propene-1-yl) 3-(2-cyanoethyl) 4-(3-chlorophenyl)-1,4-dihydropyridine-3,5-dicarboxylate:

493 mg (4.0 mmol) of (2-cyanoethyl) propiolate, 745 ml (4.0 mmol) of (3-phenyl-2-propene-1-yl) propiolate, 0.453 ml (4.0 mmol) of 3-chlorobenzaldehyde and 617 mg (8.0 mmol) of ammonium acetate were heated at 60° C. under stirring in 8 ml of acetic acid for 12 hours. Acetic acid was evaporated under reduced pressure, and the residue was purified by the silica gel chromatography (hexane/ethyl acetate=1/1) to obtain the title compound.

Yield: 104 mg (0.231 mmol) (6%).
MS (ESI, m/z) 447 (M−H)−
$^1$H-NMR (CDCl$_3$): 2.62 (2H, t), 4.18–4.32 (2H, m), 4.61–4.81 (2H, m), 4.92 (1H, s), 6.20 (1H, dt), 6.52 (1H, bs), 7.10–7.43 (12H, m)

3) Synthesis of mono(3-phenyl-2-propene-1-yl) 4-(3-chlorophenyl)-1,4-dihydropyridine-3,5-dicarboxylate:

104 mg (0.231 mmol) of 5-(3-phenyl-propene-1-yl) 3-(2-cyanoethyl) 4-(3-chlorophenyl)-1,4-dihydropyridine-3,5-dicarboxylate was dissolved in 2.3 ml of methanol. 0.231 ml of 1 N aqueous sodium hydroxide solution was added to the obtained solution, and they were stirred at room temperature for 2 hours. 2 N hydrochloric acid was added to the reaction mixture, and methanol was evaporated under reduced pressure. After the extraction with ethyl acetate, the organic layer was dried over anhydrous sodium sulfate and then concentrated under reduced pressure. The residue was washed with hexane/ethyl acetate (3:1) and dried under reduced pressure to obtain the title compound.

Yield: 62 mg (0.157 mmol) (68%)

MS (ESI, m/z) 394 (M−H)−
$^1$H-NMR (DMSO-$d_6$): 4.59–4.73 (2H, m), 4.76 (1H, s), 6.32 (1H, dt), 6.52 (1H, d), 7.10–7.30 (11H, m), 9.18 (1H, bt)

EXAMPLE 56

Synthesis of 3-(3-phenyl-2-propene-1-yl) 4-(3-chlorophenyl)-2-methyl-1,4-dihydropyridine-3,5-dicarboxylate 1) Synthesis of 3-(3-phenyl-2-propene-1-yl) 5-(2-cyanoethyl) 4-(3-chlorophenyl)-2-methyl-1,4-dihydropyridine-3,5-dicarboxylate:

655 mg (3.0 mmol) of cinnamyl acetoacetate, 0.34 ml (3.0 mmol) of 3-chlorobenzaldehyde and 0.0297 ml of piperidine were heated under reflux in 3.0 ml of benzene overnight while water was removed. The reaction liquid was washed with water and then dried over anhydrous magnesium sulfate. The solvent was evaporated under reduced pressure. The obtained residue was heated to 70° C. together with 370 mg (3.0 mmol) of (2-cyanoethyl) propiolate and 232 mg (3.0 mmol) of ammonium acetate under stirring in 3 ml of acetic acid for two nights. Acetic acid was evaporated under reduced pressure, and the residue was purified by the silica gel chromatography (hexane/ethyl acetate=3/2) to obtain the title compound.

Yield: 271 mg (0.587 mmol) (20%).
MS (ESI, m/z) 461 (M−H)−
$^1$H-NMR (CDCl$_3$): 2.37 (3H, s), 2.63 (2H, t), 4.14–4.34 (2H, m), 4.61–4.77 (2H, m), 4.97 (1H, s), 6.19 (1H, dt), 6.27 (1H, bd), 6.51 (1H, d), 7.09–7.37 (10H, m)

2) Synthesis of 3-(3-phenyl-2-propene-1-yl) 4-(3-chlorophenyl)-2-methyl-1,4-dihydropyridine-3,5-dicarboxylate:

The title compound was obtained from 271 mg (0.587 mmol) of 3-(3-phenyl-2-propene-1-yl) 5-(2-cyanoethyl) 4-(3-chlorophenyl)-2-methyl-1,4-dihydropyridine-3,5-dicarboxylate Yield: 144 mg (0.351 mmol) (60%).
MS (ESI, m/z) 408 (M−H)−
$^1$H-NMR (DMSO-$d_6$): 2.30 (3H, s), 4.58–4.74 (2H, m), 4.85 (1H, s), 6.30 (1H, dt), 6.49 (1H, d), 7.08–7.43 (10H, m), 9.21 (1H, bd)

EXAMPLE 57

Synthesis of mono(3-phenyl-2-propene-1-yl) 2,6-dimethyl-4-(4-methoxyphenyl)-1,4-dihydropyridine-3,5-dicarboxylate 1) Synthesis of 5-(3-phenyl-2-propene-1-yl) 3-(2-cyanoethyl) 2,6-dimethyl-4-(4-methoxyphenyl)-1,4-dihydropyridine-3,5-dicarboxylate:

The title compound was obtained from 311 mg (2.00 mmol) of 2-cyanoethyl acetoacetate, 437 mg (2.01 mmol) of cinnamyl 3-aminocrotonate and 0.245 ml (2.01 mmol) of 4-methoxybenzaldehyde in the same manner as that of Example 1-1).

Yield: 259 mg (0.55 mmol) (27.4%).
MS (ESI, m/z) 471 (M−H)−
$^1$H-NMR (CDCl$_3$) 2.35 (3H, s), 2.36 (3H, s), 2.61 (2H, t), 3.73 (3H, s), 4.20–4.31 (2H, m), 4.63–4.83 (2H, m), 4.97 (1H, s), 5.63 (1H, s), 6.22 (1H, dt), 6.48 (1H, d), 6.74 (2H, d), 7.22 (2H, d), 7.24–7.34 (5H, m)

2) Synthesis of mono(3-phenyl-2-propene-1-yl) 2,6-dimethyl-4-(4-methoxyphenyl)-1,4-dihydropyridine-3,5-dicarboxylate:

The title compound was obtained from 259 mg (0.55 mmol) of 5-(3-phenyl-2-propene-1-yl) 3-(2-cyanoethyl) 2,6-dimethyl-4-(4-methoxyphenyl)-1,4-dihydropyridine-3,5-dicarboxylate in the same manner as that of Example 3-2).

Yield: 138 mg (0.33 mmol) (60.0%).
MS (ESI, m/z) 418 (M−H)⁻
$^1$H-NMR (DMSO-$d_6$): 2.24 (3H, s), 2.28 (3H, s), 3.66 (3H, s), 4.56–4.77 (2H, m), 4.87 (1H, s), 6.30 (1H, dt), 6.44 (1H, d), 6.75 (2H, d), 7.08 (2H, d), 7.22–7.39 (5H, m), 8.72 (1H, s)

EXAMPLE 58

Synthesis of mono(3-phenyl-2-propene-1-yl) 2,6-dimethyl-4-(4-methylphenyl)-1,4-dihydropyridine-3,5-dicarboxylate 1) Synthesis of 5-(3-phenyl-2-propene-1-yl) 3-(2-cyanoethyl) 2,6-dimethyl-4-(4-methylphenyl)-1,4-dihydropyridine-3,5-dicarboxylate:

The title compound was obtained from 316 mg (2.04 mmol) of 2-cyanoethyl acetoacetate, 439 mg (2.02 mmol) of cinnamyl 3-aminocrotonate and 0.235 ml (1.99 mmol) of 4-methylbenzaldehyde in the same manner as that of Example 1-1).

Yield: 350 mg (0.77 mmol) (38.6%).
MS (ESI, m/z) 455 (M−H)⁻
$^1$H-NMR (CDCl$_3$): 2.27 (3H, s), 2.35 (3H, S); 2.36 (3H, s), 2.61 (2H, t), 4.20–4.30 (2H, m), 4.63–4.82 (2H, m), 4.99 (1H, s), 5.64 (1H, s), 6.22 (1H, dt), 6.47 (1H, d), 7.02 (2H, d), 7.20 (2H, d), 7.23–7.34 (5H, m)

2) Synthesis of mono(3-phenyl-2-propene-1-yl) 2,6-dimethyl-4-(4-methylphenyl)-1,4-dihydropyridine-3,5-dicarboxylate:

The title compound was obtained from 340 mg (0.75 mmol) of 5-(3-phenyl-2-propene-1-yl) 3-(2-cyanoethyl) 2,6-dimethyl-4-(4-methylphenyl)-1,4-dihydropyridine-3,5-dicarboxylate in the same manner as that of Example 3-2).

Yield: 226 mg (0.56 mmol) (75.2%).
MS (ESI, m/z) 402 (M−H)⁻
$^1$H-NMR (DMSO-$d_6$): 2.20 (3H, s), 2.23 (3H, s), 2.28 (3H, s), 4.56–4.76 (2H, m), 4.90 (1H, s), 6.30 (1H, dt), 6.43 (1H, d), 6.99 (2H, d), 7.06 (2H, d), 7.22–7.38 (5H, m), 8.74 (1H, s)

EXAMPLE 59

Synthesis of mono(3-phenyl-2-propene-1-yl) 2,6-dimethyl-4-(pyridine-4-yl)-1,4-dihydropyridine-3,5-dicarboxylate 1) Synthesis of (3-phenyl-2-propene-1-yl) 3-(2-cyanoethyl) 2,6-dimethyl-4-(pyridine-4-yl)-1,4-dihydropyridine-3,5-dicarboxylate:

The title compound was obtained from 465 mg (3.00 mmol) of 2-cyanoethyl acetoacetate, 655 mg (3.01 mmol) of cinnamyl 3-aminocrotonate and 0.285 ml (2.99 mmol) of 4-pyridylaldehyde in the same manner as that of Example 1-1).

Yield: 776 mg (1.75 mmol) (58.5%).
MS (ESI, m/z) 442 (M−H)⁻
$^1$H-NMR (CDCl$_3$): 2.38 (6H, s), 2.63 (2H, dt), 4.27 (2H, dt), 4.66–4.82 (2H, m), 5.05 (1H, s), 5.96 (1H, s), 6.23 (1H, dt), 6.54 (1H, d), 7.23 (2H, d), 7.24–7.38 (5H, m), 8.45 (2H, d)

2) Synthesis of mono(3-phenyl-2-propene-1-yl) 2,6-dimethyl-4-(pyridine-4-yl)-1,4-dihydropyridine-3,5-dicarboxylate:

The title compound was obtained from 498 mg (1.12 mmol) of (3-phenyl-2-propene-1-yl) 3-(2-cyanoethyl) 2,6-dimethyl-4-(pyridine-4-yl)-1,4-dihydropyridine-3,5-dicarboxylate in the same manner as that of Example 3-2).

Yield: 351 mg (0.90 mmol) (80.3%).
MS (ESI, m/z) 389 (M−H)⁻
$^1$H-NMR (DMSO-$d_6$): 2.27 (3H, s), 2.31 (3H, s), 4.61–4.77 (2H, m), 4.95 (1H, s), 6.33 (1H, dt), 6.50 (1H, d), 7.16 (2H, dd), 7.22–7.42 (5H, m), 8.40 (2H, dd), 8.94 (1H, s)

EXAMPLE 60

Synthesis of (3-phenyl-2-propene-1-yl) 5-acetyl-4-(3-chlorophenyl)-2,6-dimethyl-1,4-dihydropyridine-3-carboxylate The title compound was obtained from 0.21 ml (2.05 mmol) of acetylacetone, 442 mg (2.04 mmol) of cinnamyl 3-aminocrotonate and 0.23 ml (2.03 mmol) of 3-chlorobenzaldehyde in the same manner as that of Example 1-1).

Yield: 383 mg (0.91 mmol) (44.7%).
MS (ESI, m/z) 420 (M−H)⁻
$^1$H-NMR (CDCl$_3$): 2.17 (3H, s), 2.33 (3H, s), 2.37 (3H, s), 4.70–4.88 (2H, m), 5.05 (1H, s), 5.72 (1H, s), 6.30 (1H, dt), 6.62 (1H, d), 7.11–7.20 (3H, m), 7.23–7.41 (6H, m)

EXAMPLE 61

Synthesis of mono(3-phenyl-2-propene-1-yl) 2,6-dimethyl-4-(pyridine-2-yl)-1,4-dihydropyridine-3,5-dicarboxylate 1) Synthesis of 5-(3-phenyl-2-propene-1-yl) 3-(2-cyanoethyl) 2,6-dimethyl-4-(pyridine-2-yl)-1,4dihydropyridine-3,5-dicarboxylate:

The title compound was obtained from 472 mg (3.03 mmol) of 2-cyanoethyl acetoacetate, 660 mg (3.04 mmol) of cinnamyl 3-aminocrotonate and 0.285 ml (3.00 mmol) of 2-pyridylaldehyde in the same manner as that of Example 1-1).

Yield: 484 mg (1.09 mmol) (36.3%).
MS (ESI, m/z) 442 (M−H)⁻
$^1$H-NMR (CDCl$_3$): 2.28 (6H, s), 2.60 (2H, dt), 4.15–4.33 (2H, m), 4.62–4.78 (2H, m), 5.23 (1H, s), 6.22 (1H, dt), 6.52 (1H, d), 7.11–7.17 (1H, m), 7.22–7.38 (6H, m), 7.45 (1H, d), 7.57 (1H, dt), 8.50 (1H, d)

2) Synthesis of mono(3-phenyl-2-propene-1-yl) 2,6-dimethyl-4-(pyridine-2-yl)-1,4-dihydropyridine-3,5-dicarboxylate:

The title compound was obtained from 468 mg (1.06 mmol) of 5-(3-phenyl-2-propene-1-yl) 3-(2-cyanoethyl) 2,6-dimethyl-4-(pyridine-2-yl)-1,4-dihydropyridine-3,5-dicarboxylate in the same manner as that of Example 3-2).

Yield: 305 mg (0.78 mmol) (74.0%).
MS (ESI, m/z) 389 (M−H)⁻
$^1$H-NMR (DMSO-$d_6$): 2.23 (3H, s), 2.27 (3H, s), 4.58–4.77 (2H, m), 5.09 (1H, s), 6.31 (1H, dt), 6.52 (1H, d), 7.08–7.42 (7H, m), 7.59 (1H, dt), 8.42 (1H, d), 8.75 (1H, s)

EXAMPLE 62

Synthesis of mono(3-phenyl-2-propene-1-yl) 4-(4-bromophenyl)-2,6-dimethyl-1,4-dihydropyridine-3,5-dicarboxylate 1) Synthesis of 5-(3-phenyl-2-propene-1-yl) 3-(2-cyanoethyl) 4-(4-bromophenyl)-2,6-dimethyl-1,4-dihydropyridine-3,5-dicarboxylate:

The title compound was obtained from 406 mg (2.62 mmol) of 2-cyanoethyl acetoacetate, 566 mg (2.60 mmol) of cinnamyl 3-aminocrotonate and 488 mg (2.64 mmol) of 4-bromobenzaldehyde in the same manner as that of Example 1-1).

Yield: 709 mg (1.36 mmol) (52.3%).
MS (ESI, m/z) 519 (M−H)−
$^1$H-NMR (CDCl$_3$): 2.25 (3H, s), 2.36 (3H, s), 2.62 (2H, dt), 4.25 (2H, dt), 4.63–4.82 (2H, m), 4.99 (1H, s), 5.72 (1H, s), 6.20 (1H, dt), 6.48 (1H, d), 7.19 (2H, d), 7.23–7.36 (7H, m)

2) Synthesis of mono(3-phenyl-2-propene-1-yl) 4-(4-bromophenyl)-2,6-dimethyl-1,4-dihydropyridine-3,5 -dicarboxylate:

The title compound was obtained from 698 mg (1.33 mmol) of 5-(3-phenyl-2-propene-1-yl) 3-(2-cyanoethyl) 4-(4-bromophenyl)-2,6-dimethyl-1,4-dihydropyridine-3,5-dicarboxylate in the same manner as that of Example 3-2).

Yield: 495 mg (1.06 mmol) (79.5%).
MS (ESI, m/z) 466 (M−H)−
$^1$H-NMR (DMSO-d$_6$): 2.24 (3H, s), 2.23 (3H, s), 2.29 (3H, s), 4.56–4.78 (2H, m), 4.90 (1H, s), 6.29 (1H, dt), 6.42 (1H, d), 7.13 (2H, d), 7.22–7.44 (7H, m), 8.83 (1H, s)

EXAMPLE 63

Synthesis of mono(3-(4-carboxyphenyl)-2-propene-1-yl) 4-(3-chlorophenyl)-2,6-dimethyl-1,4-dihydropyridine-3,5-dicarboxylate 1) Synthesis of 5-(3-(4-(2-cyanoethyloxycarbonyl)phenyl)-2-propene-1-yl) 3-(2-cyanoethyl) 4-(3-chlorophenyl)-2,6-dimethyl-1,4-dihydropyridine-3,5-dicarboxylate:

307 mg (0.77 mmol) of 5-(2-propene-1-yl) 3-(2-cyanoethyl) 4-(3-chlorophenyl)-2,6-dimethyl-1,4-dihydropyridine-3,5-dicarboxylate, 278 mg (0.92 mmol) of 2-cyanoethyl 4-iodobenzoate, 19 mg(0.08 mmol) of palladium acetate and 0.14 ml (1.0 mmol) of triethylamine were heated at 100° C. under stirring in 5 ml of DMF overnight. Water was added to the reaction mixture. After the extraction with ethyl acetate, the organic layer was dried over anhydrous sodium sulfate and then concentrated under reduced pressure. The residue was purified by the silica gel chromatography (hexane/ethyl acetate=2/1) to obtain the title compound.

Yield: 192 mg (0.33 mmol) (43.4%).
MS (ESI, m/z) 572 (M−H)−
$^1$H-NMR (CDCl$_3$): 2.37 (3H, s), 2.39 (3H, s), 2.63–2.90 (4H, m), 4.22–4.58 (4H, m), 4.65–4.87 (2H, m), 5.03 (1H, s), 6.02 (1H, s), 6.35 (1H, dt), 6.50 (1H, d), 7.08–7.32 (5H, m), 7.41 (2H, d), 8.01 (2H, d)

2) Synthesis of mono(3-(4-carboxyphenyl)-2-propene-1-yl) 4-(3-chlorophenyl)-2,6-dimethyl-1,4-dihydropyridine-3,5-dicarboxylate:

185 mg (0.32 mmol) of 5-(3-(4-(2-cyanoethyloxycarbonyl)phenyl)-2-propene-1-yl) 3-(2-cyanoethyl) 4-(3-chlorophenyl)-2,6-dimethyl-1,4-dihydropyridine-3,5-dicarboxylate was dissolved in 10 ml of methanol. 1 ml of 1 N aqueous sodium hydroxide solution was added to the solution, and the obtained mixture was stirred at room temperature for 3 hours. 2 N hydrochloric acid was added to the reaction mixture. Methanol was evaporated under reduced pressure. Water was added to the residue, and the solid was obtained by the filtration and then purified by thin layer silica gel chromatography (hexane/ethyl acetate=1/1) to obtain the title compound.

Yield: 8 mg (0.02 mmol) (5.3%).
MS (ESI, m/z) 466 (M−H)−
$^1$H-NMR (DMSO-d$_6$): 2.26 (3H, s), 2.31 (3H, s), 4.52–4.82 (2H, m), 4.94 (1H, s), 6.42–6.55 (1H, m), 6.59 (1H, d), 7.08–7.45 (5H, m), 7.48 (2H, d), 7.88 (2H, d), 8.89 (1H, s)

EXAMPLE 64

Synthesis of mono(3-phenyl-2-propene-1-yl) 4-(3-methoxycarbonyl)-2,6-dimethyl-1,4-dihydropyridine-3,5-dicarboxylate 277 mg (0.569 mmol) of 5-(3-phenyl-2-propene-1-yl) 3-(2-cyanoethyl) 4-(3-carboxyphenyl)-2,6-dimethyl-1,4-dihydropyridine-3,5-dicarboxylate was dissolved in 1.45 ml of methanol. 0.725 ml of a solution of trimethylsilyldiazomethane (1 mol/l) in hexane was added to the obtained solution, and they were stirred at room temperature overnight. Methanol was evaporated under reduced pressure. After the extraction with ethyl acetate, the organic layer was dried over anhydrous sodium sulfate and then concentrated under reduced pressure. The residue was dissolved in 5.7 ml of methanol. 0.57 ml of 1 N aqueous sodium hydroxide solution was added to the obtained solution, and they were stirred at room temperature for 3 hours. 2 N hydrochloric acid was added to the reaction mixture. Methanol was evaporated under reduced pressure. The residue was washed with water and hexane/ethyl acetate (1:1) and dried under reduced pressure to obtain the title compound.

Yield: 89 mg (0.198 mmol) (35%).
$^1$H-NMR (DMSO-d$_6$):2.26 (3H,s), 2.30 (3H, s), 3.76 (3H, s), 4.57–4.75 (2H, m), 4.99 (1H, s), 6.29 (1H, dt), 6.48 (1H, d), 7.24–7.47 (7H, m), 7.68–7.74 (1H, m), 7.81–7.84 (1H, m), 8.87 (1H, bs)

EXAMPLE 65

Synthesis of 5-(3-phenyl-2-propene-1-yl) 4-(3-chlorophenyl)-2-ethyl-6-methyl-1,4-dihydropyridine-3,5-dicarboxylate 1) Synthesis of (2-trimethylsilylethyl) 3-oxovalerate:

1.26 ml (10.0 mmol) of methyl 3-oxovalerate, 2.87 ml (20.0 mmol) of 2-trimethylsilylethanol and 122 mg (1.0 mmol) of 4-dimethylaminopyridine were heated under reflux in 20 ml of toluene overnight. A phosphate buffer solution was added to the obtained reaction liquid. After the extraction with ethyl acetate, the organic layer was washed with saturated aqueous salt solution and then dried over anhydrous sodium sulfate. The solvent was evaporated under reduced pressure, and the residue was purified by the silica gel chromatography (hexane/ethyl acetate=10/1) to obtain the title compound.

Yield: 2.17 g (10.0 mmol) (100%).
$^1$H-NMR (CDCl$_3$): 0.03 (9H, s), 0.97–1.03 (2H, m), 1.07 (3H, t), 2.56 (2H, q), 3.42 (2H, s), 4.08–4.14 (2H, m)

2) Synthesis of 5-(3-phenyl-2-propene-1-yl) 3-(2-trimethylsilylethyl) 4-(3-chlorophenyl)-2-ethyl-6-methyl-1,4-dihydropyridine-3,5-dicarboxylate:

649 mg (3.0 mmol) of (2-trimethylsilylethyl) 3-oxovalerate, 652 mg (3.0 mmol) of (3-phenyl-2-propene-1-yl) 3-aminocrotonate and 0.340 ml (3.0 mmol) of 3-chlorobenzaldehyde were heated at 70° C. under stirring in 15 ml of 2-propanol three nights. The solvent was evaporated under reduced pressure, and the residue was purified by the silica gel chromatography (hexane/ethyl acetate=5/1) to obtain the title compound.

Yield: 674 mg (1.26 mmol) (42%).

MS (ESI, m/z) 536 (M–H)$^-$ $^1$H-NMR (CDCl$_3$): 0.02 (9H, s), 0.87–1.07 (2H, m), 1.20 (3H, s), 2.35 (3H, s), 2.60–2.87 (2H, m), 4.14 (2H, t), 4.65–4.82 (2H, m), 5.06 (1H, s), 6.01 (1H, s), 6.24 (1H, dt), 6.55 (1H, d), 7.07–7.38 (9H, m)

3) Synthesis of 5-(3-phenyl-2-propene-1-yl) 4-(3-chlorophenyl)-2-ethyl-6-methyl-1,4-dihydropyridine-3,5-dicarboxylate:

674 mg (1.26 mmol) of 5-(3-phenyl-2-propene-1-yl) 3-(2-trimethylsilyl) 4-(3-chlorophenyl)-2-ethyl-6-methyl-1,4-dihydropyridine-3,5-dicarboxylate was dissolved in 3.78 ml of tetrahydrofuran. 3.78 ml of a solution of tetrabutylammonium fluoride (1 mol/l) in tetrahydrofuran was added to the obtained solution. They were stirred at 40° C. three nights. Tetrahydrofuran was evaporated under reduced pressure. Methanol and 2 N hydrochloric acid were added to the residue. Methanol was evaporated under reduced pressure. After the extraction with ethyl acetate, the organic layer was dried over anhydrous sodium sulfate, and then concentrated under reduced pressure. The residue was washed with hexane/ethyl acetate (1:1) and dried under reduced pressure to obtain the title compound.

Yield: 151 mg (0.344 mmol) (27%).

$^1$H-NMR (DMSO-d$_6$): 1.03–1.19 (2H, m), 2.30 (3H, s), 2.60–2.77 (2H, m), 4.59–4.77 (2H, m), 4.92 (1H, s), 6.33 (1H, dt), 6.53 (1H, d), 8.86 (1H, bs)

The structural formulae of the compounds synthesized as described above are shown in the following Table together with Example numbers.

1

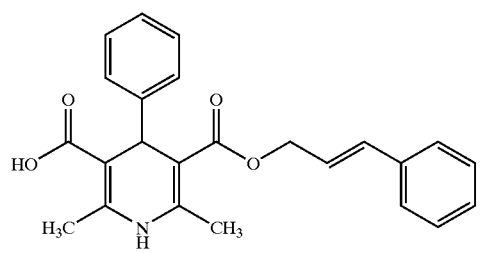

2

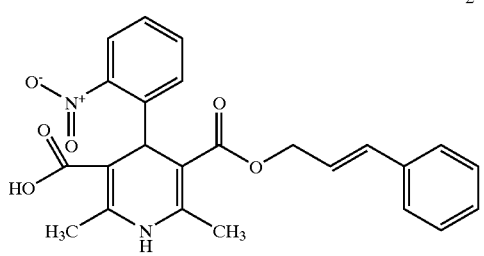

-continued

3

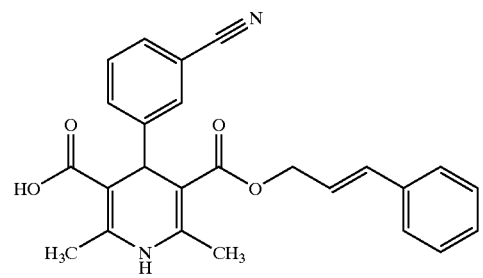

4

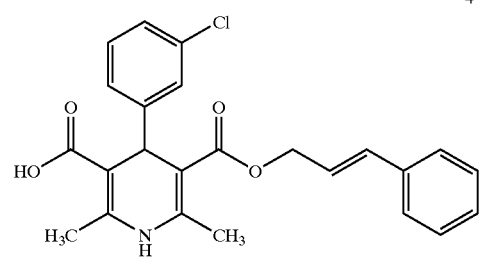

5

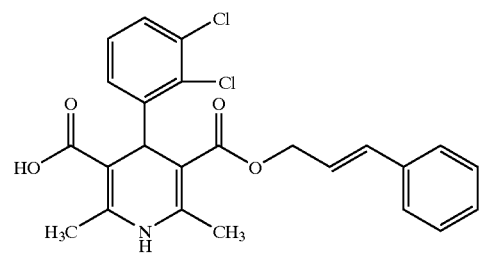

6

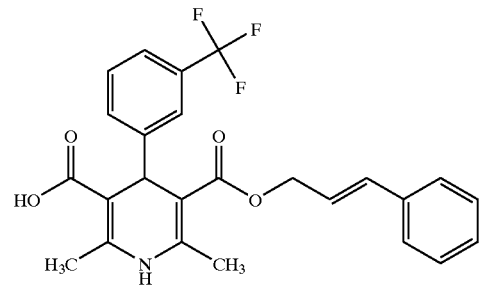

7

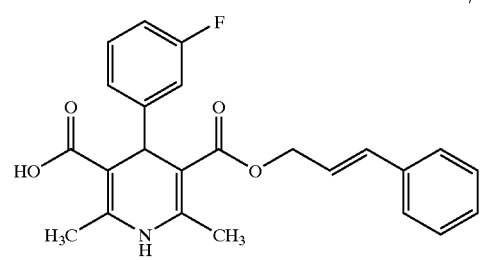

-continued
8
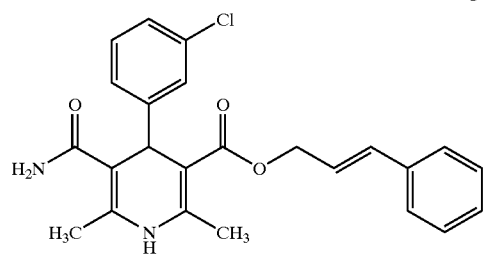
9
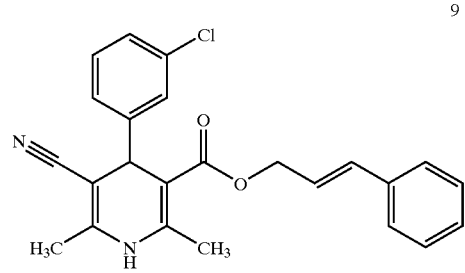
10
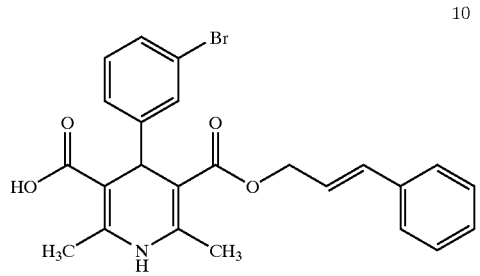
11
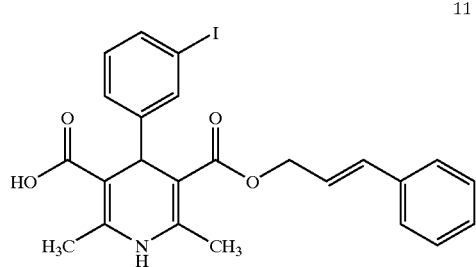
12
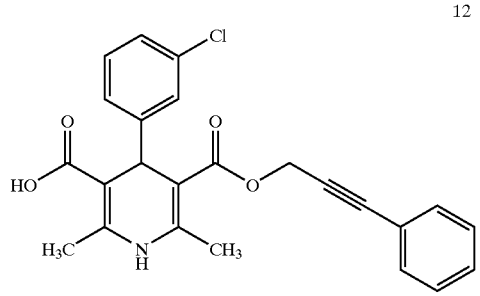
-continued
13
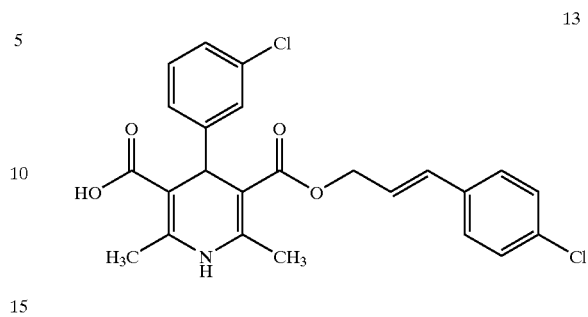
14
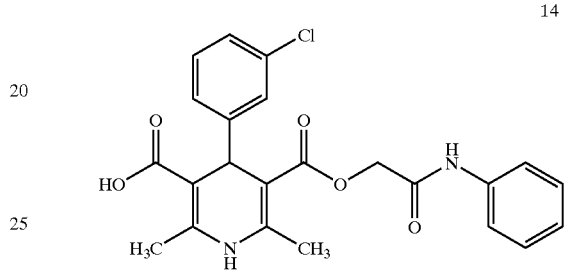
15
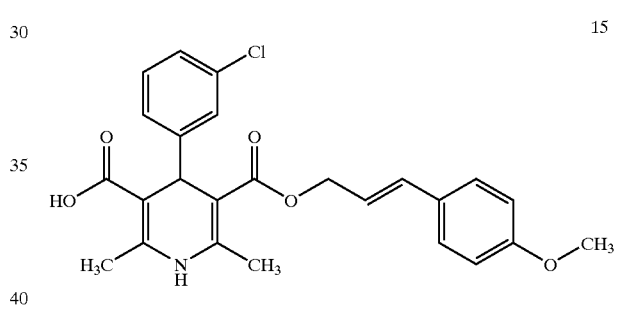
16
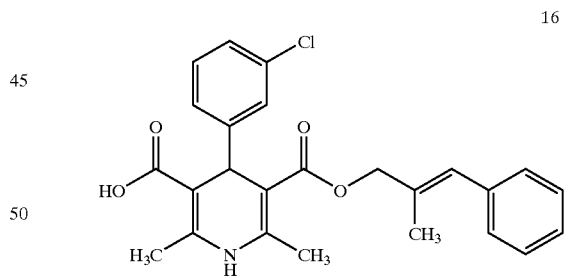
17
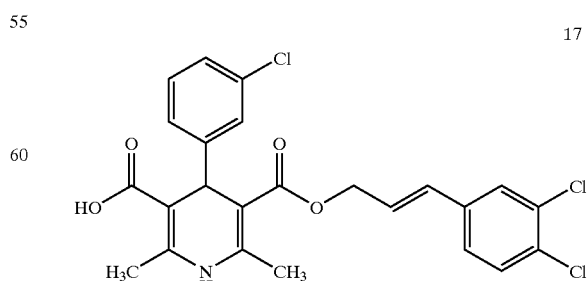

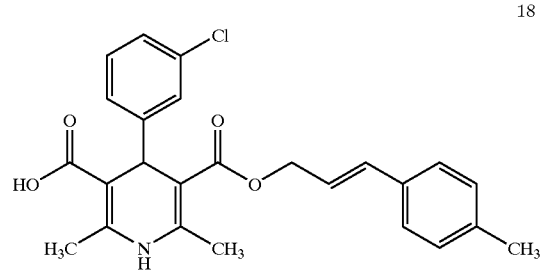
18
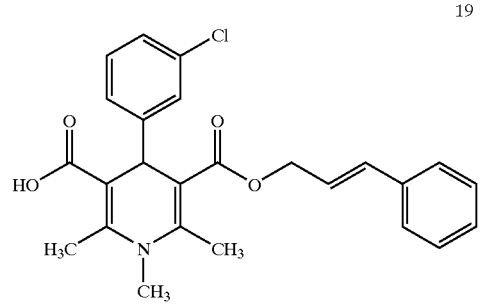
19
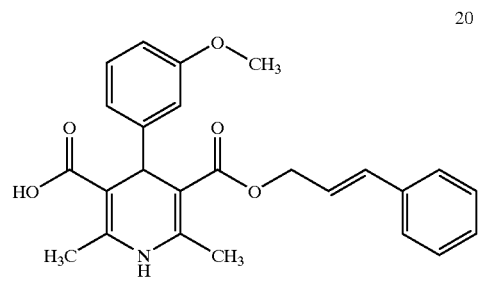
20
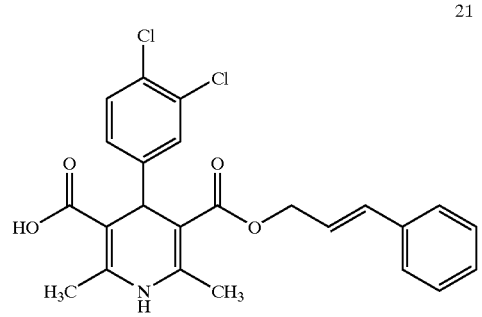
21
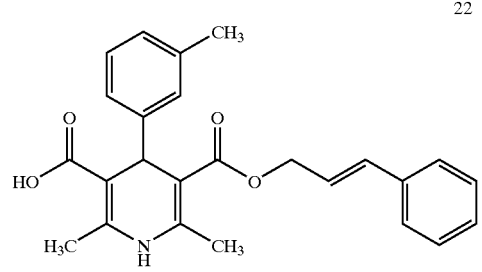
22
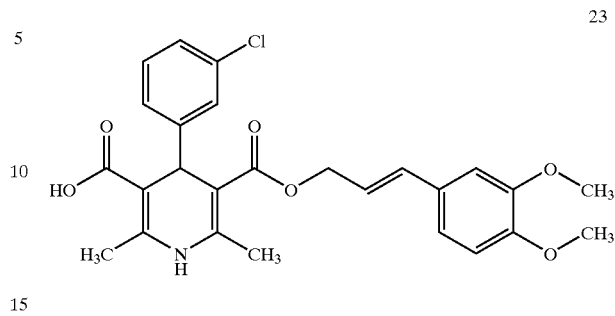
23
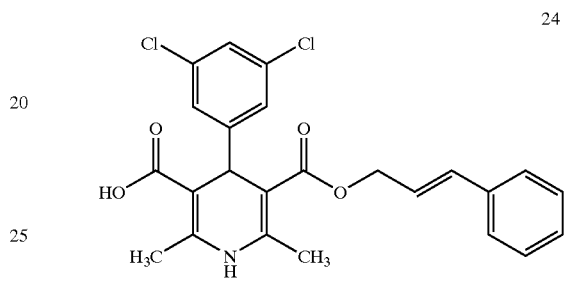
24
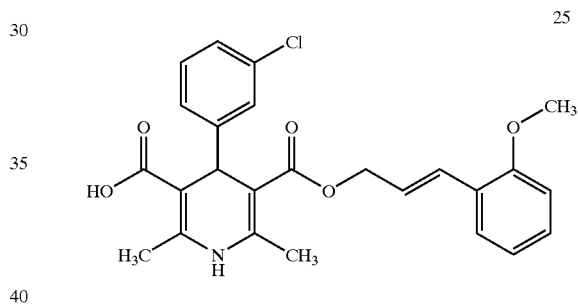
25
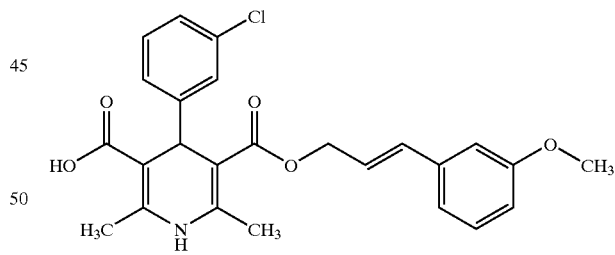
26
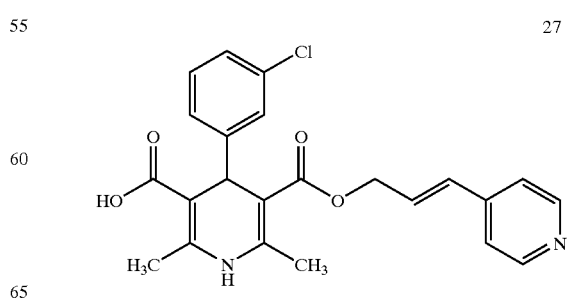
27

-continued
28
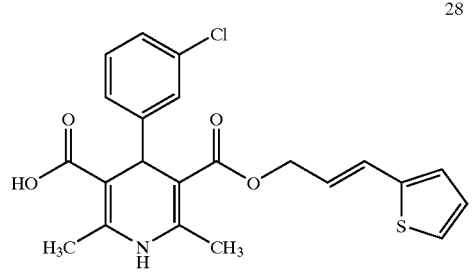
29 (-)
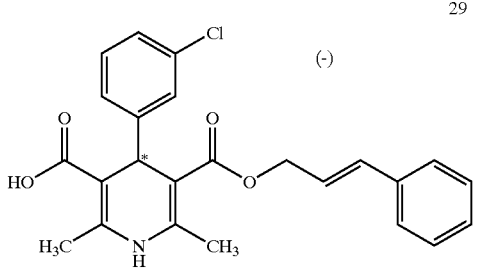
30
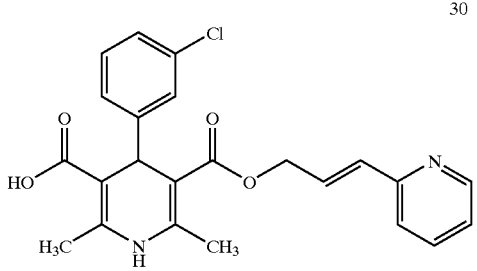
31
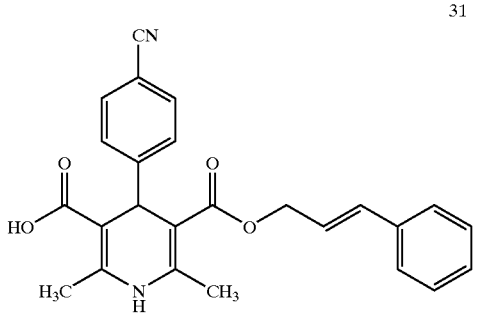
32
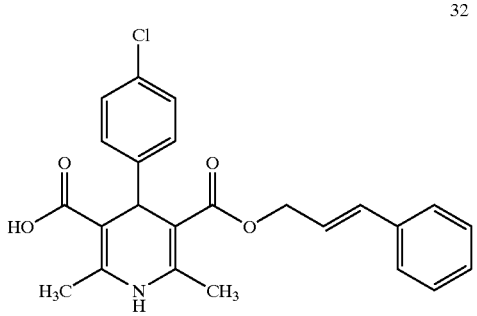
-continued
33
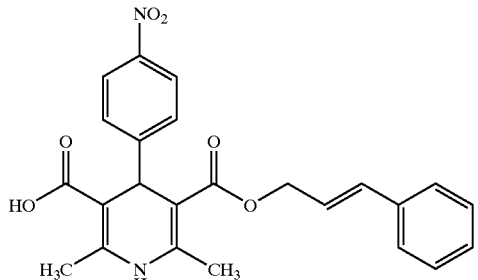
34 (+)
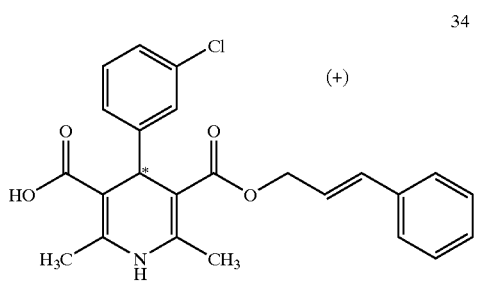
35
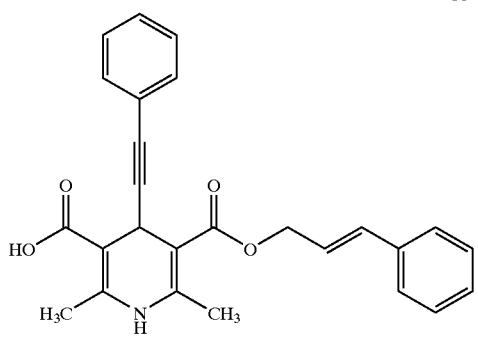
36
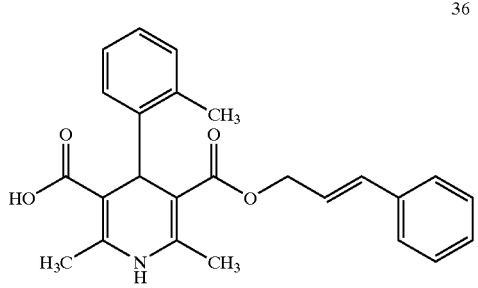
37
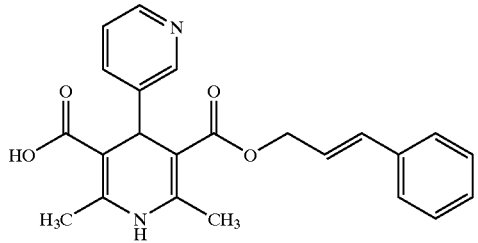

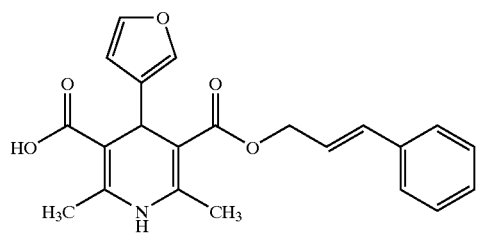
38
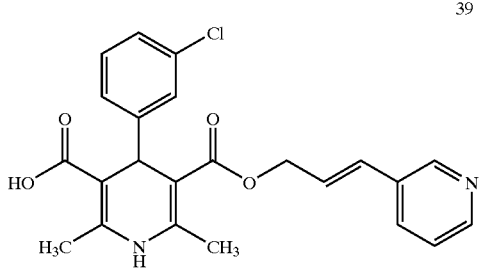
39
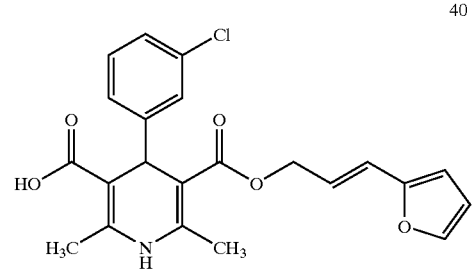
40
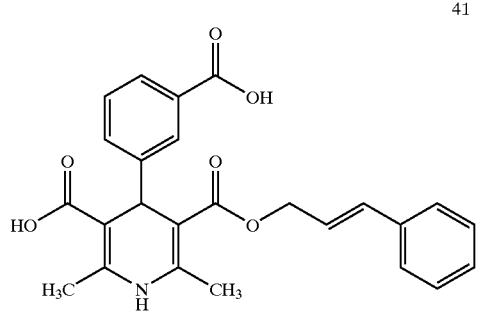
41
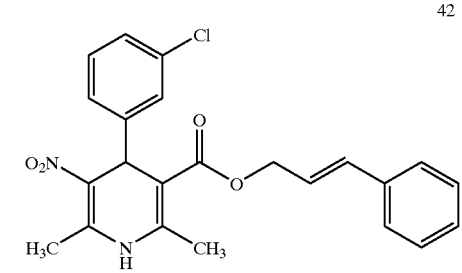
42
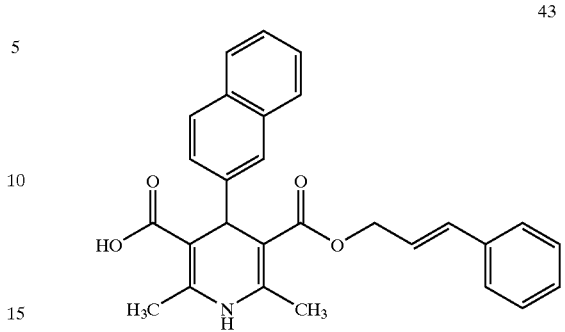
43
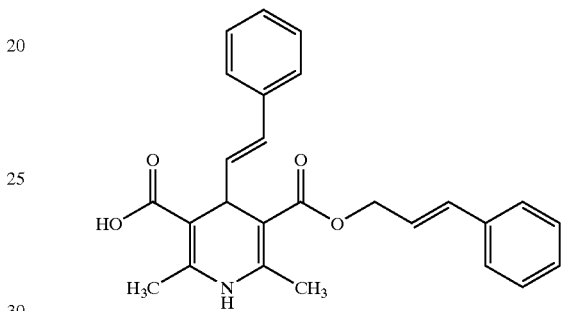
44
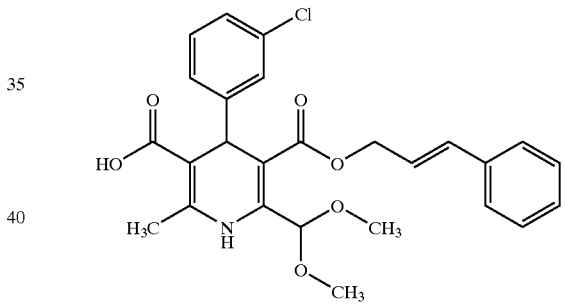
45
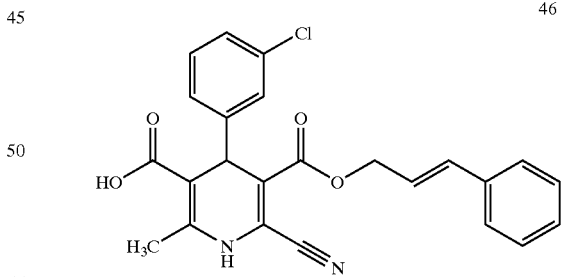
46
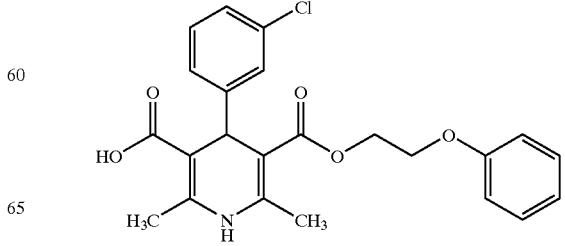
47

-continued
48
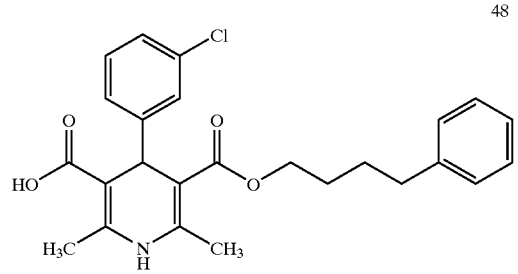
49
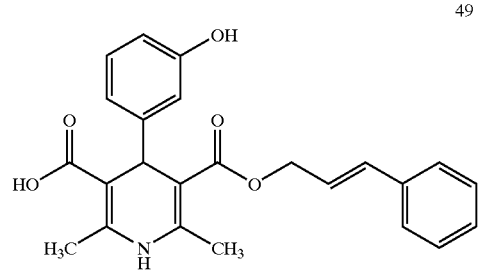
50
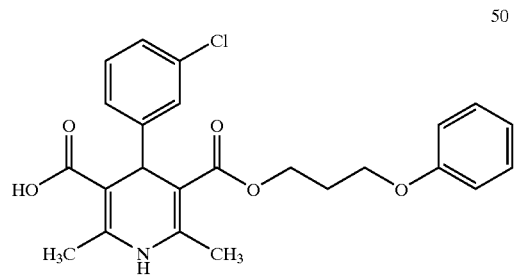
51
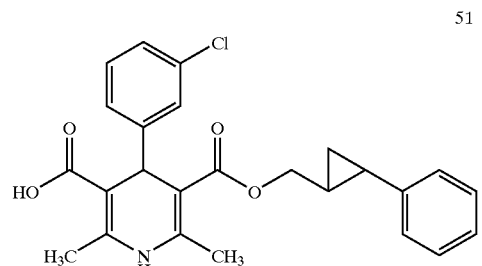
52
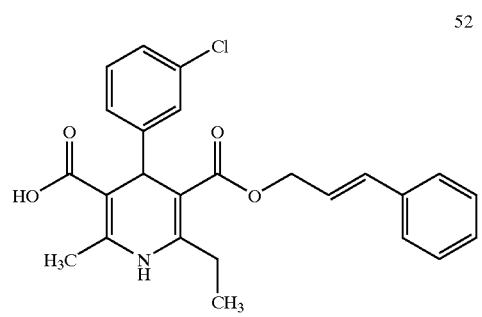
-continued
53
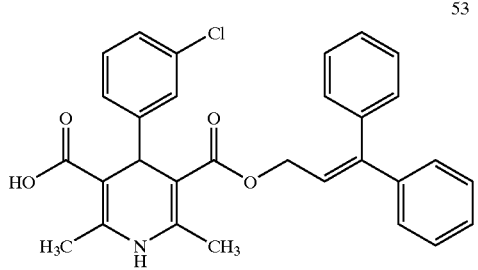
54
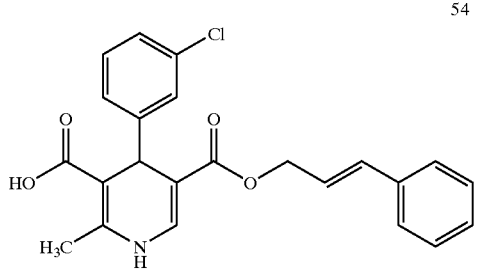
55
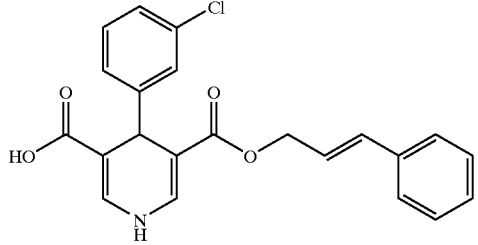
56
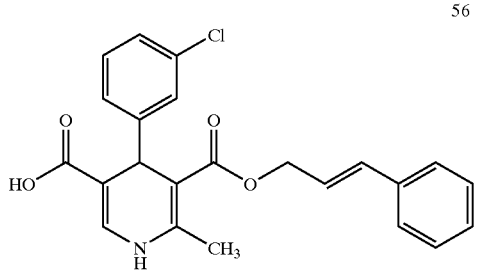
57
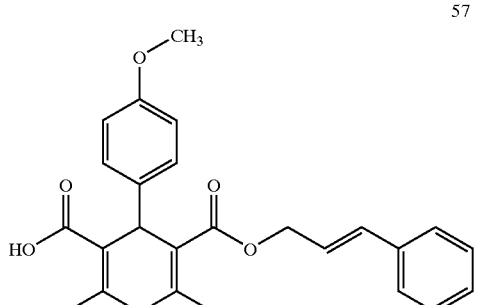

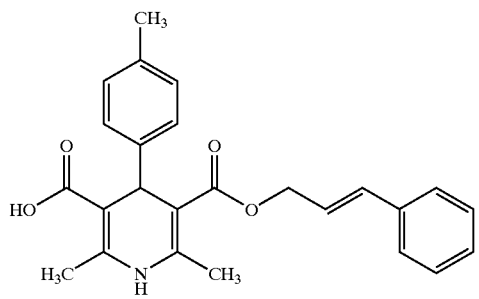

58

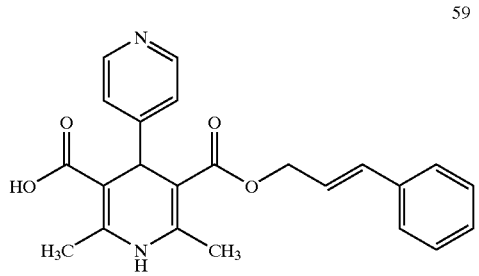

59

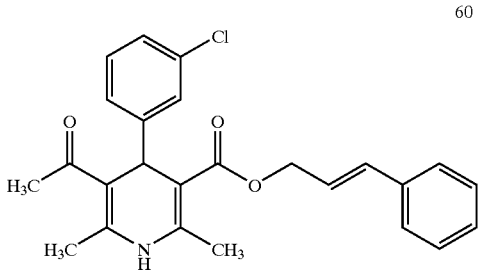

60

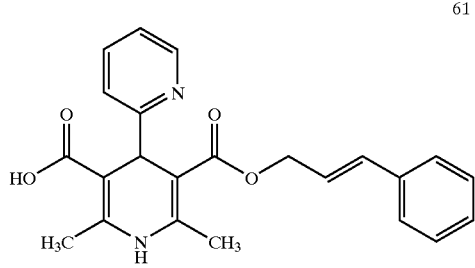

61

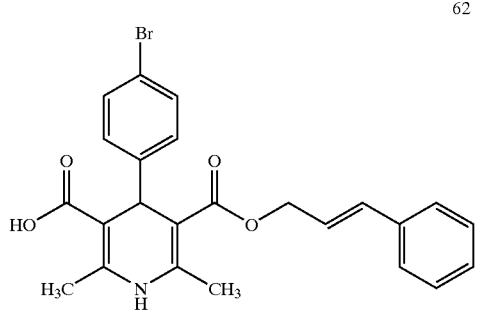

62

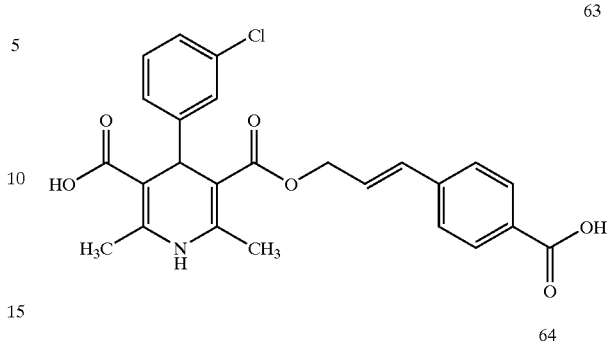

63

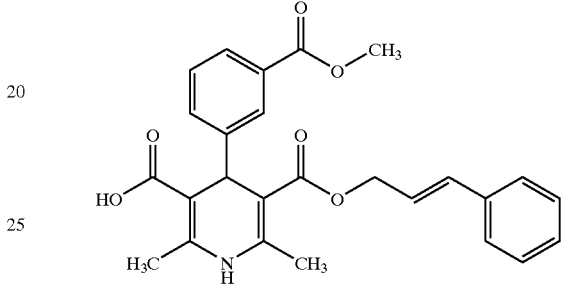

64

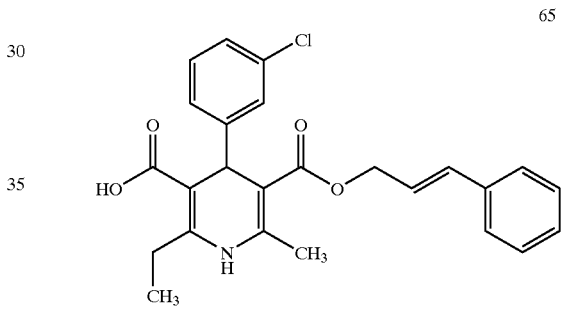

65

(Test Examples) Inhibition Activity of N-type Calcium Channel:

The activity of dihydropyridine derivatives of the present invention to the inhibition of N-type calcium channel was determined by the following method wherein the calcium currents in cells of maxillary sympathetic ganglions of rats were detected by the whole cell voltage clamp method as described below.

1) Preparation of cells of maxillary sympathetic ganglions of rats:

The cervix of each of Wistar rats (2 to 4 weeks old) was opened to expose the maxillary ganglions under anesthesia with pentobarbital. A pair of the ganglions were removed and immediately washed with $Ca^{2+}$-free Tyrode solution cooled with ice. Each ganglion was cut into 3 or 4 pieces and kept in the $Ca^{2+}$-free Tyrode solution for 15 minutes. Then, these pieces were treated with papain [Washington Biochemicals (lot#35J557); 20 U/ml] and then with a mixture of type-2 collagenase [Washington Biochemicals (CLS2); 5900 U/ml] and dispase [Calbiochem (lot#1312973); 16 mg/ml] for one hour. After enzymatic treatment, the ganglion cells were mechanically isolated by pipetting. The isolated ganglion cells were used for the experiments within 6 hours.

2) Determination of calcium Electric Current:

The calcium electric current was determined by the whole cell voltage clamp method under the fixed membrane potential. The pipette electrode was pulled from glass tube (inner diameter: 1.5 mm; Narishige) in two stage of a vertical pipette puller (PB-7; Narishige). The ionic current was amplified with a patch amplifier (CEZ-2300; Nihon Kohden Corporation). The noises were cut at 10 kHz (E-3201B, NF Electronic Instrument) and then the ionic current was monitored on a storage oscilloscope (DS-9121, Iwatsu) and, at the same time, recorded with a DAT data recorder (RD-120TE, TEAC). Then it was passed through a 1 kHz filter and recorded in a computer (Compaq DeskPro) with pCLAMP software (Axon Instrument) of 3 kHz. All the experiments were performed at room temperature (25±2° C.). In the measurement of current through the calcium channel, 10 mM barium (composition of the solution: shown below) was used in place of calcium as the charge carrier. The transmission of barium through the calcium channel was better than that of calcium in the sympathetic ganglion cells, and the calcium-dependent channel inactivation was slight when barium was used.

The test compounds were rapidly administered by Y-tube method by Murase et al. [Brain Res. 525, 84 (1990)]. Each compound was dissolved in DMSO, preparing 10 mM mother solution. At the highest drug concentration used, the vehicle (0.1%) had no significant effect on the calcium current.

2) Composition of Normal Tyrode's Solution: NaCl; 143, KCl; 4, $MgCl_2$; 0.5; $CaCl_2$; 1.8, glucose; 5.5, $NaH_2PO_4$; 0.33, HEPES; 5 (Mm). The pH was adjusted to 7.4 with tris-OH.

Composition of Ca-free Tyrode's solution: the same as that of the Normal Tyrode's solution except that it was free of $CaCl_2$ External solution for the determination of calcium electric current (mM): TEACl; 144, CsCl; 4, $BaCl_2$ 1.8, $MgCl_2$; 0.53, glucose: 5.5, HEPES; 5 (pH 7.4)

Solution in patch electrode: CsCl; 140, $MgCl_2$; 5, $CaCl_2$; 0.28, HEPES; 10 (pH 7.2), EGTA; 5 (pH 7.2).

3) Results:

The electric current was induced by the depolarization for 50 ms, from the holding potential of −60 mV to the test potential of 0 mV. This test potential was the peak in the current/voltage relationship, and the inhibition effect was examined at this point at which the error by the drift of the holding potential was reduced. As Tsein et al. reported, the maxillary ganglion cells were substantially free of L-type component (not more than 5%), and at least 85% thereof comprised the N-type component. After recording a calcium electric current for 5 continuous pulses, the test compound was cumulatively added with concentrations of 0.1, 1 and 10 uM. The pretreatment time for the compound of each concentration was 2 minutes. The inhibition activity of the dihydropyridine derivatives (1 uM) thus determined was 10 to 70%.

The results of the determination of the inhibition activity of the dihydropyridine derivatives (0.1 uM) are shown in Table 2.

TABLE 2

| Example | N-type inhibition 0.1 uM (%) | L-type inhibition 100 nM (%) | IC50, nM |
|---|---|---|---|
| 3 | 47.49 | 98 | 6.3 (1.7) |
| 8 | 31.45 | 75 | 32 (21) |
| 9 | 21.34 | 56 | 82 (4.7) |
| 14 | 28.56 | 70 | 50 (3.2) |
| 20 | 24.29 | 38 | 250 (53) |

It is apparent from the above-described facts that the new dihydropyridine derivatives have an excellent activity of inhibition of N-type calcium channel. The activity of inhibiting the L-type calcium channel of them was also examined to find that it was weak.

The new dihydropyridine derivatives of the present invention had the activity of selectively inhibit the action of the N-type calcium channel. Therefore, the new dihydropyridine derivatives of the present invention are usable for the treatment of encephalopathies caused by the ischemia in the acute phase after the onset of cerebral infarction, cerebral hemorrhage (including subarachnoidal bleeding) or the like; progressive neurodegenerative diseases; e.g. Alzheimer's disease; AIDS related dementia; Parkinson's disease; dementia caused by cerebrovascular disorders and ALS; neuropathy caused by head injury; sharp pain and a cold feeling caused by diabetes or thromboangitis obliterans; pain after an operation; various pains, e.g. migraine and visceral pain; bronchial asthma; various diseases caused by psychogenic stress, e.g. unstable angina and hypersensitive colon inflammation; emotional disorder; and drug addiction withdrawal symptoms, e.g. ethanol addiction withdrawal symptoms.

What is claimed is:

1. A pharmaceutical composition containing a dihydropyridine derivative represented by the following formula (1) or a pharmaceutically acceptable salt thereof as the active ingredient, wherein the composition is suitable for treating any of encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation, and drug addiction withdrawal symptoms:

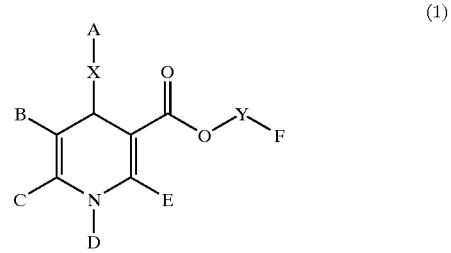

(1)

wherein

A represents a group of the following formula (2), thiophene-3-yl group, thiophene-2-yl group, furan-3-yl group, furan-2-yl group, pyridine-4-yl group, pyridine-3-yl group or pyridine-2-yl group:

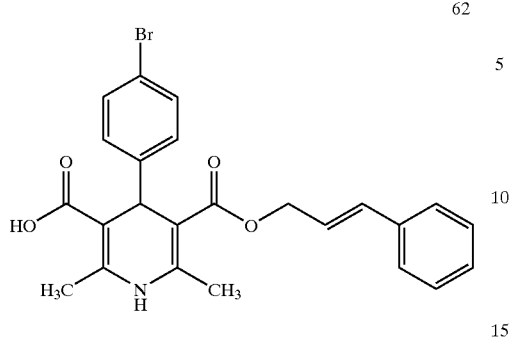

(62)

wherein R¹, R², R³, R⁴ and R⁵ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl, a hydroxy-lower alkenyl, a halogeno-lower alkyl group, a halogeno-lower alkoxyl group, a halogeno-lower alkenyl group, an aryl-lower alkoxyl group, a lower alkoxycarbonyl group or an aroyl group, B represents a carbamoyl group, cyano group, nitro group, acetyl group or carboxyl group, C represents a hydrogen atom, methyl group, ethyl group or dimethoxymethyl group, D represents a hydrogen atom, a lower alkyl group, a hydroxy-lower alkyl group or an aryl-lower alkyl group, E represents a hydrogen atom, methyl group, ethyl group, dimethoxymethyl group or cyano group, F represents a group of the following formula (3), cyclohexyl group, thiophene-3-yl group, thiophene-2-yl group, furan-3-yl group, furan-2-yl group, pyridine-4-yl group, pyridine-3-yl group or pyridine-2-yl group,

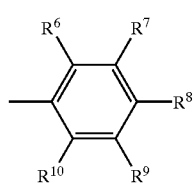

(3)

wherein R⁶, R⁷, R⁸, R⁹ and R¹⁰ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower an alkoxycarbonyl group or an aroyl group, X represents an interatomic bond, —CH₂—, —CH₂CH₂—, —CH=CH— or —C≡—, and Y is represented by a group of the following formulae (4), (7), (8), (11) or (12):

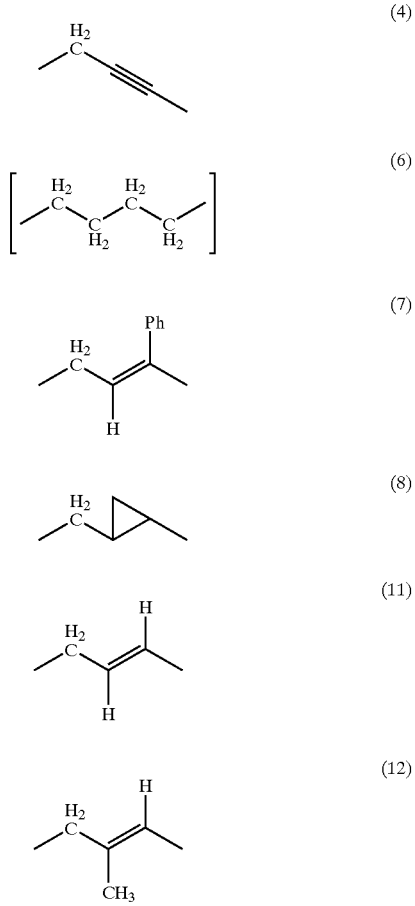

wherein two of R¹ to R³ may be bonded together to form a ring.

2. The pharmaceutical composition of claim 1, wherein R¹, R², R³, R⁴ and R⁵ in formula (2) may be the same or different from each other, and each represents a hydrogen atom, a halogen atom, hydroxyl group, carboxyl group, cyano group, nitro group, a lower alkyl group, a lower alkoxyl group, a halogeno-lower alkyl group or a lower alkoxycarbonyl group.

3. The pharmaceutical composition of claim 1, wherein B represents a carboxyl group, D represents a hydrogen atom, X represents an interatomic bond, and Y is represented by formula (11).

4. The pharmaceutical composition of claim 1, wherein
A is represented by formula (2), wherein R¹ and R³ may be the same or different from each other, and each represent hydrogen atom, a halogen atom, hydroxyl group, amino group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, an aryl-lower alkenyl group or an aroyl group;

R² represents a hydrogen atom, a halogen atom, hydroxyl group, amino group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group or an aroyl group; $R^4$ and $R^5$ each represent hydrogen atom; and two of $R^1$ to $R^3$ may be bonded together to form a ring;

B represents a carboxyl group;

C represents a methyl group;

D represents a hydrogen atom, a lower alkyl group, a hydroxy-lower alkyl group or an aryl-lower alkyl group;

E represents a methyl group;

F is represented by formula (3), wherein $R^6$, $R^7$, $R^8$, $R^9$ and $R^{10}$ may be the same or different from each other, and each represent hydrogen atom, a halogen atom, hydroxyl group, amino group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkenyl group, a halogeno-lower alkoxyl group, an aryl-lower alkoxyl group or an aroyl group;

X represents an interatomic bond; and

Y represents a group of formula (11) or (12).

5. The pharmaceutical composition of claim 1, wherein B represents a carboxyl group.

6. The pharmaceutical composition of claim 1, wherein Y is represented by formula (4).

7. The pharmaceutical composition of claim 1, wherein Y is represented by formula (7).

8. The pharmaceutical composition of claim 1, wherein Y is represented by formula (8).

9. The pharmaceutical composition of claim 1, wherein Y is represented by formula (11).

10. The pharmaceutical composition of claim 1, wherein Y is represented by formula (12).

11. The pharmaceutical composition of claim 1, wherein the dihydropyridine derivative is mono(3-phenyl-2-propene-1-yl)4-(3-cyanophenyl)-2,6-dimethyl-1,4-dihydropyridine-3,5-dicarboxylate.

12. The pharmaceutical composition of claim 1, which is suitable for treating cerebral infarction.

13. The pharmaceutical composition of claim 1, further comprising a pharmaceutically acceptable carrier and/or diluent.

14. A method of treating a condition selected from the group consisting of encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation, and drug addiction withdrawal symptoms, comprising administering an effective amount of the pharmaceutical composition of claim 1 to a patient in need thereof.

15. A method of treating sharp pain caused by thromboangitis obliterans, comprising administering an effective amount of a pharmaceutical containing a dihydropyridine derivative represented by the following formula (1) or a pharmaceutically acceptable salt thereof as the active ingredient:

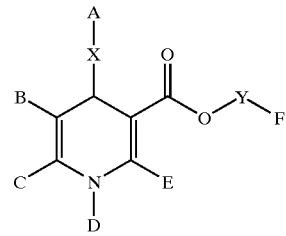

(1)

wherein

A represents a group of the following formula (2), thiophene-3-yl group, thiophene-2-yl group, furan-3-yl group, furan-2-yl group, pyridine-4-yl group, pyridine-3-yl group or pyridine-2-yl group:

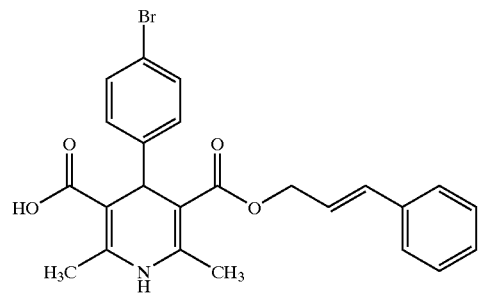

62 wherein $R^1$, $R^2$, $R^3$, $R^4$ and $R^5$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl, a hydroxy-lower alkenyl, a halogeno-lower alkyl group, a halogeno-lower alkoxyl group, a halogeno-lower alkenyl group, an aryl-lower alkoxyl group, a lower alkoxycarbonyl group or an aroyl group, B represents a carbamoyl group, cyano group, nitro group, acetyl group or carboxyl group, C represents a hydrogen atom, methyl group, ethyl group or dimethoxymethyl group, D represents a hydrogen atom, a lower alkyl group, a hydroxy-lower alkyl group or an aryl-lower alkyl group, E represents a hydrogen atom, methyl group, ethyl group, dimethoxymethyl group or cyano group, F represents a group of the following formula (3), cyclohexyl group, thiophene-3-yl group, thiophene-2-yl group, furan-3-yl group, furan-2-yl group, pyridine-4-yl group, pyridine-3-yl group or pyridine-2-yl group, (3)

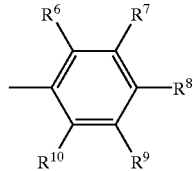

wherein $R^6$, $R^7$, $R^8$, $R^9$ and $R^{10}$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group, a lower an alkoxycarbonyl group or an aroyl group, X represents an interatomic bond, —CH$^2$—, —CH$^2$CH$^2$—, —CH=CH— or —C≡C—, and Y is represented by a group of the following formulae (4), (6), (7), (8), (11) or (12):

(4)

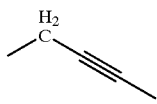

-continued (6)

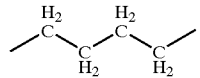

(7)

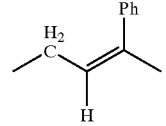

(8)

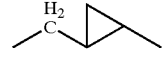

(11)

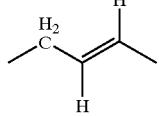

(12)

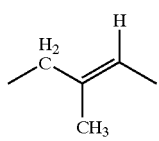

wherein two of $R^1$ to $R^3$ may be bonded together to form a ring.

16. The method of claim 15, wherein Y is represented by a group of the formula (4), (7), (8), (11) or (12).

* * * * *

UNITED STATES PATENT AND TRADEMARK OFFICE
CERTIFICATE OF CORRECTION

PATENT NO.     : 6,995,179 B2                                                              Page 1 of 1
DATED          : February 7, 2006
INVENTOR(S)    : Uneyama et al.

It is certified that error appears in the above-identified patent and that said Letters Patent is hereby corrected as shown below:

<u>Title page,</u>
Item [45] and [*] Notice, should read:
-- [45] **Date of Patent: * Feb. 7, 2006**

[*]   Notice:   Subject to any disclaimer, the term of this
                patent is extended or adjusted under 35
                U.S.C. 154(b) by 191 days.

This patent is subject to a terminal disclaimer. --.

Signed and Sealed this

Eleventh Day of April, 2006

JON W. DUDAS
*Director of the United States Patent and Trademark Office*